United States Patent
Arimoto et al.

(10) Patent No.: US 11,986,480 B2
(45) Date of Patent: May 21, 2024

(54) HETEROCYCLIC COMPOUND

(71) Applicant: TOHOKU UNIVERSITY, Sendai (JP)

(72) Inventors: Hirokazu Arimoto, Sendai (JP); Kaori Itto, Sendai (JP); Daiki Takahashi, Sendai (JP); Nobuo Cho, Fujisawa (JP); Hiroshi Nara, Fujisawa (JP); Kenichiro Shimokawa, Fijisawa (JP); Taiichi Ohra, Fujisawa (JP); Shigekazu Sasaki, Fujisawa (JP); Naoki Ishii, Fujisawa (JP)

(73) Assignee: TOHOKU UNIVERSITY, Miyagi (JP)

( * ) Notice: Subject to any disclaimer, the term of this patent is extended or adjusted under 35 U.S.C. 154(b) by 0 days.

(21) Appl. No.: 16/482,994

(22) PCT Filed: Feb. 2, 2018

(86) PCT No.: PCT/JP2018/003576
§ 371 (c)(1),
(2) Date: Oct. 28, 2019

(87) PCT Pub. No.: WO2018/143403
PCT Pub. Date: Aug. 9, 2018

(65) Prior Publication Data
US 2020/0163970 A1 May 28, 2020

(30) Foreign Application Priority Data
Feb. 3, 2017 (JP) .................... 2017-019127

(51) Int. Cl.
| | | |
|---|---|---|
| C07D 495/04 | (2006.01) | |
| A61K 31/513 | (2006.01) | |
| A61K 31/522 | (2006.01) | |
| A61K 31/551 | (2006.01) | |

(52) U.S. Cl.
CPC .......... A61K 31/522 (2013.01); A61K 31/513 (2013.01); A61K 31/551 (2013.01); C07D 495/04 (2013.01)

(58) Field of Classification Search
CPC .................................................. C07D 495/04
See application file for complete search history.

(56) References Cited

U.S. PATENT DOCUMENTS

| | | | |
|---|---|---|---|
| 2004/0096825 A1 | 5/2004 | Chenna et al. | |
| 2007/0161007 A1 | 7/2007 | Rajski et al. | |
| 2019/0292214 A1* | 9/2019 | Genieser | A61P 33/00 |
| 2020/0223848 A1* | 7/2020 | Arimoto | A61K 31/522 |
| 2021/0317156 A1* | 10/2021 | Genieser | A61P 31/00 |

FOREIGN PATENT DOCUMENTS

| | | |
|---|---|---|
| CN | 103951724 | 7/2014 |
| WO | 2006/030803 | 3/2006 |
| WO | 2006/137190 | 12/2006 |
| WO | 2008/051826 | 5/2008 |
| WO | 2008/115319 | 9/2008 |
| WO | WO 2008122038 A1 | 10/2008 |
| WO | 2010/090541 | 8/2010 |
| WO | WO 2012087336 A1 | 6/2012 |
| WO | WO 2012088254 A1 | 6/2012 |
| WO | WO 2013/078244 A1 | 5/2013 |
| WO | WO 2016119856 A1 | 8/2016 |

OTHER PUBLICATIONS

Czlapinski et al., "Conditional glycosylation in eukaryotic cells using a biocompatible chemical inducer of dimerization." J Am Chem Soc. Oct. 8, 2008; 130(40):13186-7.
Erhart et al., "Chemical development of intracellular protein heterodimerizers." Chem Biol. Apr. 18, 2013;20(4):549-57.
Feng et al., "A rapidly reversible Chemical Dimerizer System to Study Lipid Signaling in Living Cells." Angewandte Chemie, Int. Ed. 2014, 53:6720-6723.
International Search Report and Written Opinion of the International Searching Authority, PCT Application No. PCT/UJP2018/003576, mailed Mar. 27, 2018, 12 pages.
Itoh et al., "Endogenous nitrated nucleotide is a key mediator of autophagy and innate defense against bacteria." Mol Cell. Dec. 26, 2013;52(6):794-804.
Master's thesis of Mr. Takahashi in Tohoku University in 2015, "Role of S-guanylation in selective autophagy." Laboratory of Analytical Bioorganic Chemistry, 4 pages.
Master's thesis of Ms. Sato in Tohoku University in 2015, "Artificial degradation of proteins using nitroguanine derivatives." Analytical Bioorganic Chemistry Laboratory, 5 pages.
Zimmermann et al., "Cell-permeant and photocleavable chemical inducer of dimerization." Angew Chem Int Ed Engl. Apr. 25, 2014; 53(18):4717-20.
Chiaki et al., "Endogenous Nitrated Nucleotide is a Key Mediator of Autophagy and Innate Defense against Bacteria." Molecular Cell Dec. 2013, 52: 794-804.
Vakifahmetoglu-Norberg et al., "Pharmacologic agents targeting autophagy." J. Clin. Invest. 2015; 125(1): 5-13.
Los et al., "HaloTag: A Novel Protein Labeling Technology for Cell Imaging and Protein Analysis." ACS Chemical Biology 2008, 3(6):373-382.
European Search Report dated Dec. 16, 2020, European Application No. 18747735.1, 11 pages.

(Continued)

Primary Examiner — Brian E McDowell

(74) Attorney, Agent, or Firm — WENDEROTH, LIND & PONACK, L.L.P.

(57) ABSTRACT

Provided is a novel compound or salt thereof that induces degradation by autophagy of an intracellular molecule. In this compound, a ligand having activity to bind to an intracellular molecule and a structure having activity to induce autophagy of an intracellular molecule are linked via a linker without loss of the activity of the ligand and the structure.

13 Claims, No Drawings

Specification includes a Sequence Listing.

(56) References Cited

OTHER PUBLICATIONS

English language translation of Notice of Reasons for Refusal issued Mar. 2, 2022 in corresponding Japanese Patent Application No. 2018-566120.

Khanh Kim Dao et al., "Epac1 and cAMP-dependent Protein Kinase Holoenzyme Have Similar cAMP Affinity, but Their cAMP Domains Nucleotide Recognition", Journal of Biology Chemistry, 2006, vol. 281, No. 30, pp. 21500-21511.

Yan Luo et al., "The cAMP Capture Compound Mass Spectrometry as a Novel Tool for Targeting cAMP-binding Proteins", Molecular & Cellular Proteomics, 2009, vol. 8, No. 12, pp. 2843-2856.

Lutz Schmit et al., "ATP-Lipids-Protein Anchor and Energy Source in Two Dimensions", Journal of American Chemical Society, 1996, vol. 118, pp. 5532-5543.

Dagmar Klostermeier et al., "Functional Properties of the Molecular Chaperone DnaK from Thermus thermophilus", Journal of Molecular Biology, 1998, vol. 279, pp. 841-853.

Goran Pjevaljcic et al., "Design of a New Fluorescent Cofactor for DNA Methyltransferases and Sequence-Specific Labeling of DNA", Journal of American Chemistry Soc., vol. 125, pp. 3486-3492, 2003.

Sergey V. Slepenkov et al., "Detection of a concerted conformational change in the ATPase domain of DnaK triggered by peptide binding", FEBS Letters, vol. 539, pp. 100-104, 2003.

David W. Koh et al., "SAR Analysis of Adenosine Diphosphate (Hydroxymethyl) pyrrolidinediol inhibition of Poly (ADP-ribose) Glycohydrolase", J. Med. Chem, vol. 46, pp. 4322-4332, 2003.

Tung-Chung Mou et al., "Broad Specificity of Mammalian Adenylyl Cyclase for Interaction with 2', 3'-Substituted Purine-and Pyrimidine Nucleotide Inhibitors", Mol. Pharmacol. vol. 70, 99. 878-886, 2006.

Jose A. Restituyo et al., "Conversion of Aryl Azides to O-Alkyl Imidates via Modified Staudinger Ligation", Organic Letters, vol. 5, No. 23, pp. 4357-4360, 2003.

Jessica Zayas et al., "Strain Promoted Click Chemistry of 2- or 8-Azidopurine and 5-Azidopyrimidine Nucleosides and 8-Azidoadenosine Triphosphate with Cyclooctynes. Application to living Cell Fluorescent Imaging", Bioconjugate Chemistry, vol. 26, 99. 1519-1532, 2015.

Kazuya Tatani et al., "Identification of Adenine and Benzimidazole Nucleosides as Potent Human Concentrative Nucleoside Transporter 2 Inhibitors: Potential Treatment for Hyperuricemia and Gout", Journal of Medicinal Chemistry, vol. 59, 99. 3719-3731, 2016.

I.A. Grivennikov et al., "cAMP-Dependent Protein Kinase from Pigeon Breast Muscle. Isolation of the regulatory subunit by the method of affinity chromatography and study of the topography of the camp-binding site using cAMP analogs", vol. 49, pp. 1395-1406, Biochemistry (Moscow), 1984.

Evgenii S. et al., "Structure and Mechanism of Action of Cyclic AMP-Dependent Protein Kinase", Proc. FEBS Meeting, pp. 101-113, 1979.

Robert J. Carrico et al., "ATP-Labeled Ligands and Firefly Luciferase for Monitoring Specific Protein-Binding Reactions", Methods in Enzymology, vol. 57, pp. 113-122, 1978.

N. M. Mirsalikhova et al., "Interaction of Na, K-ATPase with modifying ATP analogs and chloromethylphosphonic Acid", Biochemistry (Moscow), vol. 46, pp. 314-326, pp. 258-267, 1981.

Takahashi, Daiki et al., "Second-Generation AUTACs for Targeted Autographic Degradation", Journal of Medicinal Chemistry, Aug. 17, 2023, 31 pages.

\* cited by examiner

SEQUENCE LISTING

<160> NUMBER OF SEQ ID NOS: 1

<210> SEQ ID NO 1
<211> LENGTH: 6890
<212> TYPE: DNA
<213> ORGANISM: Artificial Sequence
<220> FEATURE:
<223> OTHER INFORMATION: pCMV-EmGFP-HaloTag

<400> SEQUENCE: 1
tcaatattgg ccattagcca tattattcat tggttatata gcataaatca atattggcta    60
ttggccattg catacgttgt atctatatca taatatgtac atttatattg gctcatgtcc   120

| | |
|---|---|
| aatatgaccg ccatgttggc attgattatt gactagttat taatagtaat caattacggg | 180 |
| gtcattagtt catagcccat atatggagtt ccgcgttaca taacttacgg taaatggccc | 240 |
| gcctggctga ccgcccaacg accccgccc attgacgtca ataatgacgt atgttcccat | 300 |
| agtaacgcca atagggactt tccattgacg tcaatgggtg gagtatttac ggtaaactgc | 360 |
| ccacttggca gtacatcaag tgtatcatat gccaagtccg cccctattg acgtcaatga | 420 |
| cggtaaatgg cccgcctggc attatgccca gtacatgacc ttacgggact ttcctacttg | 480 |
| gcagtacatc tacgtattag tcatcgctat taccatggtg atgcggtttt ggcagtacac | 540 |
| caatgggcgt ggatagcggt ttgactcacg gggatttcca gtctccacc ccattgacgt | 600 |
| caatgggagt ttgttttggc accaaaatca acgggacttt ccaaaatgtc gtaataaccc | 660 |
| cgccccgttg acgcaaatgg gcggtaggcg tgtacggtgg gaggtctata taagcagagc | 720 |
| tggtttagtg aaccgtcaga tcactagaag ctttattgcg gtagtttatc acagttaaat | 780 |
| tgctaacgca gtcagtgctt ctgacacaac agtctcgaac ttaagctgca gaagttggtc | 840 |
| gtgaggcact gggcaggtaa gtatcaaggt tacaagacag gtttaaggag accaatagaa | 900 |
| actgggcttg tcgagacaga gaagactctt gcgtttctga taggcaccta ttggtcttac | 960 |
| tgacatccac tttgcctttc tctccacagg tgtccactcc cagttcaatt acagctctta | 1020 |
| aggctagagt attaatacga ctcactatag ggctagcaaa gcgatcgctt ccgaattcat | 1080 |
| ggtgagcaag ggcgaggagc tgttcaccgg ggtggtgccc atcctggtcg agctggacgg | 1140 |
| cgacgtaaac ggccacaagt tcagcgtgtc cggcgagggc gagggcgatg ccacctacgg | 1200 |
| caagctgacc ctgaagttca tctgcaccac cggcaagctg cccgtgccct ggcccaccct | 1260 |
| cgtgaccacc ctgacctacg gcgtgcagtg cttcagccgc taccccgacc acatgaagca | 1320 |
| gcacgacttc ttcaagtccg ccatgcccga aggctacgtc caggagcgca ccatcttctt | 1380 |
| caaggacgac ggcaactaca agacccgcgc cgaggtgaag ttcgagggcg acaccctggt | 1440 |
| gaaccgcatc gagctgaagg gcatcgactt caaggaggag ggcaacatcc tggggcacaa | 1500 |
| gctggagtac aactacaaca gccacaacgt ctatatcatg gccgacaagc agaagaacgg | 1560 |
| catcaaggtg aacttcaaga tccgccacaa catcgaggac ggcagcgtgc agctcgccga | 1620 |
| ccactaccag cagaacaccc ccatcggcga cggccccgtg ctgctgcccg acaaccacta | 1680 |
| cctgagcacc cagtccgccc tgagcaaaga ccccaacgag aagcgcgatc acatggtcct | 1740 |
| gctggagttc gtgaccgccg ccgggatcac tctcggcatg gacgagctgt acaagtctag | 1800 |
| atttgggccc aattcctgca ggcgagctct cgagccaacc actgaggatc tgtactttca | 1860 |
| gagcgataac gatggatccg aaatcggtac tggctttcca ttcgaccccc attatgtgga | 1920 |
| agtcctgggc gagcgcatgc actacgtcga tgttggtccg cgcgatggca ccctgtgct | 1980 |
| gttcctgcac ggtaacccga cctcctccta cgtgtggcgc aacatcatcc cgcatgttgc | 2040 |
| accgacccat cgctgcattg ctccagacct gatcggtatg gcaaatccg acaaaccaga | 2100 |
| cctgggttat ttcttcgacg accacgtccg cttcatggat gccttcatcg aagccctggg | 2160 |
| tctggaagag gtcgtcctgg tcattcacga ctgggggctcc gctctgggtt ccactgggc | 2220 |
| caagcgcaat ccagagcgcg tcaaaggtat tgcatttatg gagttcatcc gccctatccc | 2280 |
| gacctgggac gaatggccag aatttgcccg cgagaccttc caggccttcc gcaccaccga | 2340 |
| cgtcggccgc aagctgatca tcgatcagaa cgtttttatc gagggtacgc tgccgatggg | 2400 |
| tgtcgtccgc ccgctgactg aagtcgagat ggaccattac cgcgagccgt tcctgaatcc | 2460 |
| tgttgaccgc gagccactgt ggcgcttccc aaacgagctg ccaatcgccg gtgagccagc | 2520 |

```
gaacatcgtc gcgctggtcg aagaatacat ggactggctg caccagtccc ctgtcccgaa    2580
gctgctgttc tggggcaccc caggcgttct gatcccaccg gccgaagccg ctcgcctggc    2640
caaaagcctg cctaactgca aggctgtgga catcggcccg ggtctgaatc tgctgcaaga    2700
agacaacccg gacctgatcg gcagcgagat cgcgcgctgg ctgtctactc tggagatttc    2760
cggttaatag aattggcatg caagctgatc cggctgctaa caaagcccga aggaagctg    2820 agttggctgc tgccaccgct gagcaataac tagcataacc ccttggggcg gccgcttcga    2880
gcagacatga taagatacat tgatgagttt ggacaaacca caactagaat gcagtgaaaa    2940
aaatgcttta tttgtgaaat tgtgatgct attgctttat ttgtaaccat tataagctgc    3000
aataaacaag ttaacaacaa caattgcatt cattttatgt ttcaggttca gggggagatg    3060
tgggaggttt tttaagcaa gtaaaacctc tacaaatgtg gtaaaatcga attttaacaa    3120
aatattaacg cttacaattt cctgatgcgg tattttctcc ttacgcatct gtgcggtatt    3180
tcacaccgca tacgcggatc tgcgcagcac catggcctga ataacctct gaaagaggaa    3240 cttggttagg taccttctga ggcggaaaga accagctgtg gaatgtgtgt cagttagggt    3300
gtggaaagtc cccaggctcc ccagcaggca gaagtatgca aagcatgcat ctcaattagt    3360
cagcaaccag gtgtggaaag tccccaggct ccccagcagg cagaagtatg caaagcatgc    3420
atctcaatta gtcagcaacc atagtcccgc ccctaactcc gcccatcccg ccctaactc    3480 cgcccagttc cgcccattct ccgccccatg gctgactaat ttttttatt tatgcagagg    3540 ccgaggccgc ctcggcctct gagctattcc agaagtagtg aggaggcttt tttggaggcc    3600
taggcttttg caaaaagctt gattcttctg acacaacagt ctcgaactta aggctagagc    3660
caccatgatt gaacaagatg gattgcacgc aggttctccg gccgcttggg tggagaggct    3720
attcggctat gactgggcac aacagacaat cggctgctct gatgccgccg tgttccggct    3780
gtcagcgcag gggcgcccgg ttcttttttgt caagaccgac ctgtccggtg ccctgaatga    3840
actgcaggac gaggcagcgc ggctatcgtg gctggccacg acgggcgttc cttgcgcagc    3900
tgtgctcgac gttgtcactg aagcgggaag ggactggctg ctattgggcg aagtgccggg    3960
gcaggatctc ctgtcatctc accttgctcc tgccgagaaa gtatccatca tggctgatgc    4020
aatgcggcgg ctgcatacgc ttgatccggc tacctgccca ttcgaccacc aagcgaaaca    4080
tcgcatcgag cgagcacgta ctcggatgga agccggtctt gtcgatcagg atgatctgga    4140
cgaagagcat caggggctcg cgccagccga actgttcgcc aggctcaagg cgcgcatgcc    4200
cgacggcgag gatctcgtcg tgacccatgg cgatgcctgc ttgccgaata tcatggtgga    4260
aaatggccgc ttttctggat tcatcgactg tggccggctg ggtgtggcgg accgctatca    4320
ggacatagcg ttggctaccc gtgatattgc tgaagagctt ggcggcgaat gggctgaccg    4380
cttcctcgtg ctttacggta tcgccgctcc cgattcgcag cgcatcgcct tctatcgcct    4440
tcttgacgag ttcttctgag cgggactctg ggttcgaaa tgaccgacca agcgacgccc    4500
aacctgccat cacgatggcc gcaataaaat atctttattt tcattacatc tgtgtgttgg    4560
ttttttgtgt gaatcgatag cgataaggat cctctttgcg cttgcgtttt cccttgtcca    4620
gatagcccag tagctgacat tcatccgggg tcagcaccgt ttctgcggac tggctttcta    4680
cgtaatggtt tcttagacgt caggtggcac ttttcgggga atgtgcgcg gaacccctat    4740 ttgtttattt ttctaaatac attcaaatat gtatccgctc atgagacaat aaccctgata    4800
aatgcttcaa taatattgaa aaaggaagag tatgagtatt caacatttcc gtgtcgccct    4860
```

-continued

| | | | | | |
|---|---|---|---|---|---|
| tattcccttt | tttgcggcat | tttgccttcc | tgtttttgct | cacccagaaa | cgctggtgaa | 4920 |
| agtaaaagat | gctgaagatc | agttgggtgc | acgagtgggt | tacatcgaac | tggatctcaa | 4980 |
| cagcggtaag | atccttgaga | gttttcgccc | gaagaacgt | tttccaatga | tgagcacttt | 5040 |
| caaagttctg | ctatgtggcg | cggtattatc | ccgtattgac | gccgggcaag | agcaactcgg | 5100 |
| tcgccgcata | cactattctc | agaatgactt | ggttgagtac | tcaccagtca | cagaaaagca | 5160 |
| tcttacggat | ggcatgacag | taagagaatt | atgcagtgct | gccataacca | tgagtgataa | 5220 |
| cactgcggcc | aacttacttc | tgacaactat | cggaggaccg | aaggagctaa | ccgctttttt | 5280 |
| gcacaacatg | ggggatcatg | taactcgcct | tgatcgttgg | gaaccggagc | tgaatgaagc | 5340 |
| cataccaaac | gacgagcgtg | acaccacgat | gcctgtagca | atggcaacaa | cgttgcgcaa | 5400 |
| actattaact | ggcgaactac | ttactctagc | ttcccggcaa | caattaatag | actggatgga | 5460 |
| ggcggataaa | gttgcaggac | cacttctgcg | ctcggccctt | ccggctggct | ggtttattgc | 5520 |
| tgataaatct | ggagccggtg | agcgtgggtc | tcgcggtatc | attgcagcac | tggggccaga | 5580 |
| tggtaagccc | tcccgtatcg | tagttatcta | cacgacgggg | agtcaggcaa | ctatggatga | 5640 |
| acgaaataga | cagatcgctg | agataggtgc | ctcactgatt | aagcattggt | aattcgaaat | 5700 |
| gaccgaccaa | gcgacgccca | accggtatca | gctcactcaa | aggcggtaat | acggttatcc | 5760 |
| acagaatcag | gggataacgc | aggaaagaac | atgtgagcaa | aaggccagca | aaaggccagg | 5820 |
| aaccgtaaaa | aggccgcgtt | gctggcgttt | ttccataggc | tccgccccc | tgacgagcat | 5880 |
| cacaaaaatc | gacgctcaag | tcagaggtgg | cgaaacccga | caggactata | aagataccag | 5940 |
| gcgtttcccc | ctggaagctc | cctcgtgcgc | tctcctgttc | cgaccctgcc | gcttaccgga | 6000 |
| tacctgtccg | cctttctccc | ttcgggaagc | gtggcgcttt | ctcatagctc | acgctgtagg | 6060 |
| tatctcagtt | cggtgtaggt | cgttcgctcc | aagctgggct | gtgtgcacga | accccccgtt | 6120 |
| cagcccgacc | gctgcgcctt | atccggtaac | tatcgtcttg | agtccaaccc | ggtaagacac | 6180 |
| gacttatcgc | cactggcagc | agccactggt | aacaggatta | gcagagcgag | gtatgtaggc | 6240 |
| ggtgctacag | agttcttgaa | gtggtggcct | aactacggct | acactagaag | gacagtattt | 6300 |
| ggtatctgcg | ctctgctgaa | gccagttacc | ttcggaaaaa | gagttggtag | ctcttgatcc | 6360 |
| ggcaaacaaa | ccaccgctgg | tagcggtggt | ttttttgttt | gcaagcagca | gattacgcgc | 6420 |
| agaaaaaaag | gatttcaaga | agatcctttg | atcttttcta | cggggtctga | cgctcagtgg | 6480 |
| aacgaaaact | cacgttaagg | gattttggtc | atgagattat | caaaaaggat | cttcacctag | 6540 |
| atccttttat | agtccggaaa | tacaggaacg | cacgctggat | ggcccttcgc | tgggatggtg | 6600 |
| aaaccatgaa | aaatggcagc | ttcagtggat | taagtggggg | taatgtggcc | tgtaccctct | 6660 |
| ggttgcatag | gtattcatac | ggttaaaatt | tatcaggcgc | gattgcggca | gttttcgggt | 6720 |
| tggtttgttg | ccatttttac | ctgtctgctg | ccgtgatcgc | gctgaacgcg | ttttagcggt | 6780 |
| gcgtacaatt | aagggattat | ggtaaatcca | cttactgtct | gccctcgtag | ccatcgagat | 6840 |
| aaaccgcagt | actccggcca | cgatgcgtcc | ggcgtagagg | atcgagatct | | 6890 |

HETEROCYCLIC COMPOUND

CROSS REFERENCE TO RELATED APPLICATIONS

This application is a national phase application under 35 U.S.C. § 371 of PCT International Application No. PCT/JP2018/003576, filed Feb. 2, 2018, which claims priority to Japanese Application No. 2017-019127, filed Feb. 3, 2017, each of which are hereby incorporated by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 9,397 Byte ASCII (Text) file named "37941-252-SQL_ST25. TXT," created on Sep. 30, 2019.

TECHNICAL FIELD

The present invention relates to a compound inducing autophagic degradation of an intracellular molecule.

BACKGROUND ART

Autophagy is one of the mechanisms through which intracellular molecules are degraded in cells. This mechanism is found in eukaryotes between yeasts and humans Once autophagy is induced, membrane vesicles called autophagosomes are formed, and then the autophagosomes are fused with lysosomes so that the intracellular molecules taken up in the autophagosomes are degraded.

It is known that autophagy is induced in response to the starvation of cells. In addition, it has been getting revealed that autophagy is also involved in physiological functions such as development and differentiation, and defence mechanisms against infections such as clearance of viruses that have invaded cells.

Research has been conducted for various molecules (e.g., compounds) involved in the control of autophagic degradation of intracellular molecules. For example, Non Patent Document 1 suggests that when the following compound is added to cell cultures, the compound binds to a protein having cysteine, and the protein thus bound is taken into an autophagosome.

[Formula 1]

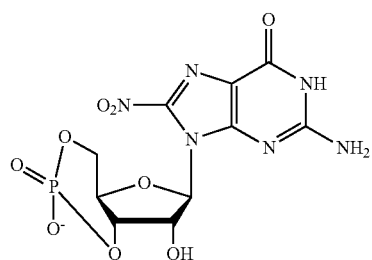

Non Patent Document 2 suggests that when the following compound is added to cells expressing halo-tagged EGFP protein, the EGFP protein is taken into an autophagosome and degraded.

[Formula 2]

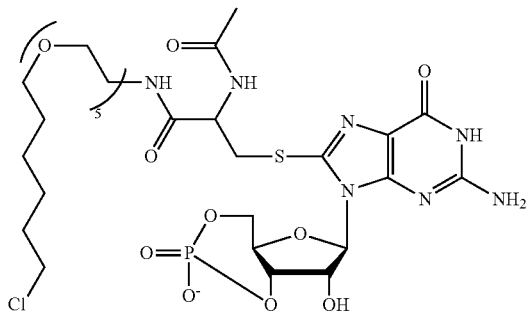

PRIOR ART DOCUMENTS

Non Patent Document

Non Patent Document 1: Mol. Cell 52 (2013) 794-804
Non Patent Document 2: "Role of S-guanylation in selective autophagy", master's thesis of the Tohoku University (release: Feb. 4, 2015)

SUMMARY OF INVENTION

Solution to Problem

The present invention provides the following compound and a medicament comprising the same.

[1]

A compound binding to an intracellular molecule and inducing autophagic degradation of the intracellular molecule, or a salt thereof, except for

[Formula 3]

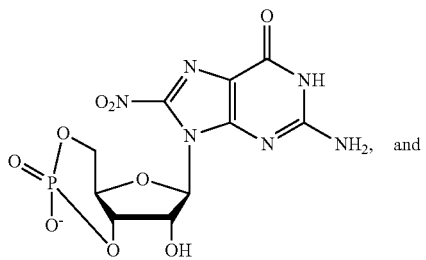

[Formula 4]

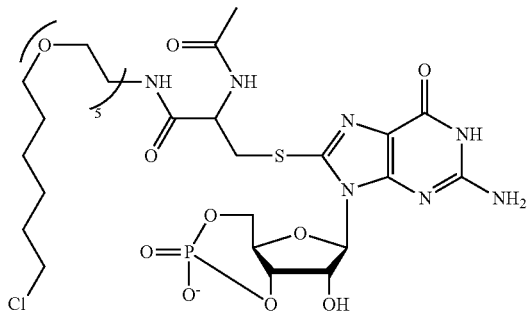

[2]
A compound represented by the following formula (I):

[Formula 5]

$$R^1-L^a-O-CH_2CH_2-O-L^b-R^2 \quad (I)$$

wherein
$R^1$ represents a ligand specifically binding to an intracellular molecule,
$L^a$ represents a bond or a chain linker having 1 to 10 atoms in a backbone,
$L^b$ represents
  i) a bond,
  ii) a chain linker having 1 to 13 atoms in a backbone, or
  iii) the following formula:

[Formula 6]

$$-L^1-X^1-L^2- \quad (II)$$

wherein $L^1$ represents a bond or a chain linker having 1 to 10 atoms in a backbone,
$X^1$ represents an optionally substituted divalent cyclic group, and
$L^2$ represents a bond or a chain linker having 1 or 2 atoms in a backbone, and $R^2$ represents a group selected from the following formulas:

[Formula 7]

(III)

(IV)

(V)

(VI)

(VII)

wherein
$R^{A1}$, $R^{A2}$, $R^{A3}$, $R^{A4}$, $R^{A5}$, $R^{A6}$, $R^{A7}$, $R^{A8}$, $R^{A9}$ and $R^{A10}$ each independently represent a hydrogen atom or a substituent, or
$R^{A1}$ and $R^{A2}$ are optionally bonded to each other to form an optionally substituted ring, and
$R^{B1}$, $R^{B2}$, $R^{B3}$, $R^{B4}$ and $R^{B5}$ each independently represent an optionally substituted hydrocarbon ring group, an optionally substituted unsaturated heterocyclic group, or the formula (VIII): $-X^2-R^3$,
wherein $X^2$ represents an optionally substituted methylene group, and $R^3$ represents an optionally substituted cyclic group,
or a salt thereof (in the present specification, the compound or the salt thereof is also referred to as "compound (I)").

[3]
The compound according to [2] or a salt thereof, wherein $R^2$ represents the following formula:

[Formula 8]

(III)

wherein
$R^{A1}$ and $R^{A2}$ each independently represent a hydrogen atom or a substituent, or
$R^{A1}$ and $R^{A2}$ are optionally bonded to each other to form an optionally substituted ring, and
$R^{B1}$ represents an optionally substituted hydrocarbon ring group, an optionally substituted unsaturated heterocyclic group, or the formula (VIII): $-X^2-R^3$ wherein
$X^2$ represents an optionally substituted methylene group, and $R^3$ represents an optionally substituted cyclic group.

[4]
A medicament comprising a compound according to any of [1] to [3] or a salt thereof.

[5]
The medicament according to [4], wherein the medicament is a drug inducing degradation of an intracellular molecule.

[6]
The medicament according to [4], wherein the medicament is a prophylactic or therapeutic drug for a cancer.

Advantageous Effects of Invention

The compound of the present invention can have the activity of binding to an intracellular molecule (in the present specification, also referred to as a "target molecule") and inducing degradation thereof and can therefore be effective for the prevention or treatment of an intracellular molecule-involving disease (e.g., a cancer).

DETAILED DESCRIPTION OF THE INVENTION

Hereinafter, the compound of the present invention, and a production method and use thereof will be described.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ arylcarbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ acylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{746}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl)amino group (e.g., methylcarbamoylamino), a (mono- or di-$C_{746}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl)($C_{1-6}$ alkyl-carbonyl)amino group (e.g., N-acetyl-N-methylamino) and a ($C_{1-6}$ alkyl)($C_{6-14}$ aryl-carbonyl)amino group (e.g., N-benzoyl-N-methylamino)

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{340}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ arylcarbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocylyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "$C_{1-6}$ alkylene group" include —$CH_2$—, —$(CH_2)_2$—, —$(CH_2)_3$—, —$(CH_2)_4$—, —$(CH_2)_5$—, —$(CH_2)_6$—, —CH($CH_3$)—, —C($CH_3$)$_2$—, —CH($C_2H_5$)—, —CH($C_3H_7$)—, —CH(CH($CH_3$)$_2$)—, —(CH($CH_3$))$_2$—, —$CH_2$—CH($CH_3$)—, —CH($CH_3$)—$CH_2$—, —$CH_2$—$CH_2$—C($CH_3$)$_2$—, —C($CH_3$)$_2$—$CH_2$—$CH_2$—, —$CH_2$—$CH_2$—$CH_2$—C($CH_3$)$_2$— and —C($CH_3$)$_2$—$CH_2$—$CH_2$—$CH_2$—.

In the present specification, examples of the "$C_{2-6}$ alkenylene group" include —CH=CH—, —$CH_2$—CH=CH—, —CH=CH—$CH_2$—, —C($CH_3$)$_2$—CH=CH—, —CH=CH—C($CH_3$)$_2$—, —$CH_2$—CH=CH—$CH_2$—, —$CH_2$—$CH_2$—CH=CH—, —CH=CH—$CH_2$—$CH_2$—, —CH=CH—CH=CH—, —CH=CH—$CH_2$—$CH_2$—$CH_2$— and —$CH_2$—$CH_2$—$CH_2$—CH=CH—.

In the present specification, examples of the "$C_{2-6}$ alkynylene group" include —C≡C—, —$CH_2$—C≡C—, —C≡C—$CH_2$—, —C($CH_3$)$_2$—C≡C—, —C≡C—C($CH_3$)$_2$—, —$CH_2$—C≡C—$CH_2$—, —$CH_2$—$CH_2$—C≡C—, —C≡C—$CH_2$—$CH_2$—, —C≡C—C≡C—, —C≡C—$CH_2$—$CH_2$—$CH_2$— and —$CH_2$—$CH_2$—$CH_2$—C≡C—.

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and
9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "cyclic group" include $C_{3-10}$ cycloalkyl groups, $C_{3-10}$ cycloalkenyl groups, and $C_{6-14}$ aryl groups.

In the present specification, examples of the "$C_{1-12}$ alkoxy group" include $C_{1-6}$ alkoxy groups.

In the present specification, examples of the "unsaturated heterocyclic group" include a "heterocyclic group" having at least one unsaturated bond.

Hereinafter, the terms used in the present specification will be defined.

In the present specification, the "intracellular molecule" means a biomolecule, at least a portion of which is present in a cell. Examples of the "intracellular molecule" include lipids, glycolipids, proteins, and glycoproteins present in cells, typically proteins present in cells. The "intracellular molecule" is not particularly limited by cell types. The cell is preferably of a mammal (e.g., mice, rats, hamsters, rabbits, cats, dogs, cattle, sheep, monkeys, and humans), and a human cell is most practically kept in mind. Examples of the intracellular protein include intracellular proteins related to pathological conditions (particularly, intracellular proteins related to human pathological conditions) as practical targets. Examples of the pathological condition-related intracellular protein include BRD4, Ras, FKBP12 and MetAP2.

In the present specification, the "ligand specifically binding to an intracellular molecule" means a structural unit that constitutes a portion of the compound of the present invention, typically, compound (I), and has activity specifically binding to a molecule (e.g., proteins) present in a cell of an organism (in the present specification, also referred to as "ligand activity to an intracellular molecule"). The substance constituting the structural unit can be any substance specifically binding to the intracellular molecule. Examples thereof include DNA, RNA, nucleosides, nucleotides, proteins, peptides, amino acids, lipids, alkaloids, terpenes and their derivatives, coenzymes, and low-molecular compounds (particularly, low-molecular organic compounds).

In the present specification, the "linker" means a group of atoms through which the "ligand" moiety and an autophagy-inducing moiety in the compound of the present invention are linked, and, in compound (I), means the whole or a portion of a structure of the formula: —La—O—C—C—O-Lb- through which $R^1$ and $R^2$ are linked.

A structural unit consisting of a ligand and a linker bonded to the ligand, which constitutes a portion of the compound of the present invention, can have ligand activity to an intracellular molecule.

A preferred embodiment of the compound of the present invention is compound (I), which will be described below.

$R^1$ in the formula (I) represents a ligand specifically binding to an intracellular molecule (e.g., intracellular proteins). The intracellular molecule refers to a molecule present in a cell and includes endogenous molecules, exogenous molecules and molecules (e.g., proteins) intracellularly expressed on the basis of exogenous molecules (e.g., protein expression vectors) artificially introduced into cells. Examples of the intracellular molecule include intracellular proteins fused with HaloTag®, and intracellular proteins related to pathological conditions.

Examples of the intracellular protein of the "intracellular protein fused with HaloTag" include EGFP and EmGFP.

Examples of the intracellular protein related to a pathological condition include ligands specifically binding to BRD4 (involved in multiple myeloma, acute myeloid leukemia, and the like), Ras (involved in colorectal cancer, pancreatic cancer, and the like), FKBP12 and MetAP2.

$R^1$ is more preferably a ligand for an intracellular protein of EmGFP fused with HaloTag, or a ligand specifically binding to BRD4, Ras, FKBP12 or MetAP2.

Examples of the ligand for BRD4 include

[Formula 9]

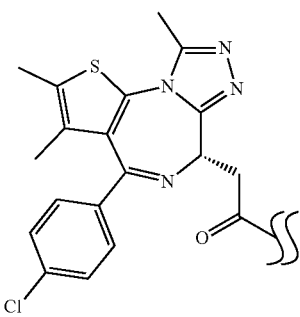

Examples of the ligand for FKBP12 include

[Formula 10]

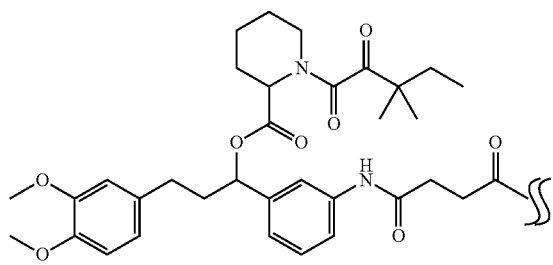

Examples of the ligand for MetAP2 include

[Formula 11]

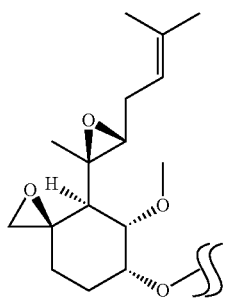

Examples of the ligand for Ras include ligands described in the following documents: Nature, 2013, 503, 548-551; International Publication No. WO2013/155223; Science, 2016, 351, 604-608; International Publication No. WO2014152588; International Publication No. WO2015/054572; International Publication No. WO2016/049524; Nat. Rev. Drug Discov., 2014, 13, 828-851; and Chem. Soc. Rev., 2016, advance article (DOI: 10.1039/C5CS00911A).

Examples of the ligand for Ras include

[Formula 12]

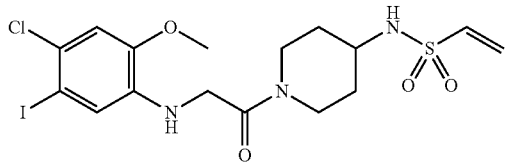

[Formula 13]

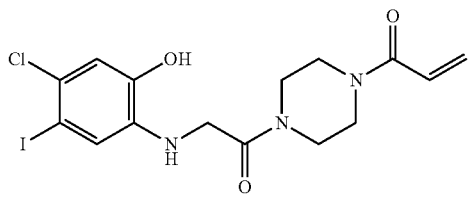

[Formula 14]

[Formula 15]

[Formula 16]

Examples of the ligand for an intracellular protein fused with HaloTag® include halogenated $C_{1-12}$ alkoxy groups (particularly, terminal carbon-halogenated $C_{1-6}$ alkoxy groups), preferably a halogenated (particularly, terminal carbon-halogenated) hexyloxy group (particularly, a chlorinated hexyloxy group).

-$L^a$-O—$CH_2$—$CH_2$—O-$L^b$-in the formula (I) represents a linker that links the ligand specifically binding to an intracellular molecule, represented by IV to a structure represented by $R^2$ that causes autophagy.

$L^a$ represents a bond or a chain linker having 1 to 10 atoms in a backbone.

Examples of the atoms constituting the chain linker include unsubstituted atoms selected from the group consisting of a carbon atom, an oxygen atom, a nitrogen atom and a sulfur atom. The bond between the atoms may be any of a single bond, a double bond and a triple bond. The chain linker can be constituted by any one or more moieties selected from, for example, —$CH_2$—, —CH═, ═CH—, —C≡, ≡C—, —NH—, —N═, ═N—, —O—, —S—, —C(O)—, —C(S)—, —C(NH)— and —CH═N—, which may each be optionally substituted by a halogen atom at a substitutable position.

$L^a$ is preferably a $C_{1-6}$ alkylene group (particularly, an ethylene group) or a -optionally substituted nitrogen atom-$C_{1-6}$ alkylene group (particularly, a —NH-ethylene group).

$L^b$ represents
i) a bond;
ii) a chain linker having 1 to 13 atoms in a backbone, or
iii) the following formula (II);

[Formula 17]

$$-L^1-X^1-L^2-  \quad (II)$$

The chain linker ii) may be a branched chain or a linear chain. Examples of the atoms constituting the chain linker include unsubstituted atoms selected from the group consisting of a carbon atom, an oxygen atom, a nitrogen atom and a sulfur atom. The bond between the atoms may be any of a single bond, a double bond and a triple bond. The chain linker can be constituted by one or more moieties selected from the group consisting of, for example, —CH$_2$—, —CH=, =CH—, —C≡, ≡C—, —NH—, —N=, =N—, —O—, —S—, —C(O)—, —C(S)—, —CH$_2$(NH)—, —CO(NH)— and —CH=N—, which may each be optionally substituted by a halogen atom at a substitutable position.

The chain linker ii) is preferably represented by the following formula:

$$-(C_x \text{ alkylene-O})_{n1}-(CH_2)_{m1}-B_1- \quad (IX)$$

wherein
x is 1 to 6, preferably 2 or 3,
n1 is 1 to 5, preferably 1 to 3,
m1 is 0 to 5, preferably 1 to 3, more preferably 2 or 3, particularly preferably 2, and
$B_1$ is
(i) a bond,
(ii) —NH—,
(iii) —NH—(CO)—B$_2$— wherein B$_2$ represents a bond, —C$_{1-3}$ alkylene-NH (particularly, -methylene-NH or -ethylene-NH), —C$_{1-3}$ alkylene-S— (particularly, methylene-S— or ethylene-S—), or a C$_{2-3}$ alkenylene group (particularly, a vinylene group),
(iv) a C$_{2-3}$ alkynylene group (particularly, an acetylene group),
(v) a —NH—C$_{1-3}$ alkylene group (particularly, a —NH-methylene group), or
(vi) —N—C$_{1-6}$ alkyl-carbonyl-L-cysteinamide (particularly, —N2 acetyl-L-cysteinamide),
preferably
(i) —NH—,
(ii) —CO(NH)—,
(iii) a —NH—(CO)—C$_{2-3}$ alkenylene group (particularly, a —NH—(CO)-vinylene group)),
(iv) a —NH—C$_{1-3}$ alkylene group (particularly, a —NH-methylene group), or
(v) —N—C$_{1-6}$ alkyl-carbonyl-L-cysteinamide (particularly, —N2 acetyl-L-cysteinamide).
Preferred examples of $B_1$ include substituents of

[Formula 18]

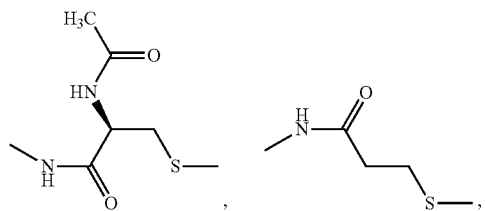

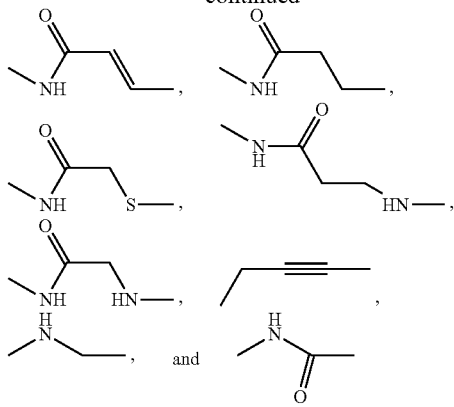

More preferred examples of $B_1$ include substituents of

[Formula 19]

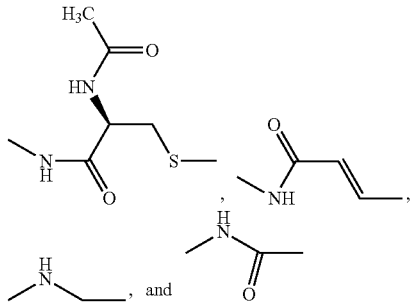

$L^1$ in the formula (II) represents a bond or a chain linker having 1 to 10 atoms in a backbone. Examples of the atoms constituting this chain linker include unsubstituted atoms selected from the group consisting of a carbon atom, an oxygen atom, a nitrogen atom and a sulfur atom. The bond between the atoms may be any of a single bond, a double bond and a triple bond. The chain linker can be constituted by one or more moieties selected from the group consisting of, for example, —CH$_2$—, —CH=, =CH—, —C≡, ≡C—, —NH—, —N=, =N—, —O—, —S—, —C(O)—, —C(S)—, —C(NH)— and —CH=N—, which may each be optionally substituted by a halogen atom at a substitutable position.

$L^1$ is preferably represented by the following formula:

$$-(C_y \text{ alkylene-O})_{n2}-(CH_2)_{m2}- \quad (X)\text{ or}$$

$$-(C_y \text{ alkylene-NH})_{n2}-(CH_2)_{m2}- \quad (X')$$

wherein
y is 1 to 3, preferably 2 or 3,
n2 is 1 to 6, preferably 1 to 3, and
m2 is 0 to 3, preferably 0 to 2.
$L_1$ is more preferably -(ethylene-O)$_{n2'}$—(CH$_2$)$_{m2'}$— or -(propylene-O)$_{n2'}$—(CH$_2$)$_{m2'}$ wherein n2' is 1 to 3, and m2' is 0 to 2, further preferably -(ethylene-O)$_{n2''}$—(CH$_2$)$_{m2''}$ wherein n2" is 1 or 2, and m2" is 1 or 2.

$X^1$ in the formula (II) represents an optionally substituted divalent cyclic group. Examples of the divalent cyclic group include optionally substituted divalent C$_{6-14}$ aromatic carbocyclic groups (particularly, optionally substituted divalent 5- or 6-membered aromatic carbocyclic groups (particularly, a phenylene group substituted by an amide group or an unsubstituted phenylene group)), optionally substituted divalent 5- to 14-membered aromatic heterocyclic groups (particularly, optionally substituted divalent 5- or 6-membered aromatic heterocyclic groups (particularly, a pyrazolyl ring or triazolyl)), and optionally substituted divalent 3- to 14-membered nonaromatic heterocyclic groups (particularly, optionally substituted divalent 6-membered nonaromatic heterocyclic groups (particularly, piperidinyl substituted by an amide group)).

A compound of the formula (I) wherein -$L^a$-O—$CH_2$—$CH_2$—O-$L^b$- is replaced with -$L^a$-O—$(CH_2)_{n'}$—O-$L^b$- wherein n' represents 1 or 3 to 6, or -$L^a$-NH—$(CH_2)_{n''}$—NH-$L^b$- wherein n" represents 1 to 6 has the desired effect. Of such compounds, preferable is a compound in which the moiety is replaced with -$L^a$-O-propylene-O-$L^b$-, -$L^a$-NH-ethylene-NH— or -$L^a$-NH-propylene-NH-$L^b$-.

$X^1$ is preferably an optionally substituted divalent 5- or 6-membered aromatic carbocyclic ring (particularly, a phenylene group substituted by an amide group or an unsubstituted phenylene group), an optionally substituted divalent 5- or 6-membered aromatic heterocyclic ring (particularly, a pyrazole ring or a triazole ring), or an optionally substituted divalent 6-membered nonaromatic heterocyclic ring (particularly, a piperidine ring substituted by an amide group), more preferably an optionally substituted divalent 5- or 6-membered aromatic carbocyclic ring (particularly, a phenylene group substituted by an amide group).

$L^2$ in the formula (II) represents a bond or a chain linker having 1 or 2 atoms in a backbone. Examples of the atoms constituting the chain linker include unsubstituted atoms selected from the group consisting of a carbon atom, an oxygen atom, a nitrogen atom and a sulfur atom. When the number of atoms is 2, the bond between the atoms may be any of a single bond, a double bond and a triple bond. $L^2$ is preferably a bond or a carbonyl group (particularly, a carbonyl group bonded to a heteroatom (particularly, a nitrogen atom) of a heterocyclic ring).

Preferred examples of —$X_1$-$L_2$-include

[Formula 20]

A preferred form of $L^b$ is
i) represented by the formula:

$$—(C_x \text{ alkylene-O})_{n1}—(CH_2)_{m1}—B_1 \quad (IX)$$

wherein
x is 2 or 3 (preferably 2),
n1 is 1 to 3 (preferably 2 or 3),
m1 is 1 to 3 (preferably 1), and
$B_1$ is
(i) a bond,
(ii) —NH—,
(iii) —NH—(CO)—$B_2$— wherein $B_2$ represents a bond, —$C_{1-3}$ alkylene-NH (particularly, -methylene-NH or -ethylene-NH), —$C_{1-3}$ alkylene-S— (particularly, methylene-S— or ethylene-S—), or a $C_{2-3}$ alkenylene group (particularly, a vinylene group),
(v) a $C_{2-3}$ alkynylene group (particularly, an acetylene group),
(vi) a —NH—$C_{1-3}$ alkylene group (particularly, a —NH-methylene group), or
(vii) —N—$C_{1-6}$ alkyl-carbonyl-L-cysteinamide (particularly, —N2 acetyl-L-cysteinamide); or
ii) represented by the formula:

[Formula 21]

$$-L^1-X^1-L^2- \quad (II)$$

wherein
$L^1$ is represented by the following formula:

$$—(C_y \text{ alkylene-O})_{n2}—(CH_2)_{m2}— \quad (X), \text{ or}$$

$$—(C_y \text{ alkylene-NH})_{n2}—(CH_2)_{m2}— \quad (X')$$

wherein
y is 2 or 3 (preferably 2),
n2 is 1 to 6 (preferably 1 to 3), and
m2 is 0 to 3 (preferably 0 to 2)),
$L^1$ is preferably -(ethylene-O)$_{n2'}$—(CH$_2$)$_{m2'}$— or -(propylene-O)$_{n2'}$—(CH$_2$)$_{m2'}$— wherein n2' is 1 to 3, and m2' is 0 to 2,
$X^1$ is an optionally substituted divalent 5- or 6-membered aromatic carbocyclic group (particularly, a phenylene group substituted by an amide group or an unsubstituted phenylene group), an optionally substituted divalent 5- or 6-membered aromatic heterocyclic group (particularly, a pyrazolyl ring or a triazolyl ring), or an optionally substituted divalent 6-membered nonaromatic heterocyclic group (particularly, piperidinyl substituted by an amide group), and
$L^2$ is a bond or a carbonyl group (particularly, a carbonyl group bonded to a heteroatom (particularly, a nitrogen atom) of a heterocyclic ring).
$L^b$ is more preferably
i) a chain linker represented by the formula:

$$-(\text{ethylene-O})_{n1}—(CH_2)_{m1}—B_1 \quad (IX')$$

wherein
n1 is 1 or 2,
m1 is 1, and
$B_1$ is
(i) —NH—,
(ii) —NH—(CO)—,
(iii) —NH—(CO)-ethylene,
(iv) a —NH—$C_{1-3}$ alkylene group (particularly, an aminomethylene group), or
(v) —N2 acetyl-L-cysteinamide, or
ii) represented by the formula:

[Formula 22]

$$-L^1-X^1-L^2- \quad (II)$$

wherein
$L^1$ is -(ethylene-O)$_{n2}$—(CH$_2$)$_{m2}$— wherein n2 is 1 to 3, and m2 is 0 or 1, $X^1$ is a phenylene group substituted by an amide group, and $L^2$ is a bond.

$R^2$ represents a group selected from the following formulas:

[Formula 23]

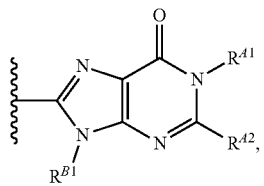
(III)

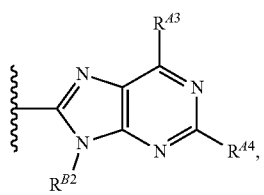
(IV)

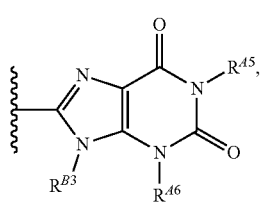
(V)

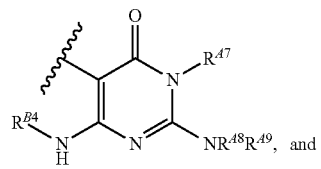
(VI)

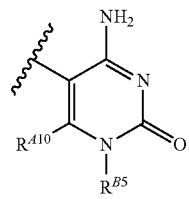
(VII)

wherein $R^{A1}$, $R^{A2}$, $R^{A3}$, $R^{A4}$, $R^{A5}$, $R^{A6}$, $R^{A7}$, $R^{A8}$, $R^{A9}$ and $R^{A10}$ each independently represent a hydrogen atom or a substituent, or $R^{A1}$ and $R^{A2}$ are optionally bonded to each other to form an optionally substituted ring, and $R^{B1}$, $R^{B2}$, $R^{B3}$, $R^{B4}$ and $R^{B5}$ each independently represent an optionally substituted hydrocarbon ring group, an optionally substituted unsaturated heterocyclic group, or the formula (VIII): —$X^2$—$R^3$ wherein $X^2$ represents an optionally substituted methylene group, and $R^3$ represents an optionally substituted cyclic group.

$R^2$ is preferably a group represented by the formula (III), (IV) or (V), more preferably a group represented by the formula (III).

$R^{A1}$, $R^{A2}$, $R^{A3}$, $R^{A4}$, $R^{A5}$, $R^{A6}$, $R^{A7}$, $R^{A8}$, $R^{A9}$ and $R^{A10}$ are, preferably, each independently a hydrogen atom, an optionally substituted amino group (particularly, an unsubstituted amino group or an amino group substituted by $C_{1-6}$ alkyl-carbonyl group (particularly, a methylcarbonyl group)), or a $C_{1-6}$ alkyl group (particularly, a methyl group), more preferably a hydrogen atom, an unsubstituted amino group), or a $C_{1-3}$ alkyl group (particularly, a methyl group).

When $R^{A1}$ and $R^{A2}$ are bonded to each other to form a ring, the ring to be formed is preferably an optionally substituted 5- or 6-membered aromatic heterocyclic ring condensed with a 6-membered ring of purine (particularly, a condensed imidazole ring).

$R^{B1}$, $R^{B2}$, $R^{B3}$, $R^{B4}$ and $R^{B5}$ each independently represent an optionally substituted hydrocarbon ring group, an optionally substituted unsaturated heterocyclic group, or the formula (VIII): —$X^2$—$R^3$ wherein $X^2$ represents an optionally substituted methylene group, and $R^3$ represents an optionally substituted cyclic group.

$R^{B1}$, $R^{B2}$, $R^{B3}$, $R^{B4}$ and $R^{B5}$ are, preferably, each independently (i) an optionally substituted $C_{3-10}$ cycloalkyl group (particularly, a cyclopentyl group or a cyclohexyl group), (ii) an optionally substituted $C_{6-14}$ aryl group (particularly, a phenyl group), (iii) an optionally substituted 5- or 6-membered nonaromatic heterocyclic group (particularly, ribose), (iv) a methylene group substituted by a $C_{6-14}$ aryl group (particularly, a benzyl group), (v) a methylene group substituted by a halogenated $C_{6-14}$ aryl group (particularly, a benzyl group substituted by fluorine or chlorine at a para, meta or ortho position), (vi) a methylene group substituted by a $C_{6-14}$ aryl group substituted by one to three cyano groups (particularly, a benzyl group substituted by one cyano group), (vii) a methylene group substituted by a $C_{6-14}$ aryl group substituted by one to three $C_{1-6}$ alkyl groups (particularly, a benzyl group substituted by one $C_{1-6}$ alkyl group (particularly, methyl group)), (viii) a methylene group substituted by a $C_{6-14}$ aryl group substituted by one to three $C_{1-6}$ alkoxy groups (particularly, a benzyl group substituted by one methoxy group), (ix) a methylene group substituted by a $C_{6-14}$ aryl group substituted by one to three $C_{1-6}$ alkylsulfonyl groups (particularly, a benzyl group substituted by a methylsulfonyl group), (x) a methylene group substituted by a 5- or 6-membered aromatic heterocyclic group optionally substituted by one to three $C_{1-6}$ alkyl groups (particularly, methylene substituted by a pyridyl group, a thiazole group, or a pyrazole group substituted by one to three substituents (particularly, methyl group) selected from $C_{1-6}$ alkyl groups), or (xi) a methylene group substituted by a 5- to 14-membered nonaromatic heterocyclic group (particularly, a methylene group substituted by a 5- or 6-membered nonaromatic heterocyclic group (particularly, methylene substituted by a tetrahydropyranyl group)).

Each of $R^{B1}$, $R^{B2}$, $R^{B3}$, $R^{B4}$ and $R^{B5}$ is more preferably (i) an optionally substituted 5- or 6-membered nonaromatic heterocyclic group (particularly, ribose), (ii) a methylene group substituted by a halogenated $C_{6-14}$ aryl group (particularly, a benzyl group substituted by fluorine or chlorine), or a methylene group substituted by a $C_{6-14}$ aryl group substituted by a $C_{1-6}$ alkyl group (particularly, a benzyl group substituted by a $C_{1-6}$ alkyl group (particularly, a methyl group)).

Each of $R^{B1}$, $R^{B2}$, $R^{B3}$, $R^{B4}$ and $R^{B5}$ may be an optionally substituted saturated heterocyclic group (particularly, cyclohexyl or (4aR,6R,7R,7aS)-2,7-dihydroxy-2-oxidotetrahydro-4H-furo[3,2-d][1,3,2]dioxaphosphinine) Such a compound or a salt thereof is also included in the compound binding to an intracellular molecule and inducing autophagic degradation of the intracellular molecule, or a salt thereof.
Preferred examples of R² include substituents of
[Formula 24-1]
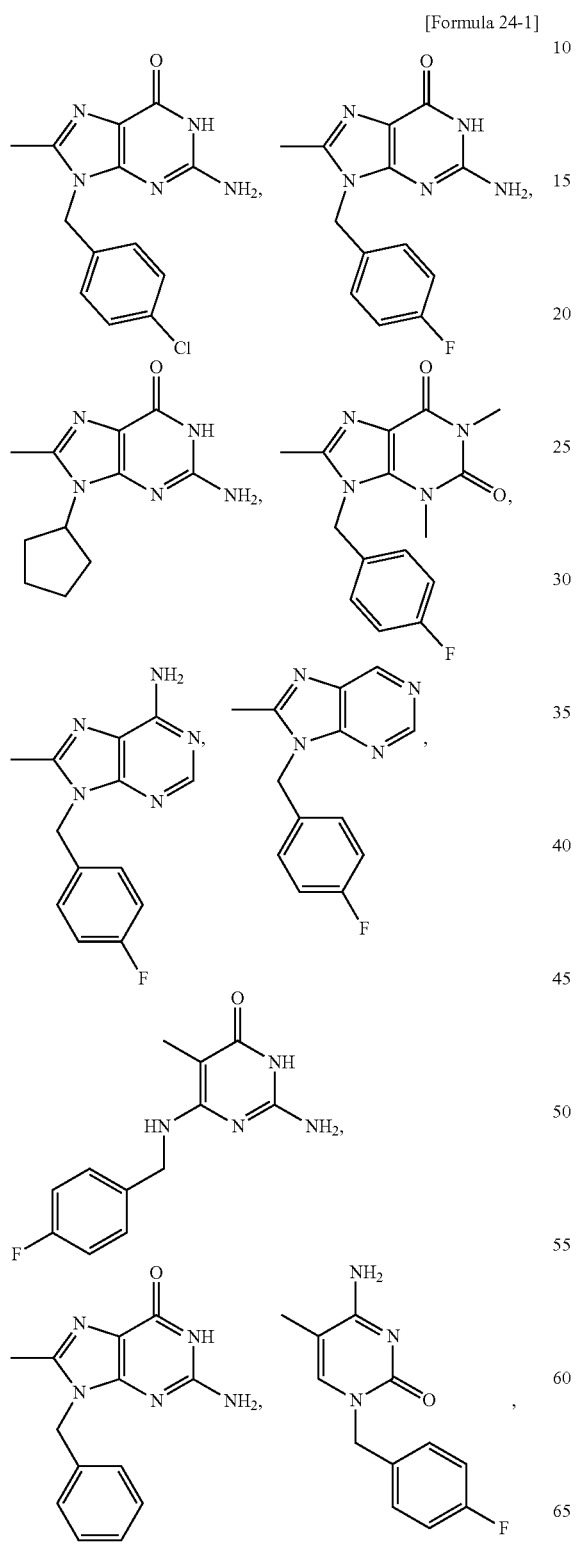
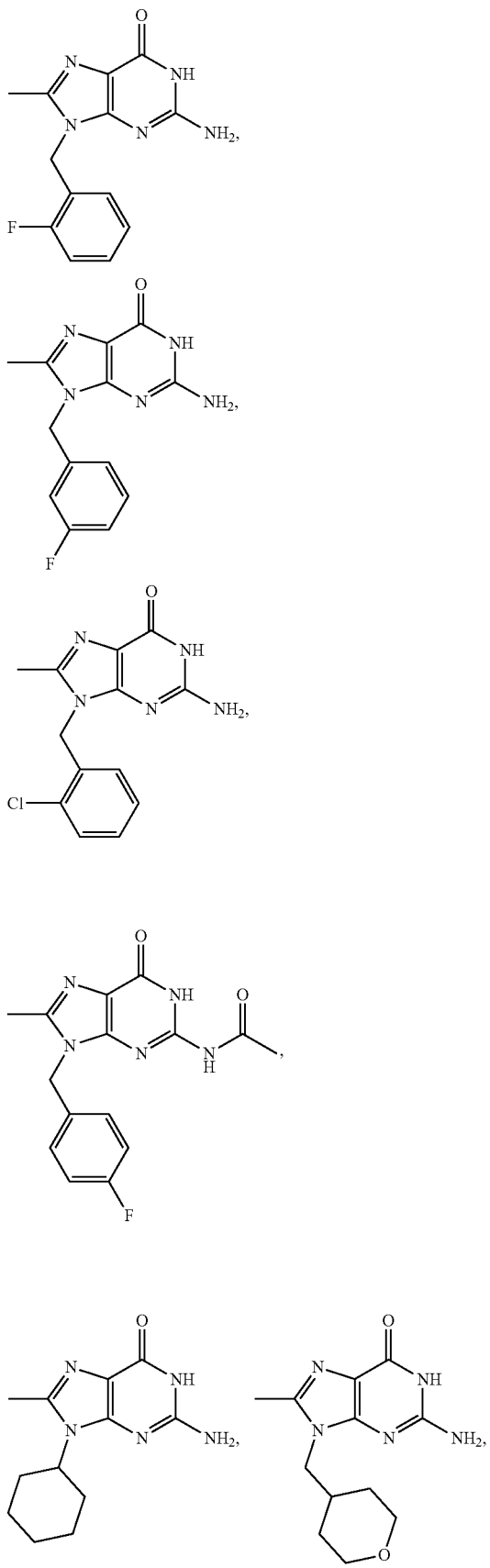

-continued
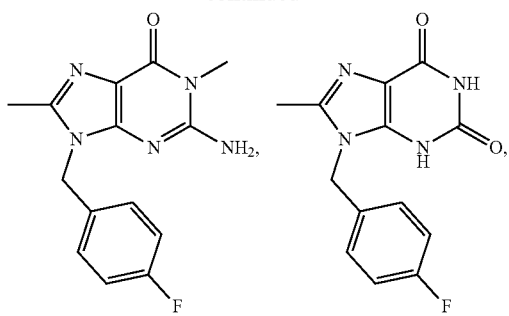
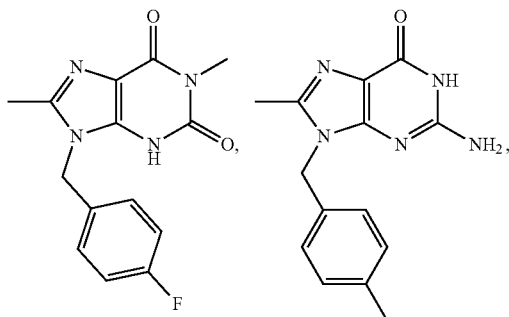
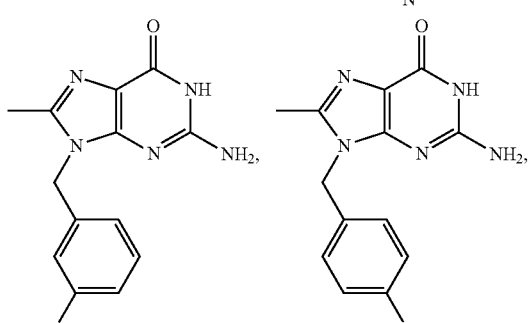
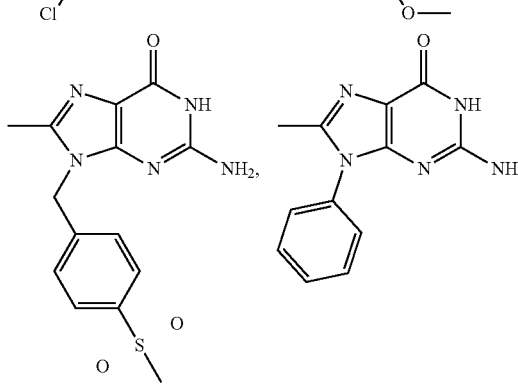
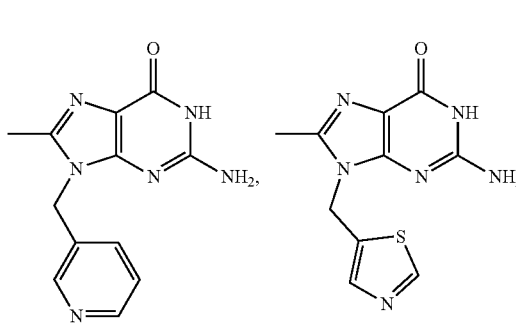
-continued
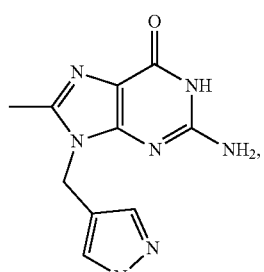
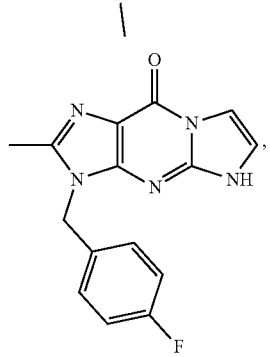
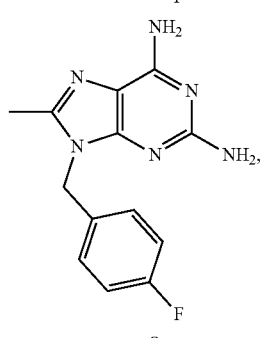
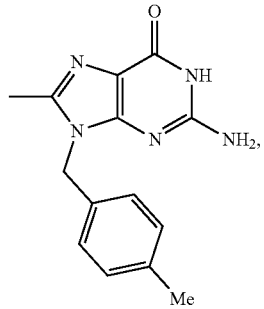
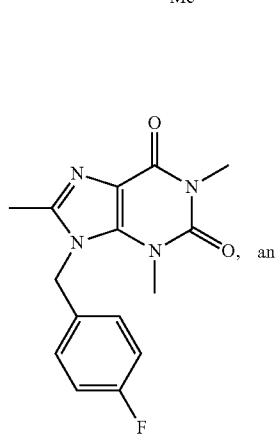
[Formula 24-2]

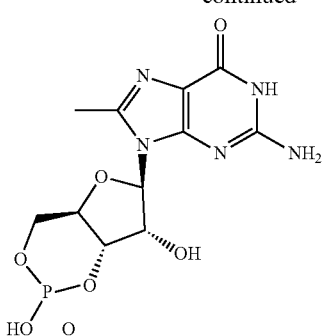

More preferred examples thereof include

[Formula 25]

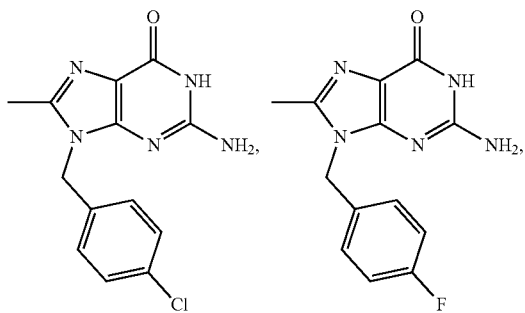

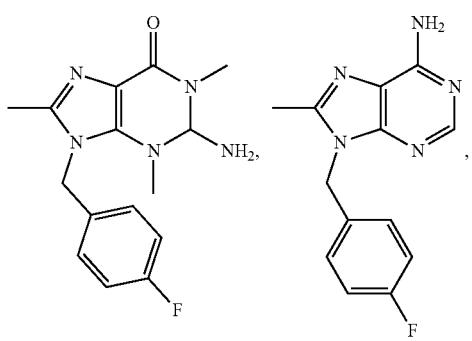

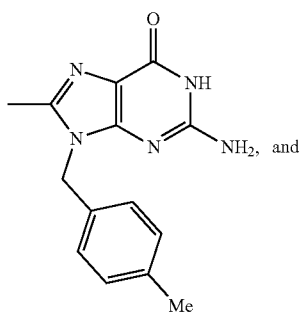

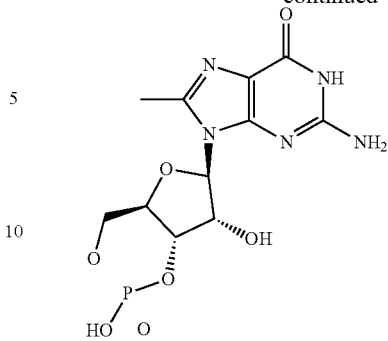

When $R^2$ is a group of the formula (III), $R^{A1}$ and $R^{A2}$ are, preferably, each independently a hydrogen atom, an optionally substituted amino group (particularly, an unsubstituted amino group or an amino group substituted by a $C_{1-6}$ alkylcarbonyl group (particularly, a methylcarbonyl group)), or a $C_{1-6}$ alkyl group (particularly, a methyl group). More preferably, $R^{A1}$ is a hydrogen atom or a $C_{1-6}$ alkyl group (particularly, a methyl group), and $R^{A2}$ is a hydrogen atom, an optionally substituted amino group (particularly, an unsubstituted amino group or an amino group substituted by a $C_{1-6}$ alkylcarbonyl group (particularly, a methylcarbonyl group)), or a $C_{1-6}$ alkyl group (particularly, a methyl group).

When $R^{A1}$ and $R^{A2}$ are bonded to each other to form a ring, the ring to be formed is preferably an optionally substituted 5- or 6-membered condensed aromatic heterocyclic ring (particularly, a condensed imidazole ring).

$R^{B1}$ is preferably
(i) an optionally substituted $C_{3-10}$ cycloalkyl group (particularly, a cyclopentyl group or a cyclohexyl group),
(ii) an optionally substituted $C_{6-14}$ aryl group (particularly, a phenyl group),
(iii) an optionally substituted 5- or 6-membered nonaromatic heterocyclic group (particularly, ribose),
(iv) a methylene group substituted by a $C_{6-14}$ aryl group (particularly, a benzyl group),
(v) a methylene group substituted by a halogenated $C_{6-14}$ aryl group (particularly, a benzyl group substituted by fluorine or chlorine at a para, meta or ortho position),
(vi) a methylene group substituted by a $C_{6-14}$ aryl group substituted by one to three cyano groups (particularly, benzyl substituted by one cyano group),
(vii) a methylene group substituted by a $C_{6-14}$ aryl group substituted by one to three $C_{1-6}$ alkyl groups (particularly, benzyl substituted by one $C_{1-6}$ alkyl group (particularly, methyl group)),
(viii) a methylene group substituted by a $C_{6-14}$ aryl group substituted by one to three $C_{1-6}$ alkoxy groups (particularly, benzyl substituted by one methoxy group),
(ix) a methylene group substituted by a $C_{6-14}$ aryl group substituted by one to three $C_{1-6}$ alkylsulfonyl groups (particularly, benzyl substituted by a methylsulfonyl group),
(x) a methylene group substituted by a 5- or 6-membered aromatic heterocyclic group optionally substituted by one to three $C_{1-6}$ alkyl groups (particularly, a methylene group substituted by a pyridyl group, a thiazole group, or a pyrazole group substituted by one to three substituents selected from $C_{1-6}$ alkyl groups (particularly, methyl group)), or
(xi) a methylene group substituted by a 5- to 14-membered nonaromatic heterocyclic group (particularly, a methylene group substituted by a 5- or 6-membered nonaromatic heterocyclic group (particularly, a tetrahydropyranyl group)).

When $R^2$ is a group of the formula (IV), $R^{43}$ and $R^{44}$ are, preferably, each independently a hydrogen atom or an optionally substituted amino group (particularly, an unsubstituted amino group).

$R^{B2}$ is preferably a methylene group substituted by a halogenated $C_{6-14}$ aryl group (particularly, a benzyl group substituted by fluorine or chlorine).

When $R^2$ is a group of the formula (V), $R^{45}$ and $R^{46}$ are preferably, each independently a hydrogen atom or a $C_{1-6}$ alkyl group (particularly, a methyl group).

$R^{B3}$ is preferably a methylene group substituted by a halogenated $C_{6-14}$ aryl group (particularly, a benzyl group substituted by fluorine or chlorine).

When $R^2$ is a group of the formula (VI), each of $R^{47}$, $R^{48}$, and $R^{49}$ is preferably a hydrogen atom.

$R^{B4}$ is preferably a methylene group substituted by a halogenated $C_{6-14}$ aryl group (particularly, a benzyl group substituted by fluorine or chlorine).

When $R^2$ is a group of the formula (VII), $R^{410}$ is preferably a hydrogen atom.

$R^{B5}$ is preferably a methylene group substituted by a halogenated $C_{6-14}$ aryl group (particularly, a benzyl group substituted by fluorine or chlorine).

$R^2$ is preferably a group selected from the formulas (III), (IV), and (V), wherein:
when $R^2$ is a group of the formula (III),
$R^{41}$ is a hydrogen atom,
$R^{42}$ is an optionally substituted amino group (particularly, an unsubstituted amino group), and
$R^{B1}$ is
(i) an optionally substituted 5- or 6-membered nonaromatic heterocyclic group (particularly, ribose),
(ii) a methylene group substituted by a halogenated $C_{6-14}$ aryl group (particularly, a benzyl group substituted by fluorine or chlorine), or
(iii) a methylene group substituted by a $C_{6-14}$ aryl group substituted by a $C_{1-6}$ alkyl group (particularly, a benzyl group substituted by a $C_{1-6}$ alkyl group (particularly, a methyl group));
when $R^2$ is a group of the formula (IV),
$R^{43}$ is an optionally substituted amino group (particularly, an unsubstituted amino group),
$R^{44}$ is a hydrogen atom, and
$R^{B2}$ is a methylene group substituted by a halogenated $C_{6-14}$ aryl group (particularly, a benzyl group substituted by fluorine or chlorine); and
when $R^2$ is a group of the formula (V),
$R^{45}$ and $R^{46}$ are each independently
(i) a hydrogen atom, or
(ii) a $C_{1-6}$ alkyl group (particularly, a methyl group), and
$R^{B3}$ is a methylene group substituted by a halogenated $C_{6-14}$ aryl group (particularly, a benzyl group substituted by fluorine or chlorine).

Preferred specific examples of the compound (I) include the following: Compound (A): a compound (I) wherein
$R^1$ is a ligand specifically binding to an intracellular protein fused with HaloTag, BRD4, Ras, FKBP12 or MetAP2;

$L^a$ is a $C_{1-6}$ alkylene group (particularly, an ethylene group) or a —NH—$C_{1-6}$ alkylene group (particularly, a —NH-ethylene group);
$L^b$ is a linker
i) represented by the formula:

$$—(C_x \text{ alkylene-O})_{n1}—(CH_2)_{m1}—B_1 \qquad (IX)$$

wherein
x is 2 or 3 (preferably 2),
n1 is 1 to 3 (preferably 2 or 3),
m1 is 1 to 3 (preferably 1), and
$B_1$ is
(i) a bond,
(ii) —NH—,
(iii) —NH—(CO)—$B_2$— wherein $B_2$ represents a bond, —$C_{1-3}$ alkylene-NH— (particularly, -methylene-NH— or -ethylene-NH—), alkylene-S— (particularly, -methylene-S— or -ethylene-S—), or a $C_{2-3}$ alkenylene group (particularly, a vinylene group),
(v) a —$C_{2-3}$ alkynylene group (particularly, an acetylene group),
(vi) a —NH—$C_{1-3}$ alkylene group (particularly, a —NH-methylene group), or
(vii) a —N—$C_{1-6}$ alkyl-carbonyl-L-cysteinamide (particularly, —N2 acetyl-L-cysteinamide); or
ii) represented by the formula:

[Formula 26]

$$-L^1-X^1-L^2- \qquad (II)$$

wherein
$L^1$ is represented by the following formula:

$$—(C_y \text{ alkylene-O})_{n2}—(CH_2)_{m2}— \qquad (X), \text{ or}$$

$$—(C_y \text{ alkylene-NH})_{n2}—(CH_2)_{m2}— \qquad (X')$$

wherein
y is 2 or 3 (preferably 2),
n2 is 1 to 6 (preferably 1 to 3), and
m2 is 0 to 3 (preferably 0 to 2)),
$L^1$ is preferably (ethylene-O)$_{n2'}$—(CH$_2$)$_{m2'}$— or (propylene-O)$_{n2'}$, —(CH$_2$)$_{m2'}$— wherein n2' is 1 to 3, and m2' is 0 to 2,
$X^1$ is an optionally substituted divalent 5- or 6-membered aromatic carbocyclic group (particularly, a phenylene group substituted by an amide group or an unsubstituted phenylene group), an optionally substituted divalent 5- or 6-membered aromatic heterocyclic group (particularly, a pyrazolyl ring or triazolyl), or an optionally substituted divalent 6-membered nonaromatic heterocyclic group (particularly, piperidinyl substituted by an amide group), and
$L^2$ is a bond or a carbonyl group (particularly, a carbonyl group bonded to a heteroatom (particularly, a nitrogen atom) of a heterocyclic ring); and
$R^2$ represents a group selected from the formulas (III), (IV), (V), (VI), and (VII) wherein
$R^{41}$, $R^{42}$, $R^{43}$, $R^{44}$, $R^{45}$, $R^{46}$, $R^{47}$, $R^{48}$, $R^{49}$ and $R^{410}$ are each independently a hydrogen atom, an optionally substituted amino group (particularly, an unsubstituted amino group or an amino group substituted by a $C_{1-6}$ alkylcarbonyl group (particularly, a methylcarbonyl group)), or a $C_{1-6}$ alkyl group (particularly, a methyl group), or $R^{41}$ and $R^{42}$ are optionally bonded to each other to form an optionally substituted 5- or 6-membered aromatic heterocyclic ring condensed with a 6-membered ring of purine (particularly, a condensed imidazole ring), $R^{B1}$, $R^{B2}$, $R^{B3}$, $R^{B4}$ and $R^{B5}$ are each independently
(i) an optionally substituted $C_{3-10}$ cycloalkyl group (particularly, a cyclopentyl group or a cyclohexyl group),
(ii) an optionally substituted $C_{6-14}$ aryl group (particularly, a phenyl group),
(iii) an optionally substituted 5- or 6-membered nonaromatic heterocyclic group (particularly, ribose),
(iv) a methylene group substituted by a $C_{6-14}$ aryl group (particularly, a benzyl group),
(v) a methylene group substituted by a halogenated $C_{6-14}$ aryl group (particularly, a benzyl group substituted by fluorine or chlorine at a para, meta or ortho position),
(vi) a methylene group substituted by a $C_{6-14}$ aryl group substituted by one to three cyano groups (particularly, a benzyl group substituted by one cyano group),
(vii) a methylene group substituted by a $C_{6-14}$ aryl group substituted by one to three $C_{1-6}$ alkyl groups (particularly, a benzyl group substituted by one $C_{1-6}$ alkyl group (particularly, methyl group)),
(viii) a methylene group substituted by a $C_{6-14}$ aryl group substituted by one to three $C_{1-6}$ alkoxy groups (particularly, a benzyl group substituted by one methoxy group),
(ix) a methylene group substituted by a $C_{6-14}$ aryl group substituted by one to three $C_{1-6}$ alkylsulfonyl groups (particularly, a benzyl group substituted by a methylsulfonyl group),
(x) a methylene group substituted by a 5- to 14-membered aromatic heterocyclic group optionally substituted by one to three $C_{1-6}$ alkyl groups, preferably a methylene group substituted by a 5- or 6-membered aromatic heterocyclic group optionally substituted by one to three $C_{1-6}$ alkyl groups (particularly, a methylene group substituted by a pyridyl group, a thiazole group, or a pyrazole group substituted by a $C_{1-6}$ alkyl group (particularly, a methyl group)), or
a methylene group substituted by a 5- to 14-membered nonaromatic heterocyclic group, preferably a methylene group substituted by a 5- or 6-membered nonaromatic heterocyclic group (particularly, a methylene group substituted by a tetrahydropyranyl group).

Compound (B): a compound (I) wherein
$R^1$ is a ligand specifically binding to an intracellular protein fused with HaloTag, BRD4, Ras, FKBP12 or MetAP2;
$L^a$ is an ethylene group or a —NH-ethylene group;
$L^b$ is
i) a chain linker represented by the formula:

-(ethylene-O)$_{n1}$—(CH$_2$)$_{m1}$—B$_1$    (IX)

wherein
n1 is 1 or 2,
m1 is 1, and
B$_1$ is
(i) —NH—,
(ii) —NH—(CO)—,
(iii) —NH—(CO)-ethylene,
(iv) a —NH—C$_{1-3}$ alkylene group (particularly, an aminomethylene group), or
(v) —N2 acetyl-L-cysteinamide, or
ii) represented by the formula:

[Formula 27]

-L$^1$-X$^1$-L$^2$-    (II)

wherein
$L^1$ is -(ethylene-O)$_{n2}$—(CH$_2$)$_{m2}$— wherein n2 is 1 to 3, and m2 is 0 or 1,
$X^1$ is a phenylene group substituted by an amide group, and
$L^2$ is a bond; and
$R^2$ represents a group selected from the formulas (III), (IV), and (V), wherein:
when $R^2$ is a group of the formula (III),
$R^{41}$ is a hydrogen atom,
$R^{42}$ is an optionally substituted amino group (particularly, an unsubstituted amino group), and
$R^{B1}$ is
(i) an optionally substituted 5- or 6-membered nonaromatic heterocyclic group (particularly, ribose),
(ii) a methylene group substituted by a halogenated $C_{6-14}$ aryl group (particularly, a benzyl group substituted by fluorine or chlorine), or
(iii) a methylene group substituted by a $C_{6-14}$ aryl group substituted by a $C_{1-6}$ alkyl group (particularly, a benzyl group substituted by a $C_{1-6}$ alkyl group (particularly, a methyl group));
when $R^2$ is a group of the formula (IV),
$R^{43}$ is an optionally substituted amino group (particularly, an unsubstituted amino group),
$R^{44}$ is a hydrogen atom, and
$R^{B2}$ is a methylene group substituted by a halogenated $C_{6-14}$ aryl group (particularly, a benzyl group substituted by fluorine or chlorine); and
when $R^2$ is a group of the formula (V),
$R^{45}$ and $R^{46}$ are each independently
(i) a hydrogen atom, or
(ii) a $C_{1-6}$ alkyl group (particularly, a methyl group), and
$R^{B3}$ is a methylene group substituted by a halogenated $C_{6-14}$ aryl group (particularly, a benzyl group substituted by fluorine or chlorine).

A salt of compound (I) is preferably a pharmacologically acceptable salt. Examples thereof include salts with inorganic bases, salts with organic bases, salts with inorganic acids, salts with organic acids, and salts with basic or acidic amino acids.

Preferred examples of the salt with an inorganic base include: alkali metal salts such as sodium salt and potassium salt; alkaline earth metal salts such as calcium salt and magnesium salt; and aluminum salts and ammonium salts.

Preferred examples of the salt with an organic base include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine, or N,N-dibenzylethylenediamine Preferred examples of the salt with an inorganic acid include salts with hydrochloric acid, hydrobromic acid, nitric acid, sulfuric acid, or phosphoric acid.

Preferred examples of the salt with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, or p-toluenesulfonic acid.

Preferred examples of the salt with a basic amino acid include salts with arginine, lysine, or ornithine.

Preferred examples of the salt with an acidic amino acid include salts with aspartic acid or glutamic acid.

A method for producing the compound of the present invention will be described below.

A starting material or a reagent used in each step in the production method given below and the obtained compound may each form a salt. Examples of such a salt include the same as the aforementioned salt of the compound of the present invention.

When the compound obtained in each step is a free compound, this compound can be converted to a salt of interest by a method known per se in the art. On the contrary, when the compound obtained in each step is a salt, this salt can be converted to a free form or another type of salt of interest by a method known per se in the art.

The compound obtained in each step may be used in the next reaction in the form of its reaction solution or after being obtained as a crude product. Alternatively, the compound obtained in each step can be isolated and/or purified from the reaction mixture by a separation approach such as concentration, crystallization, recrystallization, distillation, solvent extraction, fractionation, or chromatography according to a routine method.

If a starting material or a reagent compound for each step is commercially available, the commercially available product can be used directly.

In the reaction of each step, the reaction time may differ depending on the reagent or the solvent used and is usually 1 minute to 48 hours, preferably 10 minutes to 8 hours, unless otherwise specified.

In the reaction of each step, the reaction temperature may differ depending on the reagent or the solvent used and is usually −78° C. to 300° C., preferably −78° C. to 150° C., unless otherwise specified.

In the reaction of each step, the pressure may differ depending on the reagent or the solvent used and is usually 1 atm to 20 atm, preferably 1 atm to 3 atm, unless otherwise specified.

In the reaction of each step, a microwave synthesis apparatus, for example, Initiator manufactured by Biotage Japan Ltd., may be used. The reaction temperature may differ depending on the reagent or the solvent used and is usually room temperature to 300° C., preferably 50° C. to 250° C., unless otherwise specified. The reaction time may differ depending on the reagent or the solvent used and is usually 1 minute to 48 hours, preferably 1 minute to 8 hours, unless otherwise specified.

In the reaction of each step, the reagent is used at 0.5 equivalents to 20 equivalents, preferably 0.8 equivalents to 5 equivalents, with respect to the substrate, unless otherwise specified. In the case of using the reagent as a catalyst, the reagent is used at 0.001 equivalents to 1 equivalent, preferably 0.01 equivalents to 0.2 equivalents, with respect to the substrate. When the reagent also serves as a reaction solvent, the reagent is used in the amount of the solvent.

In the reaction of each step, this reaction is carried out without a solvent or by dissolution or suspension in an appropriate solvent, unless otherwise specified. Specific examples of the solvent include solvents described in Examples and the following: alcohols: methanol, ethanol, tert-butyl alcohol, 2-methoxyethanol, and the like; ethers: diethyl ether, diphenyl ether, tetrahydrofuran, 1,2-dimethoxyethane, and the like; aromatic hydrocarbons: chlorobenzene, toluene, xylene, and the like;
  saturated hydrocarbons: cyclohexane, hexane, and the like;
  amides: N,N-dimethylformamide, N-methylpyrrolidone, and the like;
  halogenated hydrocarbons: dichloromethane, carbon tetrachloride, and the like;
  nitriles: acetonitrile and the like;
  sulfoxides: dimethyl sulfoxide and the like;
  aromatic organic bases: pyridine and the like;
  acid anhydrides: acetic anhydride and the like;
  organic acids: formic acid, acetic acid, trifluoroacetic acid, and the like;
  inorganic acids: hydrochloric acid, sulfuric acid, and the like;
  esters: ethyl acetate and the like;
  ketones: acetone, methyl ethyl ketone, and the like; and water.

Two or more of these solvents may be used as a mixture at an appropriate ratio.

In the case of using a base in the reaction of each step, for example, the following base or a base described in Examples is used:
  inorganic bases: sodium hydroxide, magnesium hydroxide, and the like;
  basic salts: sodium carbonate, calcium carbonate, sodium bicarbonate, and the like;
  organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine, and the like;
  metal alkoxides: sodium ethoxide, potassium tert-butoxide, and the like;
  alkali metal hydrides: sodium hydride, and the like;
  metal amides: sodium amide, lithium diisopropylamide, lithium hexamethyldisilazide, and the like; and
  organic lithiums: n-butyllithium and the like.

In the case of using an acid or an acidic catalyst in the reaction of each step, for example, the following acid or acidic catalyst or an acid or an acidic catalyst described in Examples is used:
  inorganic acids: hydrochloric acid, sulfuric acid, nitric acid, hydrobromic acid, phosphoric acid, and the like;
  organic acids: acetic acid, trifluoroacetic acid, citric acid, p-toluenesulfonic acid, 10-camphorsulfonic acid, and the like; and
  Lewis acids: boron trifluoride-diethyl ether complex, zinc iodide, anhydrous aluminum chloride, anhydrous zinc chloride, anhydrous iron chloride, and the like.

The reaction of each step is carried out according to a method known per se in the art, for example, a method described in The Fifth Series of Experimental Chemistry, Vol. 13 to Vol. 19 (edited by The Chemical Society of Japan); Shin Jikken Kagaku Koza (New Experimental Chemistry in English), Vol. 14 to Vol. 15 (edited by The Chemical Society of Japan); Syntheses in the Organic Chemistry Laboratory, Revised, 2nd Ed. (L. F. Tietze, Th. Eicher, Nankodo Co., Ltd.); Organic Name Reactions; The Reaction Mechanism and Essence, Revised (Hideo Tougo, Kodansha Ltd.); Organic Syntheses Collective Volume I to VII (John Wiley & Sons, Inc.); Modern Organic Synthesis in the Laboratory: A Collection of Standard Experimental Procedures (Jie Jack Li, Oxford University Press); Comprehensive Heterocyclic Chemistry III, Vol. 1 to Vol. 14 (Elsevier Japan KK); Strategic Applications of Named Reactions in Organic Synthesis (translated by Kiyoshi Tomioka, published by Kagaku-Dojin Publishing Company, Inc.); Comprehensive Organic Transformations (VCH Publishers, Inc.) (1989), etc., or a method described in Examples, unless otherwise specified.

In each step, the protection or deprotection reaction of a functional group is carried out according to a method known per se in the art, for example, a method described in "Protective Groups in Organic Synthesis, 4th Ed." (Theodora W. Greene, Peter G. M. Wuts), Wiley-Interscience (2007); "Protecting Groups, 3rd Ed." (P. J. Kocienski), Thieme Medical Publishers (2004), etc., or a method described in Examples.

Examples of a protective group for a hydroxy group or a phenolic hydroxy group in an alcohol or the like include: ether-type protective groups such as methoxy methyl ether, benzyl ether, t-butyl dimethyl silyl ether, and tetrahydropyranyl ether; carboxylic acid ester-type protective groups such as acetic acid ester; sulfonic acid ester-type protective groups such as methanesulfonic acid ester; and carbonic acid ester-type protective groups such as t-butyl carbonate.

Examples of a protective group for a carbonyl group in an aldehyde include: acetal-type protective groups such as dimethylacetal; and cyclic acetal-type protective groups such as cyclic 1,3-dioxane.

Examples of a protective group for a carbonyl group in a ketone include: ketal-type protective groups such as dimethylketal; cyclic ketal-type protective groups such as cyclic 1,3-dioxane; oxime-type protective groups such as O-methyloxime; and hydrazone-type protective groups such as N,N-dimethylhydrazone.

Examples of a protective group for a carboxyl group include: ester-type protective groups such as methyl ester; and amide-type protective groups such as N,N-dimethylamide.

Examples of a protective group for a thiol include: ether-type protective groups such as benzyl thioether; and ester-type protective groups such as thioacetic acid ester, thiocarbonate, and thiocarbamate.

Examples of a protective group for an amino group or an aromatic heterocyclic ring such as imidazole, pyrrole, or indole include: carbamate-type protective groups such as benzyl carbamate; amide-type protective groups such as acetamide; alkylamine-type protective groups such as N-triphenylmethylamine; and sulfonamide-type protective groups such as methanesulfonamide.

Removal of a protective group can be carried out by use of a method known per se in the art, for example, a method using an acid, a base, ultraviolet light, hydrazine, phenylhydrazine, sodium N-methyldithiocarbamate, tetrabutylammonium fluoride, palladium acetate, or trialkylsilyl halide (e.g., trimethylsilyl iodide and trimethylsilyl bromide), or a reduction method.

In the case of carrying out reduction reaction in each step, examples of the reducing agent used include: metal hydrides such as lithium aluminum hydride, sodium triacetoxyborohydride, sodium cyanoborohydride, diisobutyl aluminum hydride (DIBAL-H), sodium borohydride, and tetramethylammonium triacetoxyborohydride; boranes such as a borane-tetrahydrofuran complex; Raney nickel; Raney cobalt; hydrogen; and formic acid. In the case of reducing a carbon-carbon double bond or triple bond, a method using a catalyst such as palladium-carbon or a Lindlar's catalyst can be used.

In the case of carrying out oxidation reaction in each step, examples of the oxidizing agent used include: peracids such as m-chloroperbenzoic acid (MCPBA), hydrogen peroxide, and t-butyl hydroperoxide; perchlorates such as tetrabutylammonium perchlorate; chlorates such as sodium chlorate; chlorites such as sodium chlorite; periodates such as sodium periodate; high-valent iodine reagents such as iodosylbenzene; reagents having manganese, such as manganese dioxide and potassium permanganate; leads such as lead tetraacetate; reagents having chromium, such as pyridinium chlorochromate (PCC), pyridinium dichromate (PDC), and Jones reagents; halogen compounds such as N-bromosuccinimide (NBS); oxygen; ozone; a sulfur trioxide-pyridine complex; osmium tetroxide; selenium dioxide; and 2,3-dichloro-5,6-dicyano-1,4-benzoquinone (DDQ).

In the case of carrying out aromatic nucleophilic substitution reaction in each step, a nucleophile (e.g., ammonia, amines, thiols, imidazole, alcohols, and water) and a base (e.g., inorganic bases and organic bases) are used as reagents. In the case of reaction with water, the reaction may be carried out in an acidic solvent such as trifluoroacetic acid, acetic acid, formic acid, or hydrochloric acid.

In the case of carrying out azidation reaction of alcohols, alkyl halides, or sulfonic acid esters in each step, examples of the azidating agent used include diphenylphosphorylazide (DPPA), trimethylsilylazide, and sodium azide. In the case of azidating, for example, alcohols, a method using diphenylphosphorylazide and 1,8-diazabicyclo[5.4.0]undec-7-ene (DBU), a method using trimethylsilylazide and a Lewis acid, or the like can be used.

In the case of carrying out reductive amination reaction in each step, examples of the reducing agent used include sodium triacetoxyborohydride, sodium cyanoborohydride, hydrogen, and formic acid. When the substrate is an amine compound, examples of the carbonyl compound used include p-formaldehyde as well as aldehydes such as acetaldehyde, and ketones such as cyclohexanone. When the substrate is a carbonyl compound, examples of the amines used include: primary amine such as ammonia and methylamine; and secondary amine such as dimethylamine In the case of carrying out Mitsunobu reaction in each step, azodicarboxylic acid esters (e.g., diethyl azodicarboxylate (DEAD) and diisopropyl azodicarboxylate (DIAD)) and triphenylphosphine are used as reagents.

In the case of carrying out esterification reaction, amidation reaction, or ureation reaction in each step, examples of the reagent used include: an acyl halide form of acid chloride, acid bromide, and the like; and activated carboxylic acids such as an acid anhydride, an active ester form, and a sulfuric acid ester form. Examples of the activator for carboxylic acid include: carbodiimide condensing agents such as 1-ethyl-3-(3-dimethylaminopropyl)carbodiimide hydrochloride (WSCD); triazine condensing agents such as 4-(4,6-dimethoxy-1,3,5-triazin-2-yl)-4-methylmorpholinium chloride-n-hydrate (DMT-MM); carbonic acid ester condensing agents such as 1,1-carbonyldiimidazole (CDI); diphenylphosphorylazide (DPPA); benzotriazol-1-yloxytrisdimethylaminophosphonium salt (BOP reagent); 2-chloro-1-methyl-pyridinium iodide (Mukaiyama reagent); thionyl chloride; lower alkyl haloformate such as ethyl chloroformate; O-(7-azabenzotriazol-1-yl)-N,N,N',N'-tetramethyluronium hexafluorophosphate (HATU); sulfuric acid; and combinations thereof. In the case of using a carbodiimide condensing agent, an additive such as 1-hydroxybenzotriazole (HOBt), N-hydroxysuccinimide (HOSu), or dimethylaminopyridine (DMAP) may be further added for the reaction.

In the case of carrying out coupling reaction in each step, examples of the metal catalyst used include: palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, and palladium(II) acetate; nickel compounds such as tetrakis(triphenylphosphine)nickel(0); rhodium compounds such as tris(triphenylphosphine)rhodium(III) chloride; cobalt compounds; copper compounds such as copper oxide and copper (I) iodide; and platinum compounds. A ligand such as triphenylphosphine, 1,1'-bis(diphenylphosphino)ferrocene, or triphenylphosphine-3,3',3"-trisulfonic acid trisodium salt may be added for the reaction. A base may be further added for the reaction. Examples of such a base include inorganic bases and basic salts.

In the case of carrying out Wohl-Ziegler reaction in each step, examples of the halogenating agent used include N-iodosuccinimide, N-bromosuccinimide (NBS), N-chlorosuccinimide (NCS), bromine, and sulfuryl chloride. The reaction can be accelerated by the further addition of a radical initiator such as heat, light, benzoyl peroxide, or azobisisobutyronitrile for the reaction.

In the case of carrying out sulfone-esterification reaction in each step, examples of the sulfonylating agent used include methanesulfonyl chloride, p-toluenesulfonyl chloride, methanesulfonic anhydride, and p-toluenesulfonic anhydride.

In the case of carrying out hydrolysis reaction in each step, an acid or a base is used as a reagent. In the case of carrying out acid hydrolysis reaction of t-butyl ester, formic acid, triethylsilane, or the like may be added in order to reductively trap a by-product t-butyl cation.

In the case of carrying out bromination reaction in each step, examples of the brominating agent used include N-bromosuccinimide (NBS) and bromine.

In the case of carrying out N-alkylation reaction in each step, an electrophile (e.g., alkyl halide, and sulfonic acid esters such as mesylic acid alkyl ester and tosylic acid alkyl ester) and a base (e.g., basic salts and organic bases) are used as reagents.

In the case of carrying out hydroxylation reaction via diazotization in each step, a nitrous acid compound (e.g., inorganic nitrous acid salts such as sodium nitrite, and organic nitrous acids such as butyl nitrite) is used as a reagent in the presence of water. A copper salt such as copper oxide may be further added.

In the case of carrying out deamination reaction in each step, a nitrous acid compound (e.g., inorganic nitrous acid salts such as sodium nitrite, and organic nitrous acids such as butyl nitrite) is used as a reagent. This reaction may be carried out in the presence of a reducing agent. Phosphorous acid, sodium borohydride, triethylsilane, or the like is used as the reducing agent.

In the case of carrying out cyclization reaction in each step, an acidic reagent such as trifluoroacetic acid, acetic acid, hydrochloric acid, or sulfuric acid is used. Orthoester such as triethyl orthoformate or trimethyl orthoformate is used, if necessary.

In the case of carrying out carbamation reaction in each step, alcohols can be converted to active carbonic acid esters, which are then reacted with amines for synthesis. For the conversion of an alcohol to an active carbonic acid ester, p-nitrophenyl chloroformate or phosgene and a base (e.g., basic salts and organic bases) are used as reagents. The active carbonic acid ester thus produced can be reacted with an amine in the presence of a base (e.g., basic salts and organic bases) to obtain a carbamate form.

In the case of carrying out amidation or esterification through carbon monoxide insertion reaction in each step, this reaction is carried out using alcohols or amines in the presence of a metal catalyst and bases in a carbon monoxide atmosphere. Examples of the metal catalyst used include: palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, and palladium(II) acetate; and nickel compounds such as tetrakis(triphenylphosphine)nickel(0). The pressure of carbon monoxide may differ depending on the reagent or the solvent used and is usually 1 atm to 100 atm, preferably 1 atm to 20 atm. Examples of the base used include inorganic bases and basic salts. A ligand such as triphenylphosphine or 1,1'-bis(diphenylphosphino)ferrocene may be added for the reaction.

In the case of carrying out Click reaction in each step, a copper salt may be used as a reagent. Examples of the copper salt used include copper(II) acetate, copper(I) iodide, and copper(II) sulfate. A ligand such as ascorbic acid or sodium ascorbate may be further added in order to accelerate the reaction.

Compound (A-8), compound (A-10), compound (A-13), compound (A-16) and compound (A-20), which are included in compound (I), can be produced by the following method from compound (A-1) or compound (A-3).

[Formula 28]

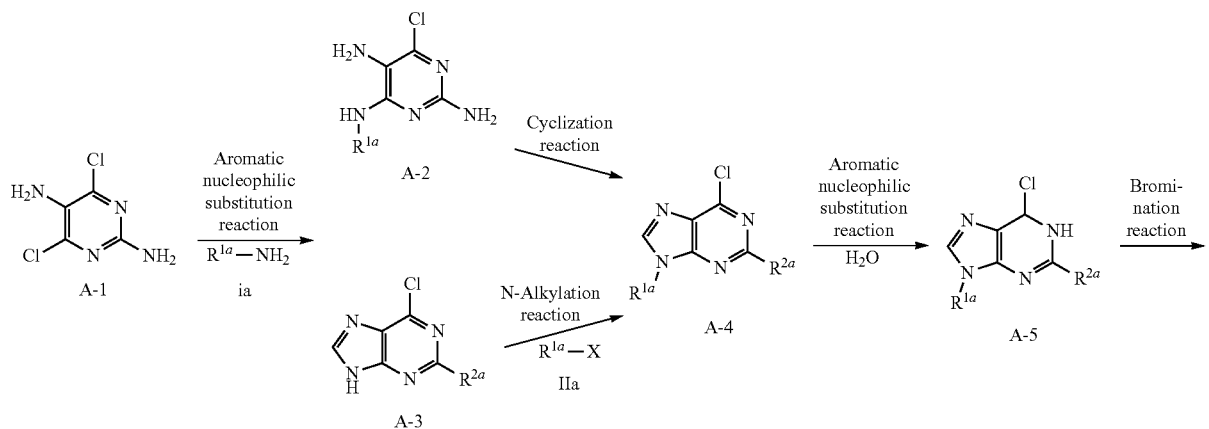

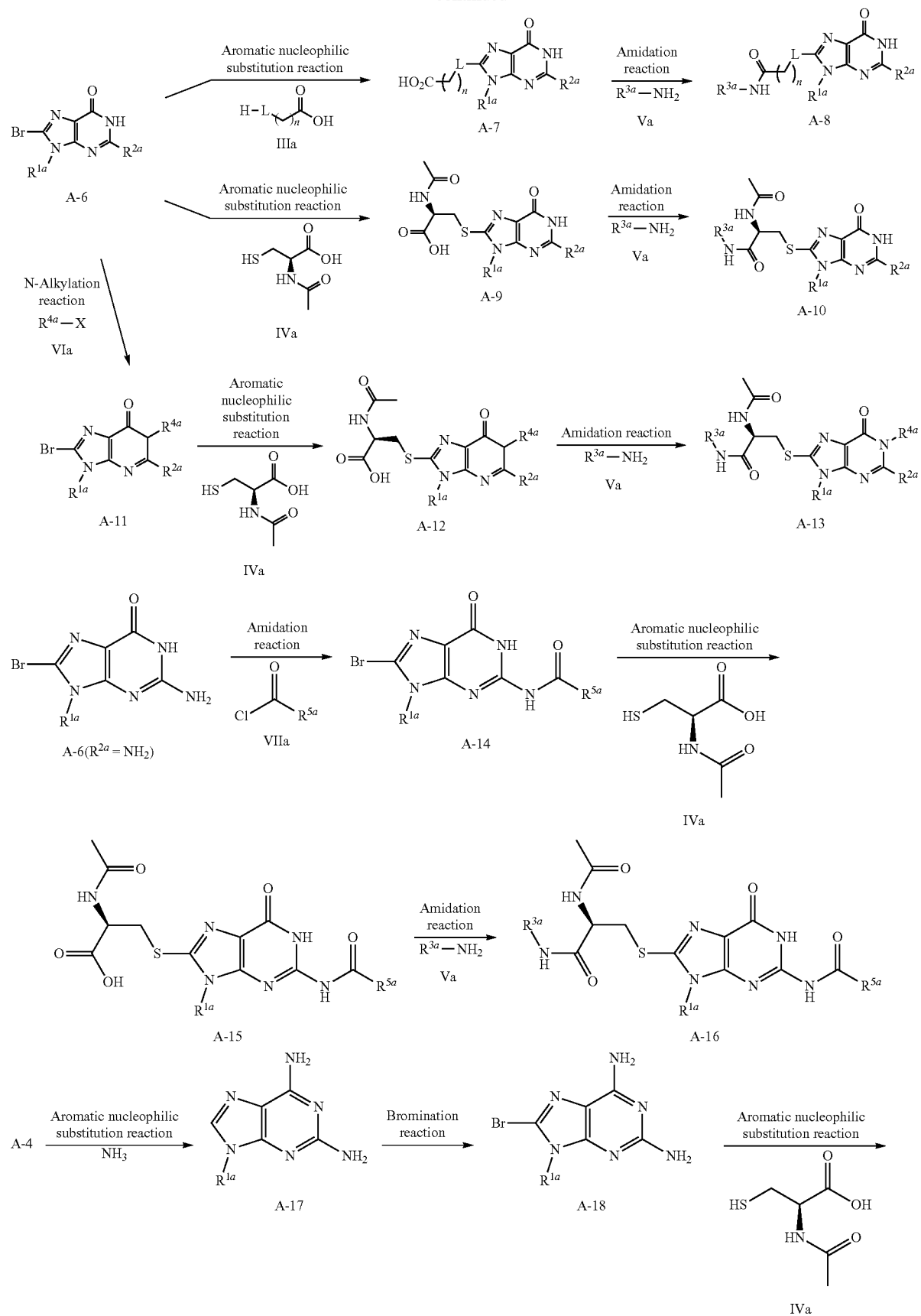

-continued
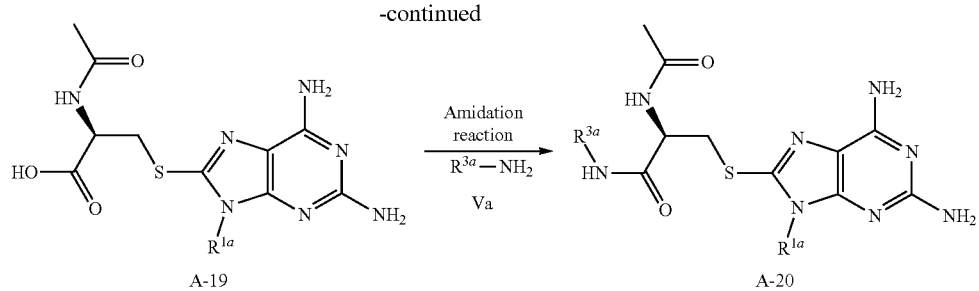
wherein
R[1a] represents
[Formula 29]
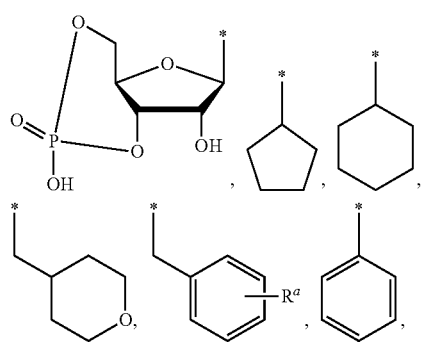
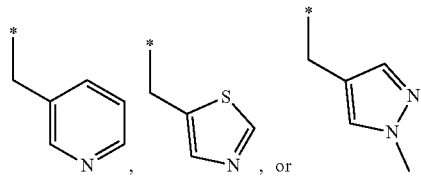
R[a] represents a hydrogen atom, a cyano group, a fluorine atom, a chlorine atom, a methyl group, a methoxy group or —SO$_2$Me,
R[2a] represents a hydrogen atom or an amino group,
R[3a] represents
[Formula 30]
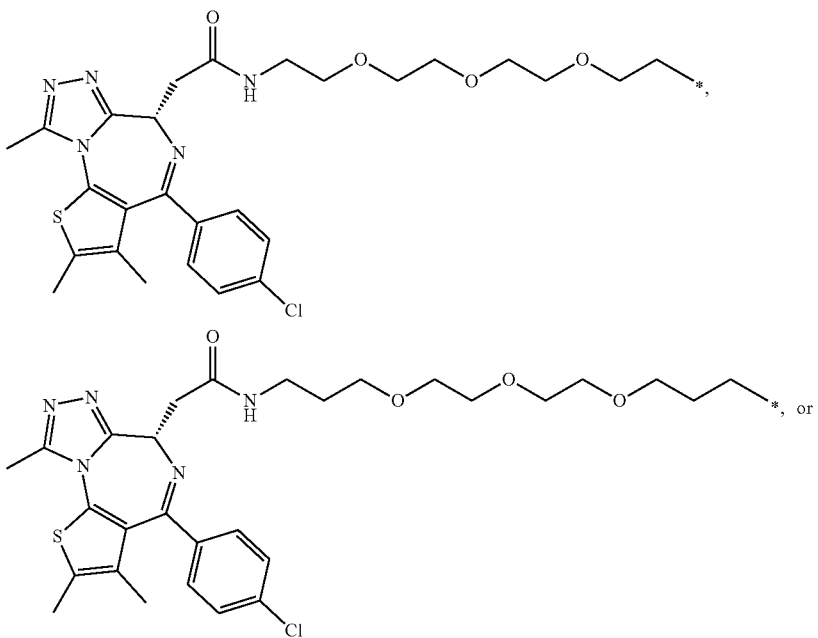

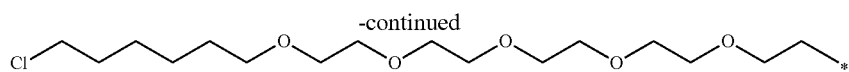

$R^{4a}$ and $R^{5a}$ each independently represent an alkyl group optionally having a substituent,
X represents a leaving group,
n represents an integer of 1 or 2, and
L represents —S— or —NH—.

Examples of the leaving group represented by X include halides and sulfonates.

The amine form (Va) described above in the method can be synthesized through, for example, the following reaction (e.g., amidation reaction and deprotection reaction).

[Formula 31]

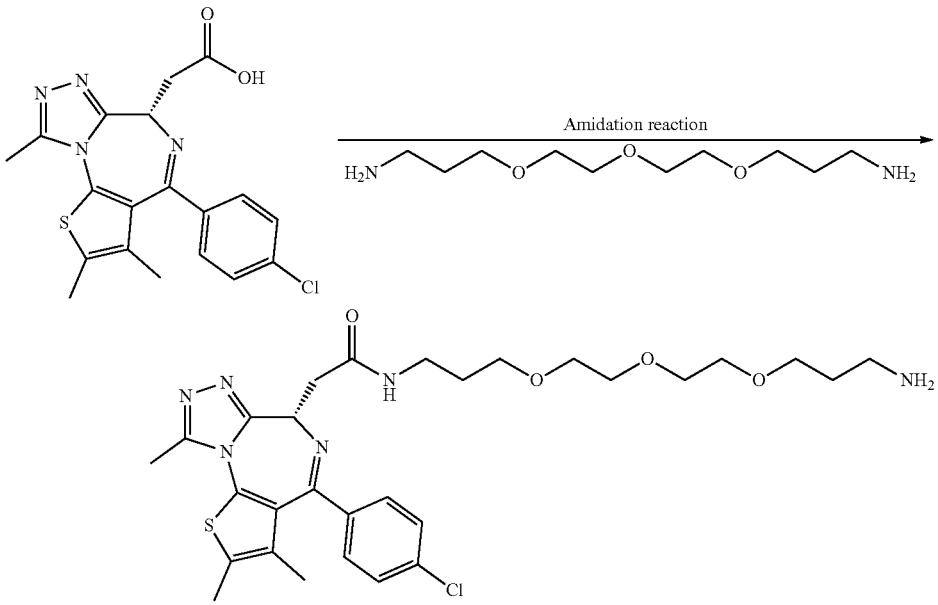

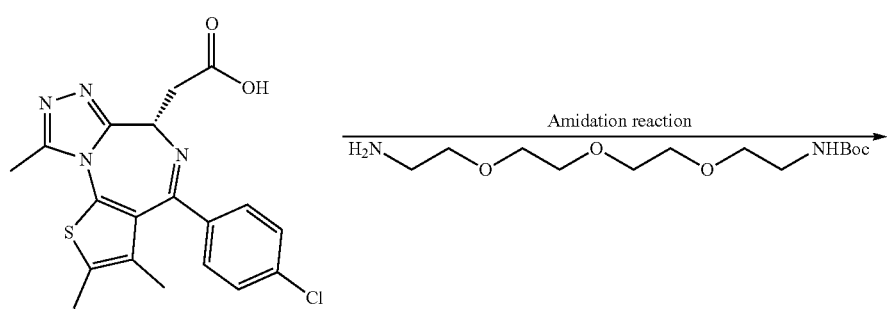

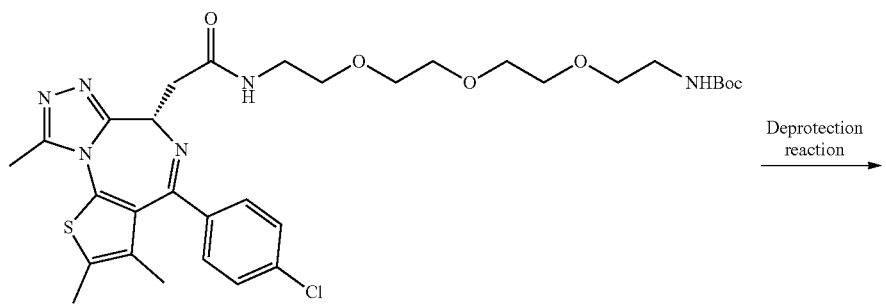

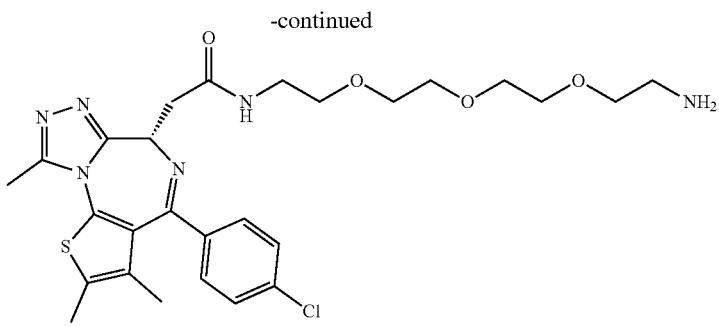

Compound (A-8) can be produced through the amidation reaction of compound (A-7) with amine form (Va).

Compound (A-7) can be produced through the aromatic nucleophilic substitution reaction of compound (A-6) with carboxylic acid (Ma).

Compound (A-6) can be produced through the bromination reaction of compound (A-5).

Compound (A-5) can be produced through the aromatic nucleophilic substitution reaction of compound (A-4) with water.

Compound (A-4) can be produced through the cyclization reaction of compound (A-2), or the N-alkylation reaction of compound (A-3) with compound (IIa).

Compound (A-2) can be produced through the aromatic nucleophilic substitution reaction of compound (A-1) with compound (Ia).

Compound (A-10) can be produced through the amidation reaction of compound (A-9) with amine form (Va).

Compound (A-9) can be produced through the aromatic nucleophilic substitution reaction of compound (A-6) with compound (IVa).

Compound (A-13) can be produced through the amidation reaction of compound (A-12) with amine form (Va).

Compound (A-12) can be produced through the aromatic nucleophilic substitution reaction of compound (A-11) with compound (IVa).

Compound (A-11) can be produced through the N-alkylation reaction of compound (A-6) with compound (VIa).

Compound (A-16) can be produced through the amidation reaction of compound (A-15) with amine form (Va).

Compound (A-15) can be produced through the aromatic nucleophilic substitution reaction of compound (A-14) with compound (IVa).

Compound (A-14) can be produced through the amidation reaction of compound (A-6 ($R^{2a}$=$NH_2$)) with compound (VIIa).

Compound (A-20) can be produced through the amidation reaction of compound (A-19) with amine form (Va).

Compound (A-19) can be produced through the aromatic nucleophilic substitution reaction of compound (A-18) with compound (IVa).

Compound (A-18) can be produced through the bromination reaction of compound (A-17).

Compound (A-17) can be produced through the aromatic nucleophilic substitution reaction of compound (A-4) with ammonia.

Compound (B-5), compound (B-7), and compound (B-9), which are included in compound (I), can be produced by the following method from compound (B-1), compound (A-9), or compound (A-12).

[Formula 32]

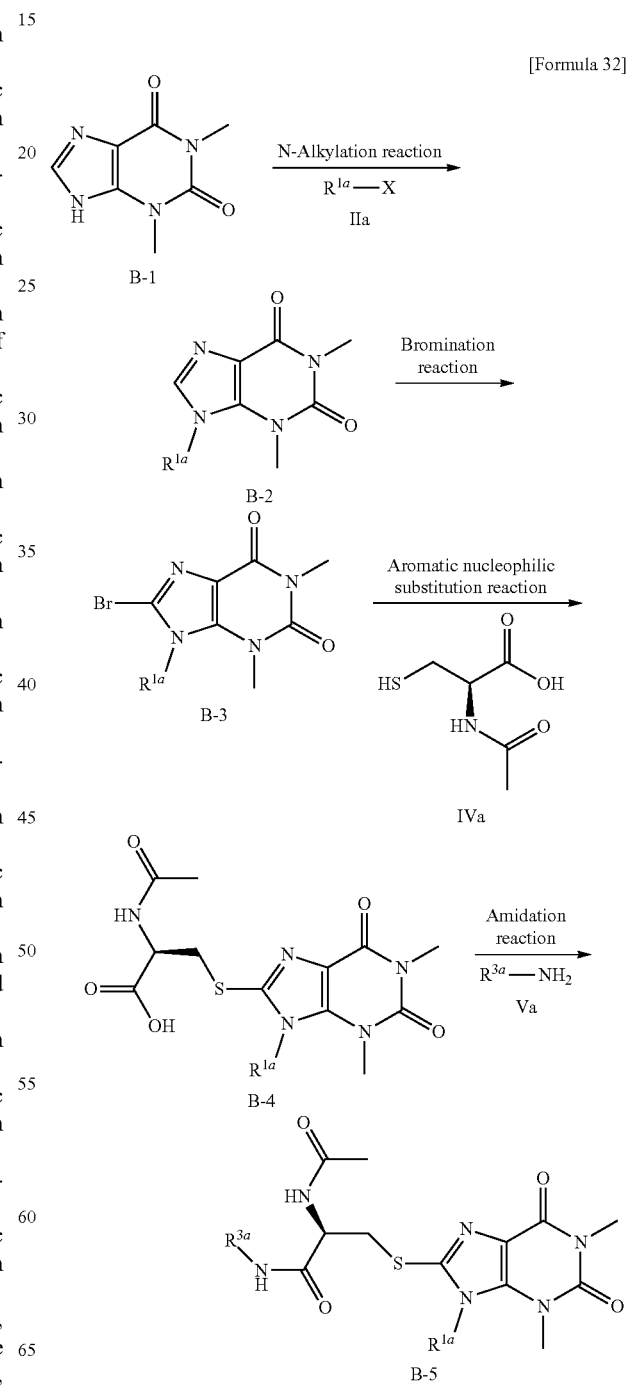

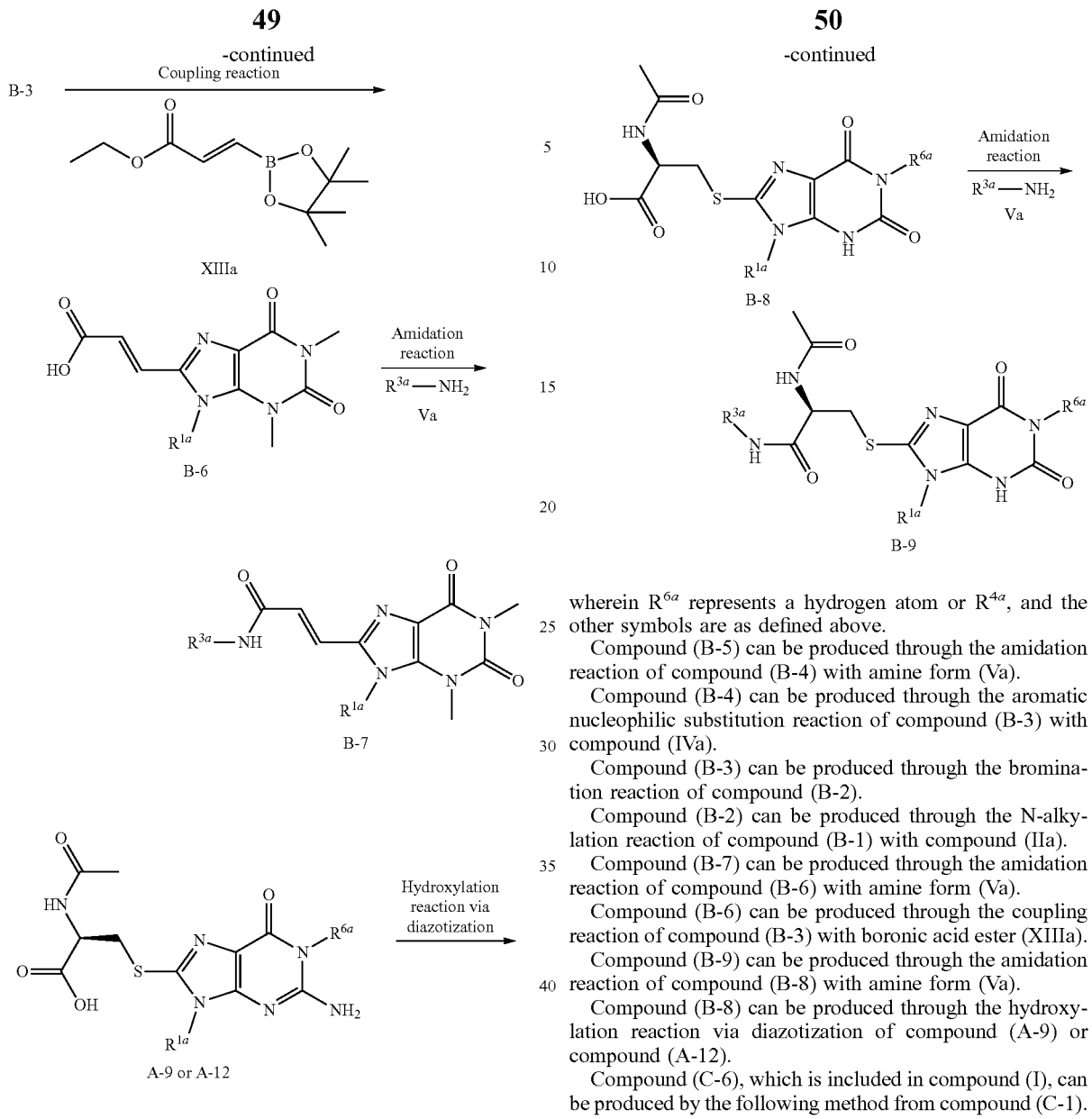

wherein $R^{6a}$ represents a hydrogen atom or $R^{4a}$, and the other symbols are as defined above.

Compound (B-5) can be produced through the amidation reaction of compound (B-4) with amine form (Va).

Compound (B-4) can be produced through the aromatic nucleophilic substitution reaction of compound (B-3) with compound (IVa).

Compound (B-3) can be produced through the bromination reaction of compound (B-2).

Compound (B-2) can be produced through the N-alkylation reaction of compound (B-1) with compound (IIa).

Compound (B-7) can be produced through the amidation reaction of compound (B-6) with amine form (Va).

Compound (B-6) can be produced through the coupling reaction of compound (B-3) with boronic acid ester (XIIIa).

Compound (B-9) can be produced through the amidation reaction of compound (B-8) with amine form (Va).

Compound (B-8) can be produced through the hydroxylation reaction via diazotization of compound (A-9) or compound (A-12).

Compound (C-6), which is included in compound (I), can be produced by the following method from compound (C-1).

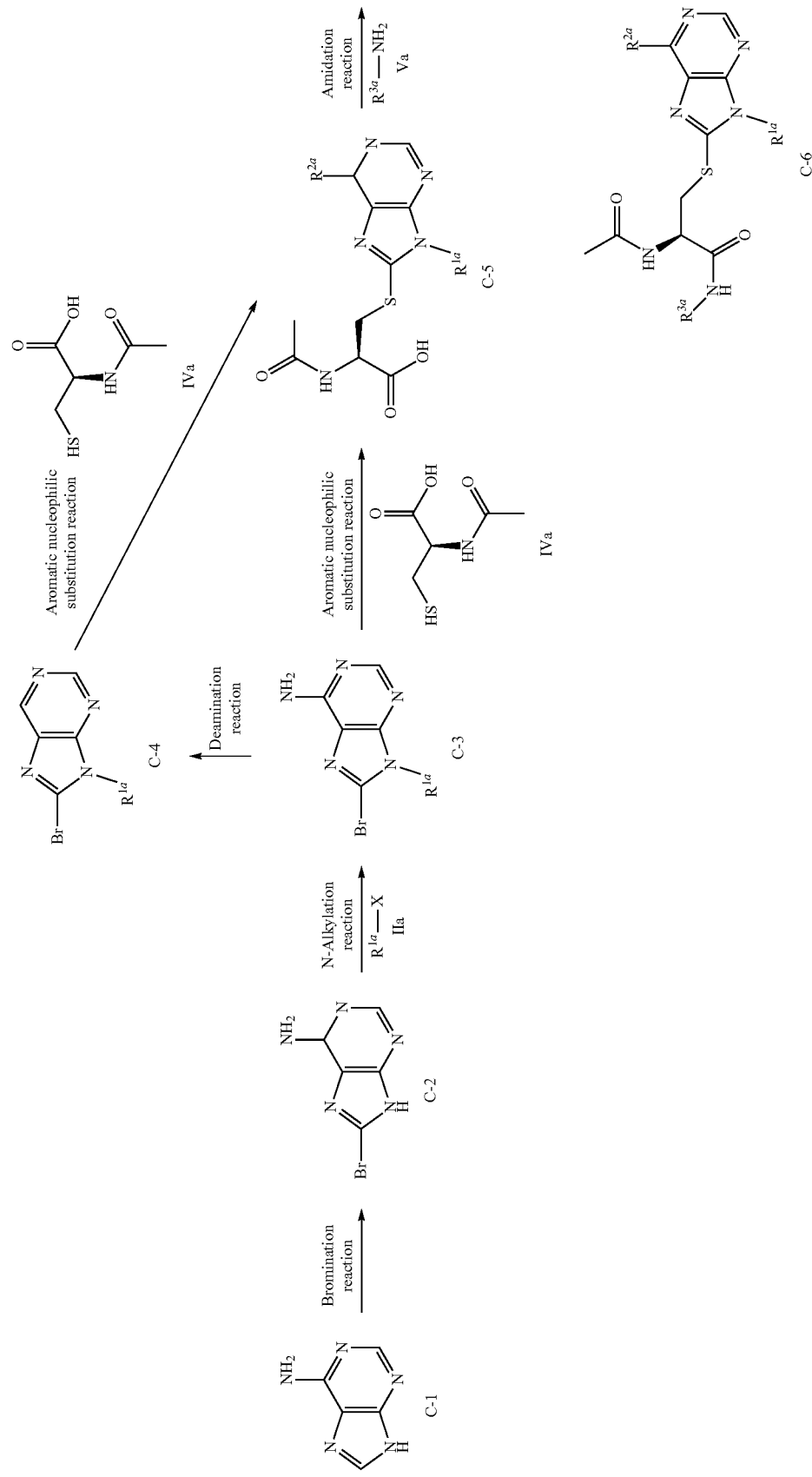

wherein each symbol is as defined above.

Compound (C-6) can be produced through the amidation reaction of compound (C-5) with amine form (Va).

Compound (C-5) can be produced through the aromatic nucleophilic substitution reaction of compound (C-4) or compound (C-3) with compound (IVa).

Compound (C-4) can be produced through the deamination reaction of compound (C-3).

Compound (C-3) can be produced through the N-alkylation reaction of compound (C-2) with compound (IIa).

Compound (C-2) can be produced through the bromination reaction of compound (C-1).

Compound (D-5), which is included in compound (1), can be produced by the following method from compound (D-1).

[Formula 34]

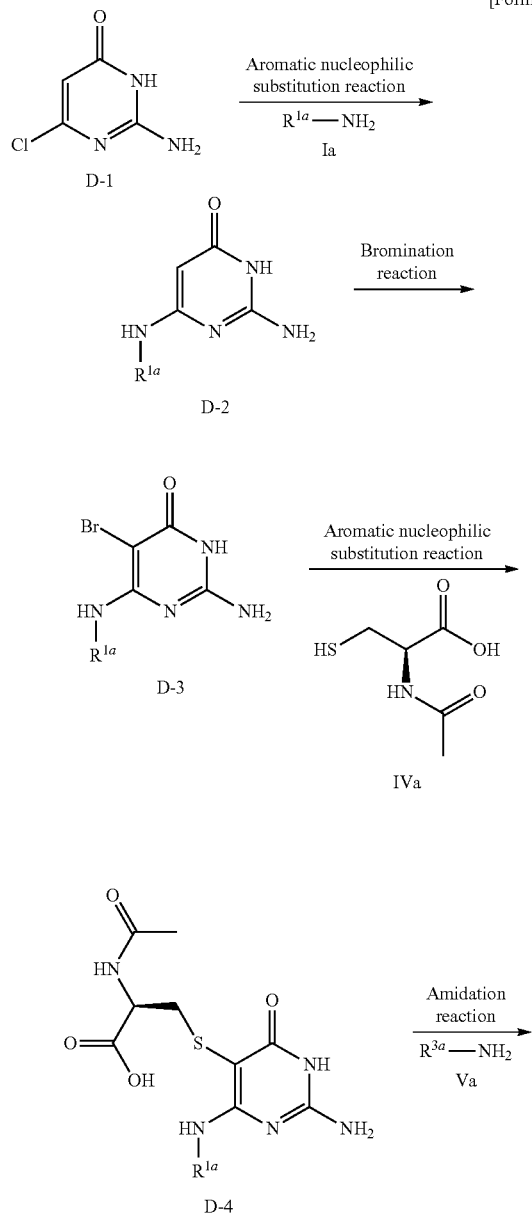

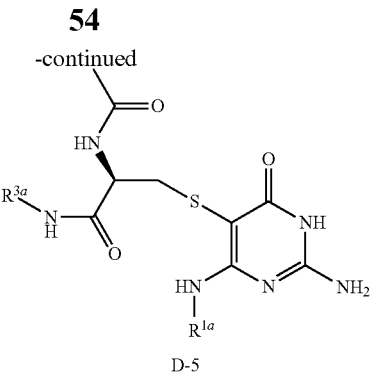

wherein each symbol is as defined above.

Compound (D-5) can be produced through the amidation reaction of compound (D-4) with amine form (Va).

Compound (D-4) can be produced through the aromatic nucleophilic substitution reaction of compound (D-3) with compound (IVa).

Compound (D-3) can be produced through the bromination reaction of compound (D-2).

Compound (D-2) can be produced through the aromatic nucleophilic substitution reaction of compound (D-1) with compound (Ia).

Compound (E-5), which is included in compound (I), can be produced by the following method from compound (E-1).

[Formula 35]

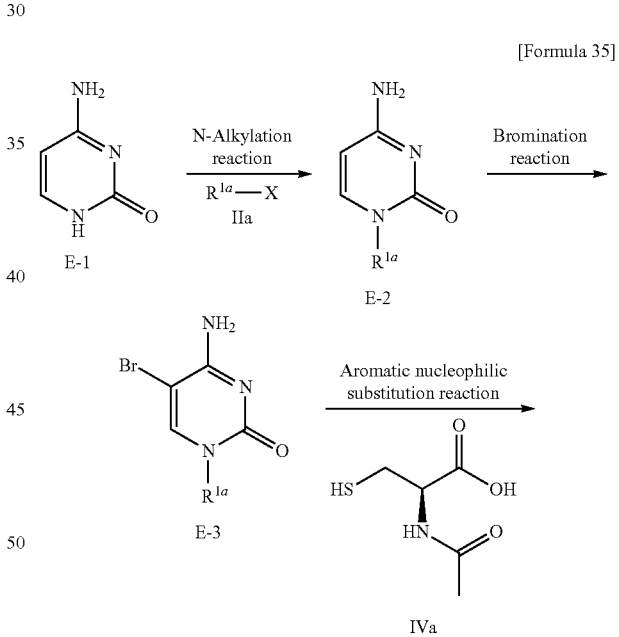

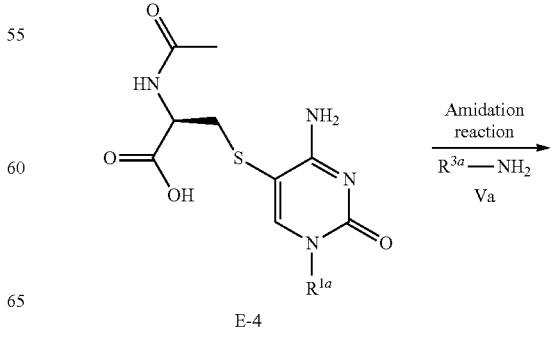

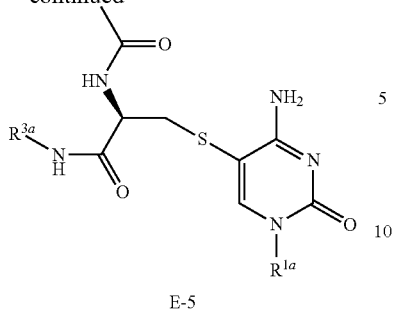

E-5 wherein each symbol is as defined above.

Compound (E-5) can be produced through the amidation reaction of compound (E-4) with amine form (Va).

Compound (E-4) can be produced through the aromatic nucleophilic substitution reaction of compound (E-3) with compound (IVa).

Compound (E-3) can be produced through the bromination reaction of compound (E-2).

Compound (E-2) can be produced through the N-alkylation reaction of compound (E-1) with compound (IIa).

Compound (F-4), which is included in compound (I), can be produced by the following method from compound (A-6 ($R^{2a}$=$NH_2$)).

[Formula 36]

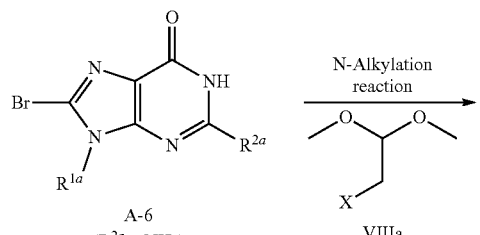

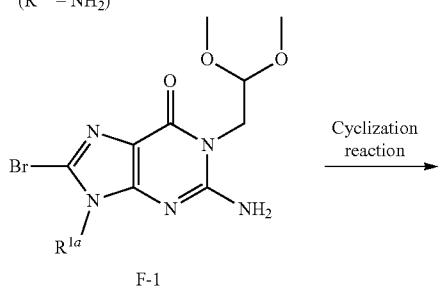

F-1

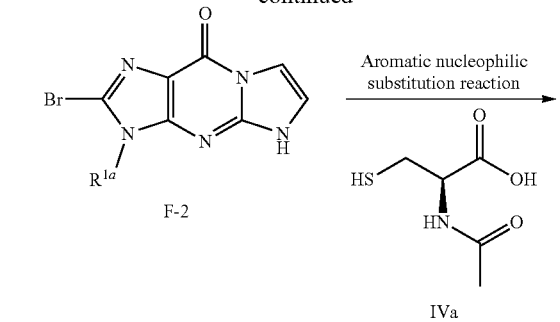

wherein each symbol is as defined above.

Compound (F-4) can be produced through the amidation reaction of compound (F-3) with amine form (Va).

Compound (F-3) can be produced through the aromatic nucleophilic substitution reaction of compound (F-2) with compound (IVa).

Compound (F-2) can be produced through the cyclization reaction of compound (F-1).

Compound (F-1) can be produced through the N-alkylation reaction of compound (A-6 ($R^{2a}$=$NH_2$)) with compound (VIIIa).

Compound (G-2), which is included in compound (I), can be produced by the following method from compound (A-6 ($R^{2a}$=$NH_2$)).

[Formula 37]

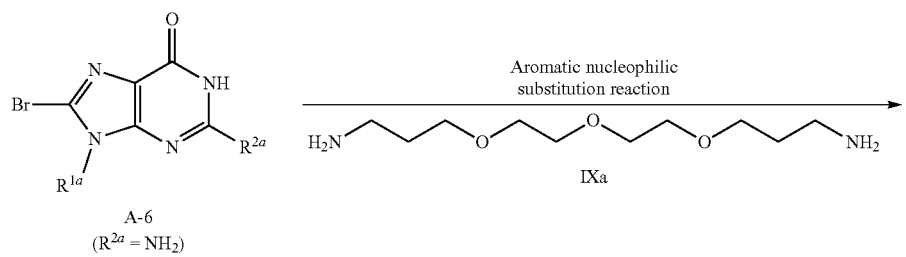

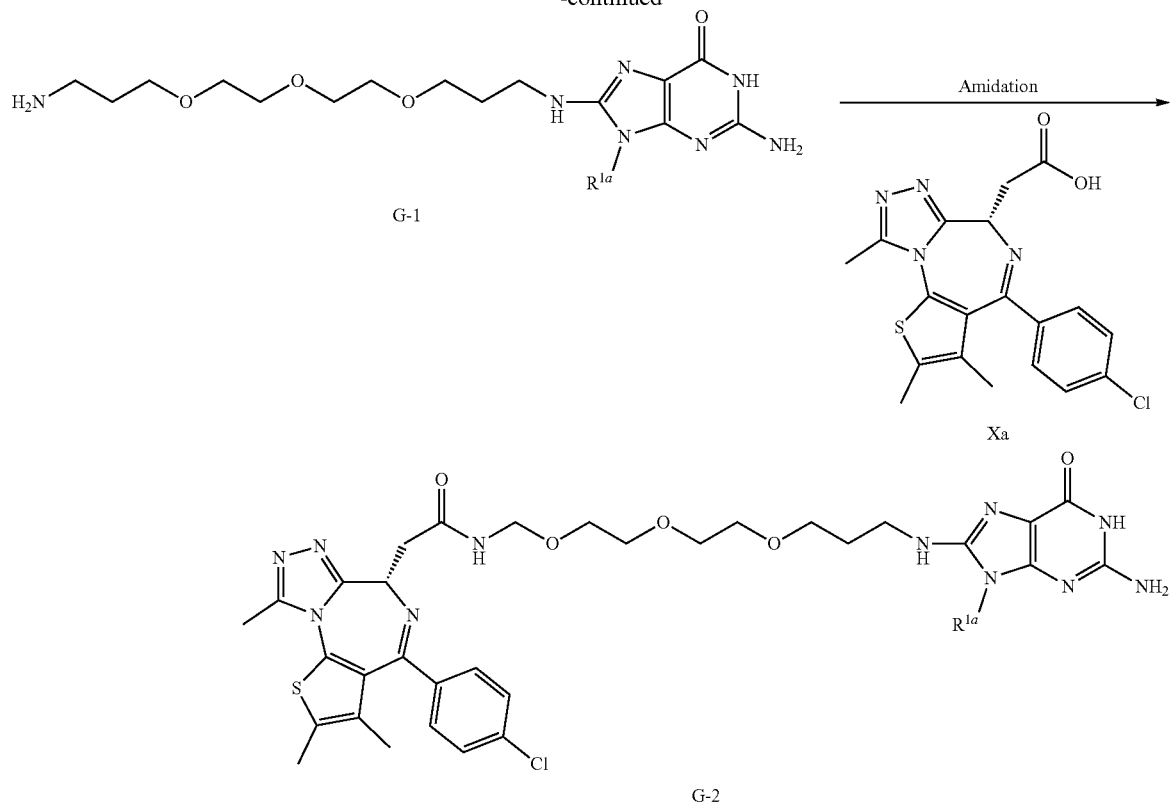

wherein each symbol is as defined above.

Compound (G-2) can be produced through the amidation reaction of compound (G-1) with carboxylic acid (Xa).

Compound (G-1) can be produced through the aromatic nucleophilic substitution reaction of compound (A-6 ($R^{2a}$=$NH_2$)) with compound (IXa).

Compound (H-2) and compound (H-3), which are included in compound (I), can be produced by the following method from compound (A-9 ($R^{2a}$=$NH_2$)).

[Formula 38]

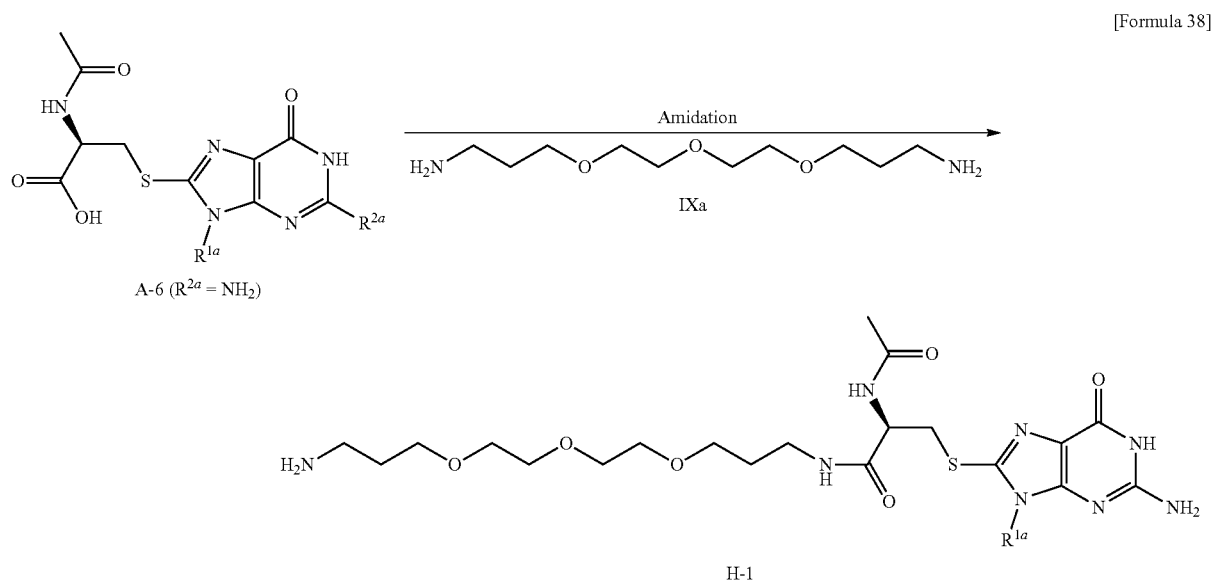

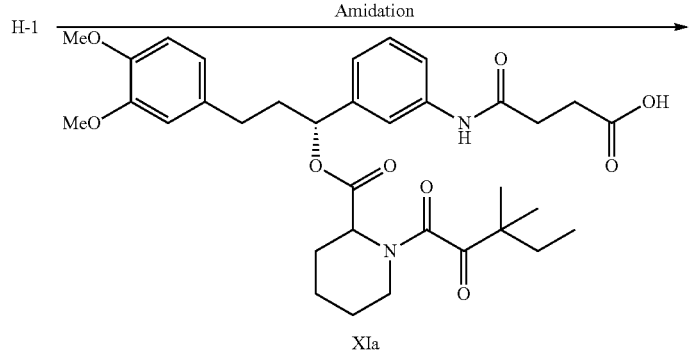

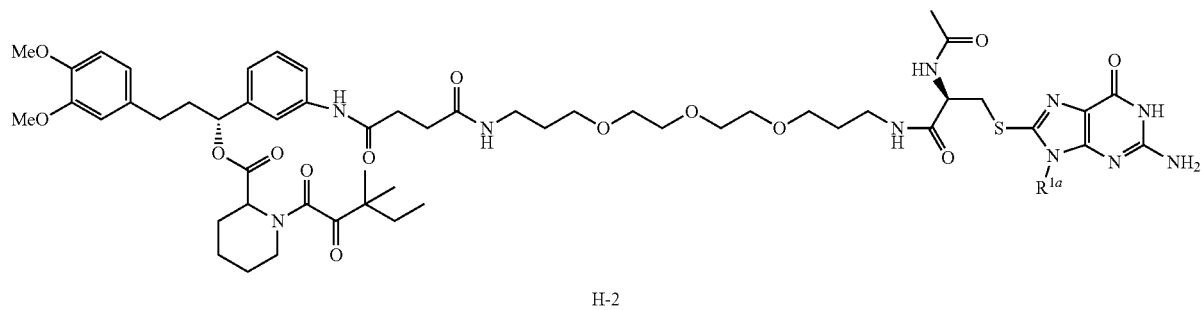

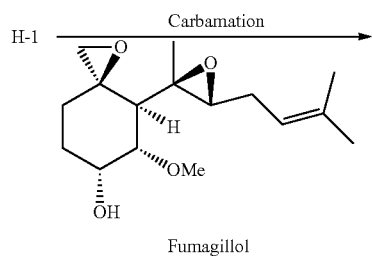

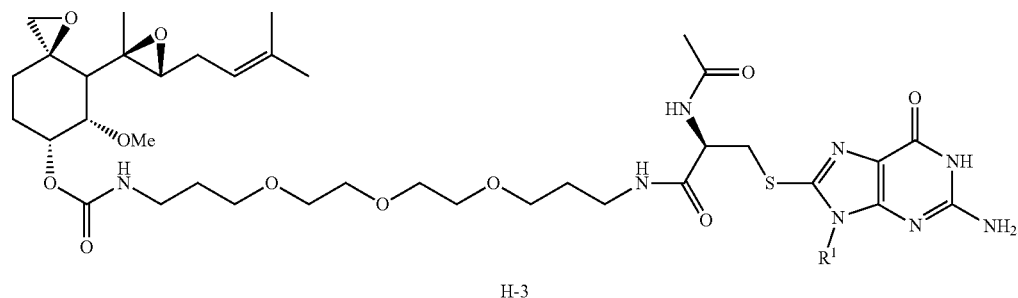

wherein each symbol is as defined above.

Compound (H-2) can be produced through the amidation reaction of compound (H-1) with carboxylic acid known in the art (XIa; ACS Chemical Biology, 10 (11), 2441-2447, 2015).

Compound (H-3) can be produced through the carbamation reaction of compound (H-1) with fumagillol.

Compound (H-1) can be produced through the amidation reaction of compound (A-9) ($R^{2a}$=$NH_2$)) with amine form (IXa).

Compounds (I-2), (I-4), and (I-6), which are included in compound (I), can be produced by the following method from compound (A-6 ($R^{2a}$=$NH_2$)).

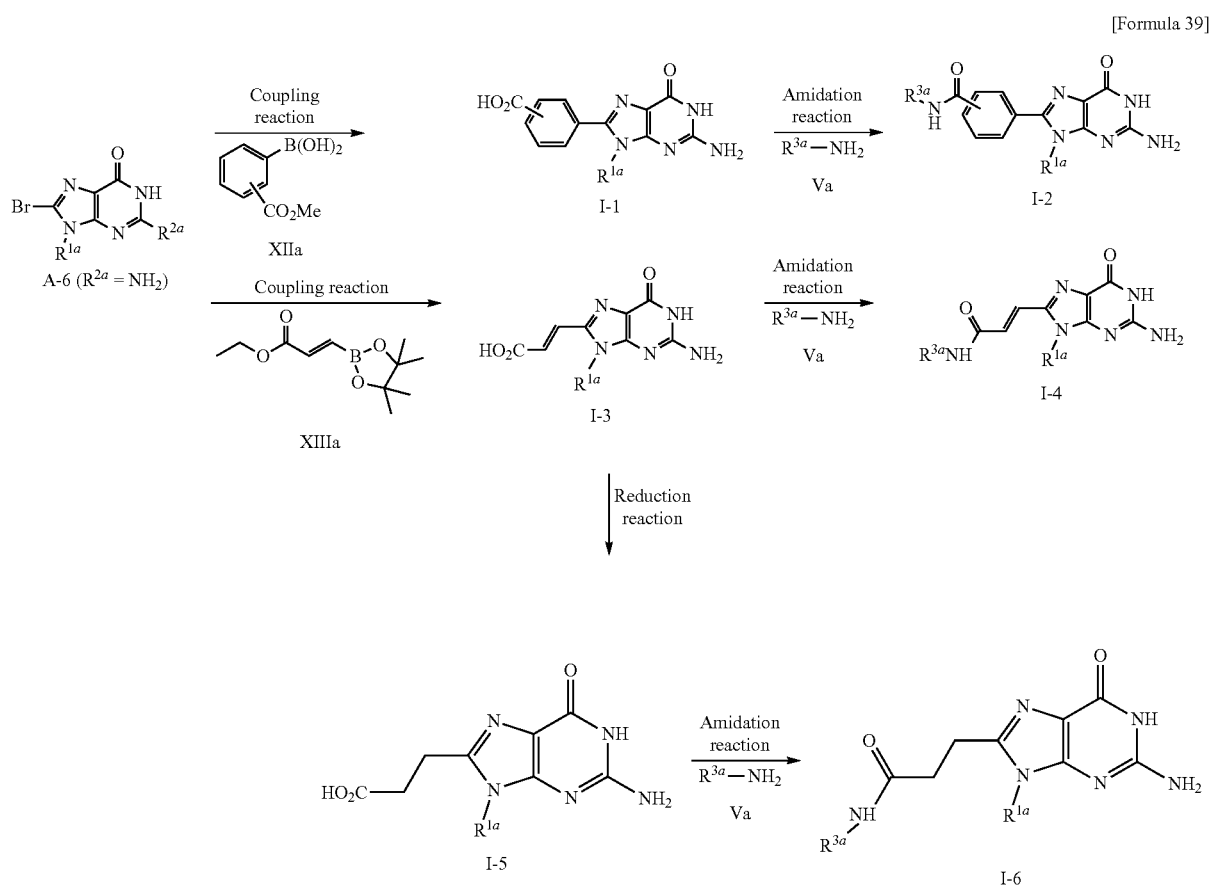

wherein each symbol is as defined above.

Compound (I-2) can be produced through the amidation reaction of compound (I-1) with amine form (Va).

Compound (I-1) can be produced through the coupling reaction of compound (A-6 ($R^{2a}$=$NH_2$)) with boronic acid (XIIa).

Compound (I-4) can be produced through the amidation reaction of compound (I-3) with amine form (Va).

Compound (I-3) can be produced through the coupling reaction of compound (A-6 ($R^{2a}$=$NH_2$)) with boronic acid ester (XIIIa).

Compound (I-6) can be produced through the amidation reaction of compound (I-5) with amine form (Va).

Compound (I-5) can be produced through the reduction reaction of compound (I-3).

Compounds (L-1) to (L-10), which are included in compound (I), can be produced by the following method from compound (A-6 ($R^{2a}$=$NH_2$)).

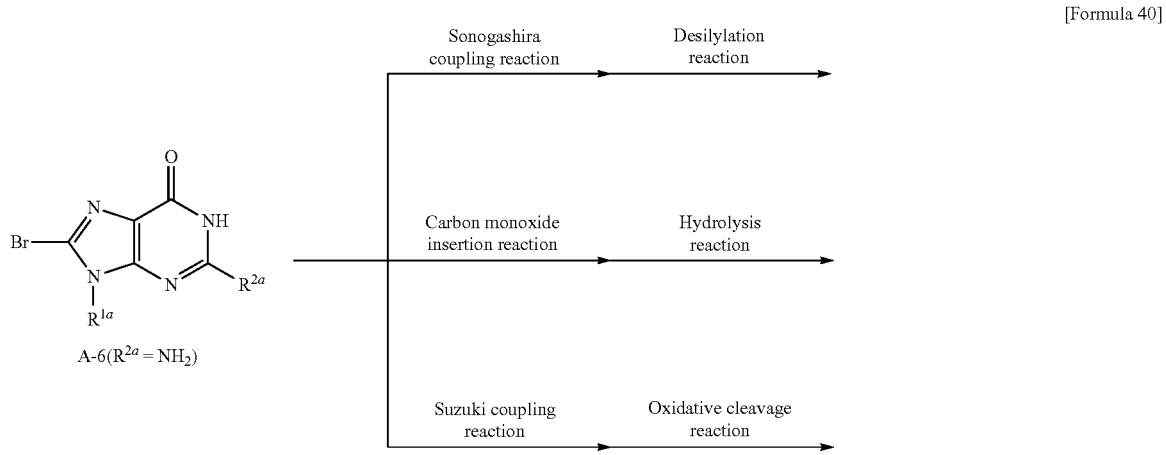

-continued
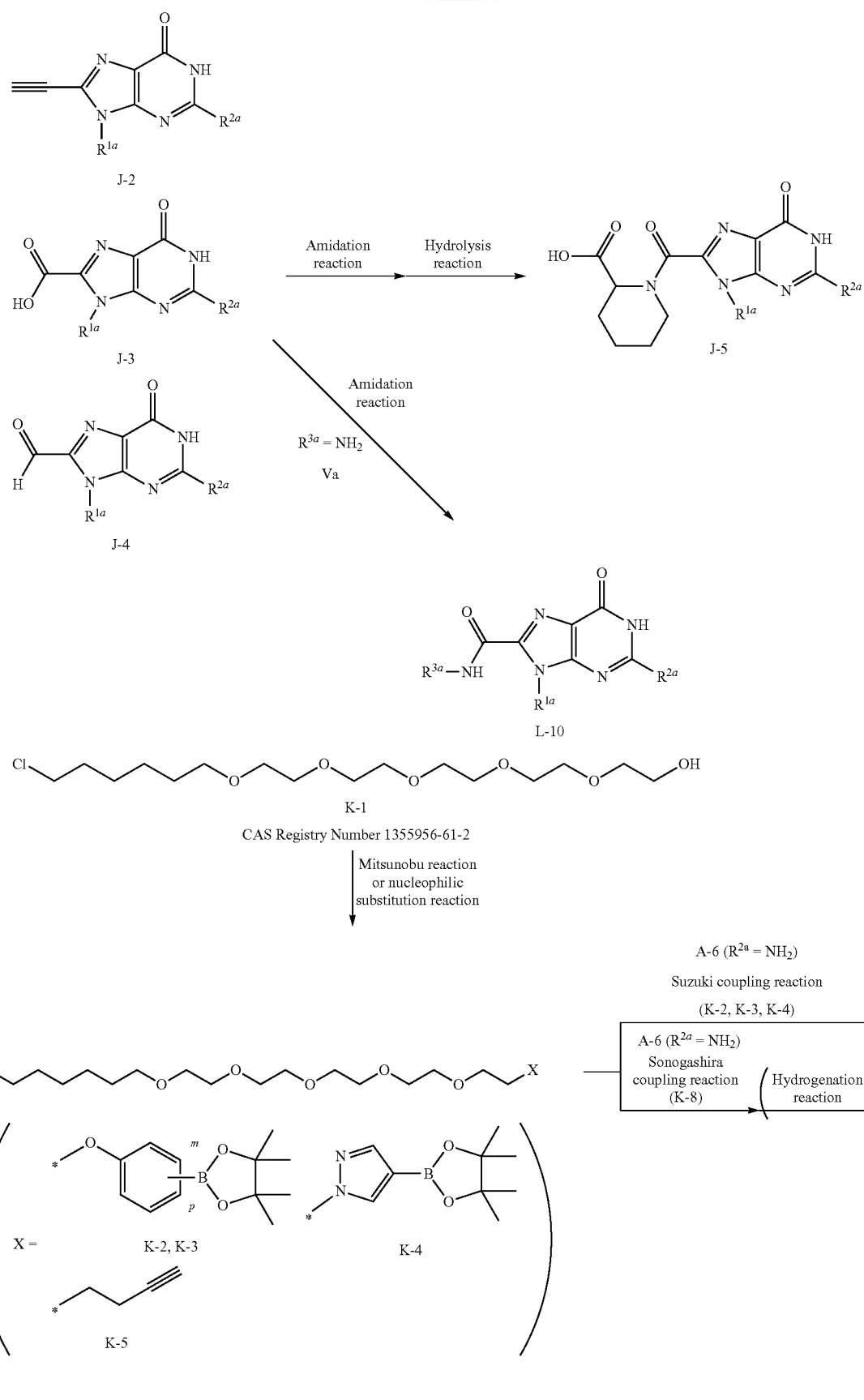

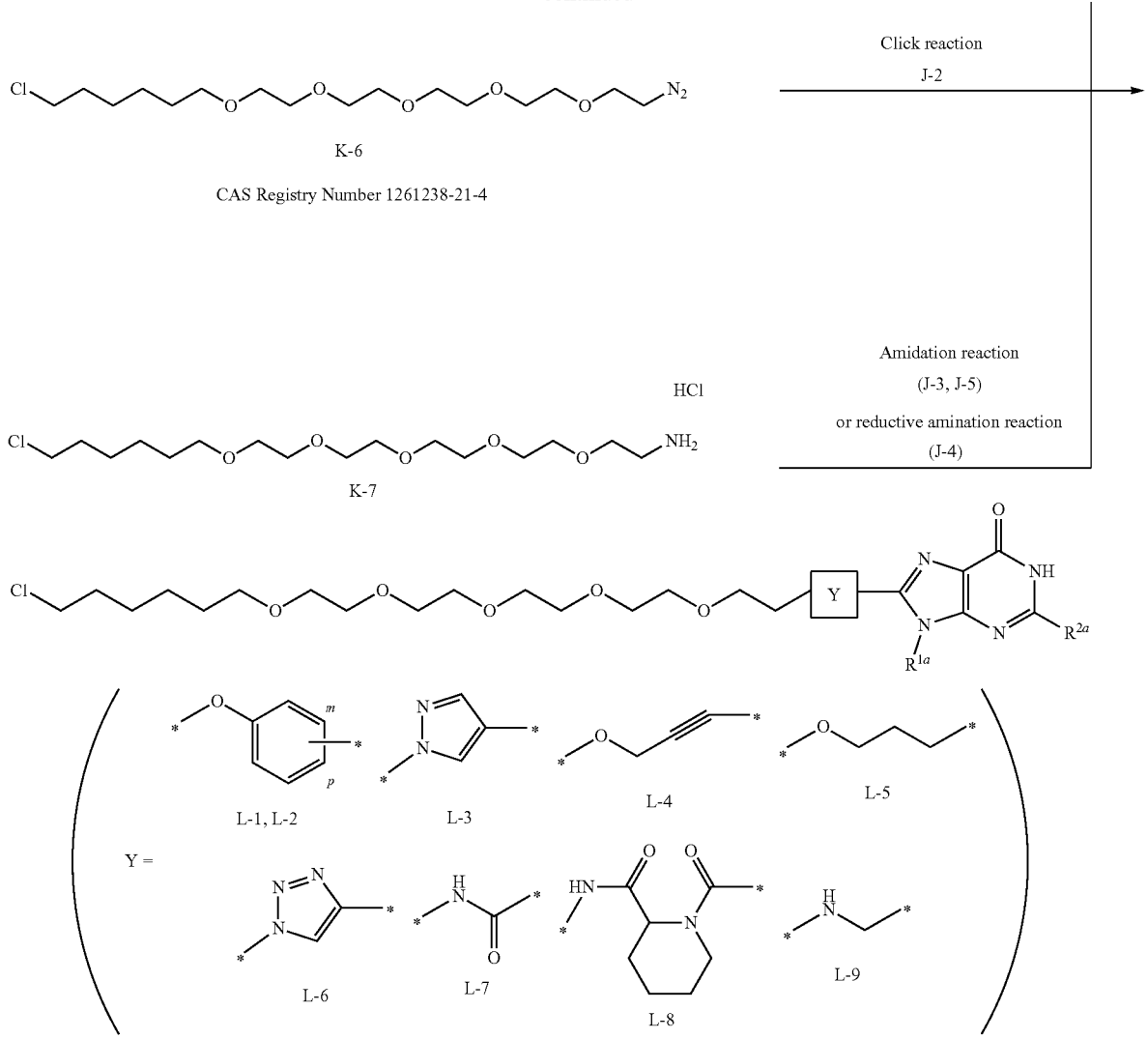

wherein each symbol is as defined above.

Compounds (L-1) to (L-3) can be produced through the Suzuki coupling reaction of compound (A-6 ($R^{2a}$=NH$_2$)) with boronic acid ester derivatives (K-2) to (K-4).

Boronic acid esters (K-2) to (K-4) can be produced through the Mitsunobu reaction of compound (K-1) known in the art.

Compound (L-4) can be produced through the Sonogashira coupling reaction of compound (A-6 ($R^{2a}$=NH$_2$)) with alkyne form (K-5).

Alkyne form (K-5) can be produced through the nucleophilic substitution reaction of compound (K-1) known in the art with propargyl p-toluenesulfonate.

Compound (L-5) can be produced through the hydrogenation reaction of compound (L-4).

Compound (L-6) can be produced through the Click reaction of compound (K-6) known in the art with alkyne derivative (J-2).

Alkyne form (J-2) can be produced through the Sonogashira coupling reaction of compound (A-6 ($R^{2a}$=NH$_2$)) with trimethylsilylacetylene, followed by desilylation reaction (deprotection reaction).

Compounds (L-7) and (L-8) can be produced through the amidation reaction of amine form (K-7) with carboxylic acid derivatives (J-3) and (J-5).

Compound (J-3) can be produced through the carbon monoxide insertion reaction of compound (A-6 ($R^{2a}$=NH$_2$)), followed by hydrolysis reaction.

Compound (J-5) can be produced through the amidation reaction of compound (J-3) with methyl pipecolate hydrochloride, followed by hydrolysis reaction.

Compound (L-9) can be produced through the reductive amination reaction of amine form (K-7) with aldehyde form (J-4).

Compound (J-4) can be produced through the Suzuki coupling reaction of compound (A-6 ($R^{2a}$=NH$_2$)) with 4,4,5,5-tetramethyl-2-vinyl-1,3,2-dioxaborolane, followed by oxidative cleavage reaction.

Compound (L-10) can be produced through the amidation reaction of compound (J-3) with amine form (Va).

When compound (I) has isomers such as optical isomers, stereoisomers, positional isomers, and rotational isomers, one of the isomers and an isomeric mixture thereof are also included in compound (I). For example, when compound (I) has optical isomers, optical isomers resolved from a racemate are also included in compound (I). These isomers can each be obtained as a single compound by a synthesis approach and a separation approach (e.g., concentration, solvent extraction, column chromatography, and recrystallization), known per se in the art.

Compound (I) may be crystals. A single crystal form and a polymorphic mixture are included in compound (I). The crystals can be produced through crystallization by the application of a crystallization method known per se in the art.

Compound (I) may be a pharmaceutically acceptable cocrystal or cocrystal salt. In this context, the cocrystal or the cocrystal salt means a crystalline substance constituted by two or more unique substances that are solids at room temperature and differ in physical properties (e.g., structure, melting point, heat of melting, hygroscopicity, and stability). The cocrystal and the cocrystal salt can be produced according to a cocrystallization method known per se in the art.

Compound (I) may be a hydrate or a non-hydrate or may be a solvate or a non-solvate, all of which are included in compound (I).

A compound labeled with an isotope (e.g., $^{2}H$, $^{3}H$, $^{11}C$, $^{14}C$, $^{18}F$, $^{35}S$, and $^{125}I$) or the like is also included in compound (I). Compound (I) labeled or substituted with an isotope can be used as, for example, a tracer (PET tracer) for use in positron emission tomography (PET), and is useful in the fields of medical diagnosis and the like.

Compound (I) wherein $R^1$ is a ligand for an intracellular protein fused with HaloTag® can be used as, for example, a tool for analyzing the mechanism of autophagic degradation of the intracellular protein.

Compound (I) wherein $R^1$ is a ligand for an intracellular protein related to a pathological condition can be used as a tool for analyzing the mechanism of the pathological condition and can also be used as a prophylactic and/or therapeutic drug for the pathological condition.

Compound (I) wherein $R^1$ is a ligand for an intracellular protein related to a pathological condition (in the present specification, also referred to as compound (II)) may be a prodrug.

The prodrug of compound (II) refers to a compound that is converted to the compound (II) through a reaction caused by an enzyme, gastric acid, or the like under physiological conditions in vivo, i.e., a compound that is converted to the compound (II) by enzymatic oxidation, reduction, hydrolysis, etc., or a compound that is converted to the compound (II) by hydrolysis, etc., caused by gastric acid or the like.

Examples of the prodrug of compound (II) include:
(1) a compound in which amino of the compound (II) is acylated, alkylated, or phosphorylated (e.g., a compound in which amino of the compound (II) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, tert-butylated, ethoxycarbonylated, tert-butoxycarbonylated, acetylated, or cyclopropylcarbonylated);
(2) a compound in which hydroxy of the compound (II) is acylated, alkylated, phosphorylated, or borated (e.g., a compound in which hydroxy of the compound (II) is acetylated, palmitoylated, propanoylated, pivaloylated, succinylated, fumarylated, alanylated, or dimethylaminomethylcarbonylated); and
(3) a compound in which carboxy of the compound (II) is esterified or amidated (e.g., a compound in which carboxy of the compound (II) is ethyl-esterified, phenyl-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolen-4-yl)methyl-esterified, cyclohexyloxycarbonylethyl-esterified, or methylamidated). These compounds can be produced from the compound (II) by a method known per se in the art.

The prodrug of compound (II) may be converted to the compound (II) under physiological conditions as described in Iyakuhin No Kaihatsu (Development of Pharmaceuticals in English), Vol. 7, Molecular Design, p. 163-198, Hirokawa Shoten Ltd. (1990).

The compound (II) or the prodrug thereof (in the present specification, these are also collectively referred to as the "compound of the present invention") has the activity of inducing degradation of a targeted intracellular molecule (preferably intracellular protein, particularly, intracellular protein related to a pathological condition) and is useful as a prophylactic or therapeutic agent for a disease involving the targeted intracellular molecule. The compound of the present invention can be effective for the prevention or treatment of every disease involving the targeted intracellular molecule according to the mechanism of action thereof. Among others, the compound of the present invention is expected to be effective for the treatment or prevention of cancers, inflammatory diseases, autoimmune diseases and bone or joint degenerative diseases.

Examples of the therapeutic or prophylactic agent for a cancer include prophylactic or therapeutic agents for colorectal cancer (e.g., colon cancer, rectal cancer, anus cancer, familial colorectal cancer, hereditary non-polyposis colorectal cancer, and gastrointestinal stromal tumor), lung cancer (e.g., non-small cell lung cancer, small-cell lung cancer, and malignant mesothelioma), mesothelioma, pancreatic cancer (e.g., ductal pancreatic cancer and pancreatic endocrine tumor), throat cancer, voice box cancer, esophageal cancer, stomach cancer (e.g., papillary adenocarcinoma, mucous adenocarcinoma, and adenosquamous carcinoma), duodenal cancer, small intestine cancer, breast cancer (e.g., invasive ductal breast cancer, noninvasive ductal breast cancer, and inflammatory breast cancer), ovarian cancer (e.g., epithelial ovarian cancer, extragonadal germ cell tumor, ovarian germ cell tumor, and ovarian tumor of low malignant potential), testicular tumor, prostate cancer (e.g., hormone-dependent prostate cancer, hormone-independent prostate cancer, and castration-resistant prostate cancer), liver cancer (e.g., hepatocellular carcinoma, primary liver cancer, and extrahepatic bile duct cancer), thyroid cancer (e.g., medullary thyroid cancer), kidney cancer (e.g., renal cell cancer (e.g., clear cell renal cell carcinoma) and transitional cell cancer of the renal pelvis and ureter), uterine cancer (e.g., uterine cervical cancer, uterine body cancer, and uterine sarcoma), gestational choriocarcinoma, brain tumor (e.g., medulloblastoma, glioma, pineal astrocytoma, pilocytic astrocytoma, diffuse astrocytoma, anaplastic astrocytoma, and pituitary adenoma), retinoblastoma, skin cancer (e.g., basalioma and malignant melanoma), sarcoma (e.g., rhabdomyosarcoma, leiomyosarcoma, soft tissue sarcoma, and spindle cell sarcoma), malignant bone tumor, bladder cancer, blood cancer (e.g., multiple myeloma, leukemia, malignant lymphoma, Hodgkin disease, and chronic myeloproliferative disease), primary unknown cancer, and the like, cancer growth inhibitors, cancer metastasis inhibitors, apoptosis promoters, and therapeutic agents for premalignant lesions (e.g., myelodysplastic syndrome).

Among others, the compound of the present invention is particularly effective for multiple myeloma, acute myeloid leukemia, colorectal cancer, and pancreatic cancer.

The compound of the present invention can be used for treating or preventing the diseases described above in a mammal (e.g., mice, rats, hamsters, rabbits, cats, dogs, cattle, sheep, monkeys, and humans).

The compound of the present invention can be orally or parenterally administered alone or as a mixture with a pharmacologically acceptable carrier as a medicament to a mammal (preferably a human)

Hereinafter, the medicament comprising the compound of the present invention (also referred to as the "medicament of the present invention") will be described in detail. Examples of the dosage form of the medicament of the present invention include oral preparations such as tablets (including sugar-coated tablets, film-coated tablets, sublingual tablets, buccal tablets and rapidly orally disintegrating tablets), pills, granules, powders, capsules (including soft capsules and microcapsules), syrups, emulsions, suspensions, and films (e.g., orally disintegrating films and patch films for application to the oral mucosa). Examples of the dosage form of the medicament of the present invention also include parenteral preparations such as injections, transfusions, transdermal preparations (e.g., iontophoresis dermal preparations), suppositories, ointments, transnasal preparations, transpulmonary preparations, and eye drops. Alternatively, the medicament of the present invention may be a controlled-release formulation such as a rapid-release formulation or a sustained-release formulation (including a sustained-release microcapsule).

The medicament of the present invention can be produced by a production method known in the art (e.g., a method described in Japanese Pharmacopoeia) generally used in the field of pharmaceutical technology. The medicament of the present invention can contain, if necessary, an appropriate amount of an additive usually used in the pharmaceutical field, such as an excipient, a binder, a disintegrant, a lubricant, a sweetener, a surfactant, a suspending agent, an emulsifier, a colorant, a preservative, a fragrance, a taste masking agent, a stabilizer, or a viscosity modifier.

Examples of the pharmacologically acceptable carrier described above include these additives.

For example, the tablets can be produced using an excipient, a binder, a disintegrant, a lubricant, and the like. The pills and the granules can be produced using an excipient, a binder and a disintegrant. The powders and the capsules can be produced using an excipient and the like. The syrups can be produced using a sweetener and the like. The emulsions or the suspensions can be produced using a suspending agent, a surfactant, an emulsifier, and the like.

Examples of the excipient include lactose, saccharose, glucose, starch, sucrose, microcrystalline cellulose, licorice powders, mannitol, sodium bicarbonate, calcium phosphate, and calcium sulfate.

Examples of the binder include a solution containing 5 to 10% by weight of starch paste, a solution containing 10 to 20% by weight of gum arabic or gelatin, a solution containing 1 to 5% by weight of tragacanth, a carboxymethylcellulose solution, a sodium alginate solution and glycerin.

Examples of the disintegrant include starch and calcium carbonate.

Examples of the lubricant include magnesium stearate, stearic acid, calcium stearate, and purified talc.

Examples of the sweetener include glucose, fructose, invert sugar, sorbitol, xylitol, glycerin, and simple syrup.

Examples of the surfactant include sodium lauryl sulfate, polysorbate 80, sorbitan monofatty acid ester, and polyoxyl 40 stearate.

Examples of the suspending agent include gum arabic, sodium alginate, carboxymethylcellulose sodium, methylcellulose, and bentonite.

Examples of the emulsifier include gum arabic, tragacanth, gelatin, and polysorbate 80.

When the medicament of the present invention is, for example, tablets, the tablets can be produced according to a method known per se in the art by adding, for example, an excipient (e.g., lactose, saccharose, and starch), a disintegrant (e.g., starch and calcium carbonate), a binder (e.g., starch, gum arabic, carboxymethylcellulose, polyvinylpyrrolidone, and hydroxypropylcellulose) or a lubricant (e.g., talc, magnesium stearate, and polyethylene glycol 6000) to the compound of the present invention, followed by compression and, if necessary, subsequent coating by a method known per se in the art for the purpose of taste masking, enteric properties or durability. For example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (manufactured by Rohm GmbH, Germany, methacrylic acid-acrylic acid copolymer) and a dye (e.g., iron red and titanium dioxide) are used as coating agents for the coating.

The injections include intravenous injections as well as subcutaneous injections, intracutaneous injections, intramuscular injections, intraperitoneal injections, drip injections, and the like.

Such injections are prepared by a method known per se in the art, i.e., by dissolving, suspending or emulsifying the compound of the present invention in a sterile aqueous solution or oily solution. Examples of the aqueous solution include saline, and an isotonic solution containing glucose or an additional adjuvant (e.g., D-sorbitol, D-mannitol, and sodium chloride). The aqueous solution may contain an appropriate solubilizing agent, for example, an alcohol (e.g., ethanol), a polyalcohol (e.g., propylene glycol and polyethylene glycol), or a nonionic surfactant (e.g., polysorbate 80 and HCO-50). Examples of the oily solution include sesame oil and soybean oil. The oily solution may contain an appropriate solubilizing agent. Examples of the solubilizing agent include benzyl benzoate and benzyl alcohol. The injections may be further supplemented with a buffer (e.g., a phosphate buffer solution and a sodium acetate buffer solution), a soothing agent (e.g., benzalkonium chloride and procaine hydrochloride), a stabilizer (e.g., human serum albumin and polyethylene glycol), a preservative (e.g., benzyl alcohol and phenol), or the like. Ampules are usually filled with the prepared injection solutions.

The content of the compound of the present invention in the medicament of the present invention differs depending on the form of the preparation and is usually about 0.01 to about 100% by weight, preferably about 2 to about 85% by weight, more preferably about 5 to about 70% by weight, with respect to the whole preparation.

The content of the additive in the medicament of the present invention differs depending on the form of the preparation and is usually about 1 to about 99.9% by weight, preferably about 10 to about 90% by weight, with respect to the whole preparation.

The compound of the present invention can be used stably, low toxically and safely. The daily dose of the compound of the present invention differs depending on the status and body weight of a patient, the type of the compound, an administration route, etc. In the case of, for example, oral administration to a patient for the purpose of treating a cancer, the daily dose in an adult (body weight: about 60 kg) is about 1 to about 1000 mg, preferably about 3 to about 300 mg, more preferably about 10 to about 200 mg, of the compound of the present invention, which can be administered in one portion or in two or three portions.

In the case of parenteral administration, the compound of the present invention is usually administered in the form of a liquid (e.g., an injection). The single dose of the compound of the present invention also differs depending on a recipient, a target organ, symptoms, an administration method, etc. For example, usually about 0.01 to about 100 mg, preferably about 0.01 to about 50 mg, more preferably about 0.01 to about 20 mg, of the compound of the present invention per kg of body weight is preferably administered by intravenous injection.

The compound of the present invention can be used in combination with an additional drug. Specifically, the compound of the present invention, when used as a therapeutic or prophylactic agent for various cancers, can be used in combination with a drug such as a hormone therapeutic, a chemotherapeutic, an immunotherapeutic, an agent inhibiting the effects of a cell growth factor and its receptor, or the like. Hereinafter, the drug that may be used in combination with the compound of the present invention is referred to as a concomitant drug.

Examples of the "hormone therapeutic" used include fosfestrol, diethylstilbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogen (e.g., tamoxifen citrate and toremifene citrate), contraceptive pills, mepitiostane, testololactone, aminoglutethimide, LH-RH agonists (e.g., goserelin acetate, buserelin, and leuprorelin acetate), droloxifene, epitiostanol, ethinyl estradiol sulfonate, aromatase inhibitors (e.g., fadrozole hydrochloride, anastrozole, letrozole, exemestane, vorozole, and formestane), anti-androgen (e.g., flutamide, bicalutamide, nilutamide, and enzalutamide), 5α-reductase inhibitors (e.g., finasteride, episteride, and dutasteride), adrenal corticosteroid agents (e.g., dexamethasone, prednisolone, betamethasone, and triamcinolone), androgen synthesis inhibitors (e.g., abiraterone), retinoid and agents delaying retinoid metabolism (e.g., liarozole), thyroid hormones, and DDS (drug delivery system) preparations thereof.

Examples of the "chemotherapeutic" used include alkylating agents, antimetabolites, anticancer antibiotics, and plant-derived anticancer agents.

Examples of the "alkylating agent" used include nitrogen mustard, nitrogen mustard-N-oxide hydrochloride, chlorambucil, cyclophosphamide, ifosfamide, thiotepa, carboquone, improsulfan tosylate, busulfan, nimustine hydrochloride, mitobronitol, melphalan, dacarbazine, ranimustine, estramustine sodium phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, Ribomustin, temozolomide, treosulfan, trofosfamide, zinostatin stimalamer, adozelesin, cystemustine, bizelesin, and DDS preparations thereof.

Examples of the "antimetabolite" used include mercaptopurine, 6-mercaptopurine riboside, thioinosine, methotrexate, pemetrexed, enocitabine, cytarabine, cytarabine ocfosfate, ancitabine hydrochloride, 5-FU drugs (e.g., fluorouracil, tegafur, UFT, doxifluridine, carmofur, galocitabine, emitefur, and capecitabine), aminopterin, nelarabine, leucovorin calcium, Tabloid, butocin, calcium folinate, calcium levofolinate, cladribine, emitefur, fludarabine, gemcitabine, hydroxycarbamide, pentostatin, piritrexim, idoxuridine, mitoguazone, tiazofurin, ambamustine, bendamustine, and DDS preparations thereof.

Examples of the "anticancer antibiotic" used include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride, and DDS preparations (e.g., PEG liposomal doxorubicin) thereof.

Examples of the "plant-derived anticancer agent" used include etoposide, etoposide phosphate, vinblastine sulfate, vincristine sulfate, vindesine sulfate, teniposide, paclitaxel, docetaxel, cabazitaxel, vinorelbine, and DDS preparations thereof.

Examples of the "immunotherapeutic" used include picibanil, Krestin, schizophyllan, lentinan, ubenimex, interferon, interleukin, macrophage colony-stimulating factor, granulocyte colony-stimulating factor, erythropoietin, lymphotoxin, BCG vaccines, *Corynebacterium parvum*, levamisole, polysaccharide K, procodazol, anti-CTLA4 antibodies (e.g., ipilimumab and tremelimumab), anti-PD-1 antibodies (e.g., nivolumab and pembrolizumab), and anti-PD-L1 antibodies.

The "cell growth factor" in the "agent inhibiting the effects of a cell growth factor and its receptor" can be any substance that promotes the growth of cells. Examples of the cell growth factor used typically include a factor that is a peptide having a molecular weight of 20,000 or smaller and exerts its effects at a low concentration through binding to its receptor, and specifically include (1) EGF (epidermal growth factor) or a substance having activity substantially identical thereto [e.g., TGFα], (2) insulin or a substance having activity substantially identical thereto [e.g., insulin, IGF (insulin-like growth factor)-1, and IGF-2], (3) FGF (fibroblast growth factor) or a substance having activity substantially identical thereto [e.g., acidic FGF, basic FGF, KGF (keratinocyte growth factor), and FGF-10], and (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), heregulin, and angiopoietin].

The "receptor of the cell growth factor" can be any receptor having the ability to bind to the cell growth factor described above. Specifically, EGF receptor, heregulin receptor (e.g., HER3), insulin receptor, IGF receptor-1, IGF receptor-2, FGF receptor-1 or FGF receptor-2, VEGF receptor, angiopoietin receptor (e.g., Tie2), PDGF receptor, or the like is used.

Examples of the "agent inhibiting the effects of a cell growth factor and its receptor" used include EGF inhibitors, TGFα inhibitors, heregulin inhibitors, insulin inhibitors, IGF inhibitors, FGF inhibitors, KGF inhibitors, CSF inhibitors, EPO inhibitors, IL-2 inhibitors, NGF inhibitors, PDGF inhibitors, TGFβ inhibitors, HGF inhibitors, VEGF inhibitors, angiopoietin inhibitors, EGF receptor inhibitors, HER2 inhibitors, HER4 inhibitors, insulin receptor inhibitors, IGF-1 receptor inhibitors, IGF-2 receptor inhibitors, FGF receptor-1 inhibitors, FGF receptor-2 inhibitors, FGF receptor-3 inhibitors, FGF receptor-4 inhibitors, VEGF receptor inhibitors, Tie-2 inhibitors, PDGF receptor inhibitors, ABL inhibitors, Raf inhibitors, FLT3 inhibitors, c-Kit inhibitors, Src inhibitors, PKC inhibitors, Smo inhibitors, ALK inhibitors, ROR1 inhibitors, Trk inhibitors, Ret inhibitors, mTOR inhibitors, Aurora inhibitors, PLK inhibitors, MEK (MEK1/2) inhibitors, MET inhibitors, CDK inhibitors, Akt inhibitors, ERK inhibitors, and PI3K inhibitors. More specific examples thereof include anti-VEGF antibodies (e.g., bevacizumab and ramucirumab), anti-HER2 antibodies (e.g., trastuzumab and pertuzumab), anti-EGFR antibodies (e.g., cetuximab, panitumumab, matuzumab, and nimotuzumab), anti-HGF antibodies, imatinib, erlotinib, gefitinib, sorafenib, sunitinib, dasatinib, lapatinib, vatalanib, ibrutinib, bosutinib, cabozantinib, crizotinib, alectinib, vismodegib, cediranib, tivantinib, quizartinib, dovitinib, axitinib, motesanib, nilotinib, 6-[4-(4-ethylpiperazin-1-ylmethyl)phenyl]-N-[1(R)-phenylethyl]-7H-pyrrolo[2,3-d]pyrimidin-4-amine (AEE-788), vandetanib, temsirolimus, everolimus, enzastaurin, tozasertib, phosphoric acid 2-[N-[3-[4-[5-[N-(3-fluorophenyl)carbamoylmethyl]-1H-pyrazol-3-ylamino]quinazolin-7-yloxy]propyl]-N-ethylamino]ethyl ester (AZD-1152), 4-[9-chloro-7-(2,6-difluorophenyl)-5H-pyrimido[5,4-d][2]benzazapin-2-ylamino]benzoic acid, N-[2-methoxy-5-[(E)-2-(2,4,6-trimethoxyphenyl)vinylsulfonylmethyl]phenyl] glycine sodium salt (ON-1910Na), volasertib, selumetinib, trametinib, N-[2(R),3-dihydroxypropoxy]-3,4-difluoro-2-(2-fluoro-4-iodophenylamino)benzamide (PD-0325901), bosutinib, regorafenib, afatinib, idelalisib, ceritinib, and dabrafenib.

In addition to the drugs described above, L-asparaginase, L-arginase, arginine deiminase, aceglatone, procarbazine hydrochloride, protoporphyrin-cobalt complex salt, mercury hematoporphyrin-sodium, topoisomerase I inhibitors (e.g., irinotecan, topotecan, indotecan, and indimitecan), topoisomerase II inhibitors (e.g., sobuzoxane), differentiation inducers (e.g., retinoid and vitamins D), angiogenesis inhibitors (e.g., fumagillin, shark extracts, and COX-2 inhibitors), α-blockers (e.g., tamsulosin hydrochloride), bisphosphonic acids (e.g., pamidronate and zoledronate), thalidomide, lenalidomide, pomalidomide, 5-azacytidine, decitabine, proteasome inhibitors (e.g., bortezomib, carfilzomib, and ixazomib), NEDD8 inhibitors (e.g., pevonedistat), UAE inhibitors, PARP inhibitors (e.g., olaparib, niraparib, and veliparib), antitumor antibodies such as anti-CD20 antibodies (e.g., rituximab and obinutuzumab) and anti-CCR4 antibodies (e.g., mogamulizumab), antibody-drug conjugates (e.g., trastuzumab emtansine, and brentuximab vedotin), or the like can also be used as the concomitant drug.

The combination of the compound of the present invention and the concomitant drug can produce excellent effects such as: (1) the dose of the compound of the present invention or the concomitant drug can be reduced as compared with the administration of the compound of the present invention or the concomitant drug alone; (2) the drug for combined use with the compound of the present invention can be selected according to the symptoms (mild, serious, etc.) of a patient; (3) the treatment duration can be set longer; (4) a sustained therapeutic effect can be achieved; and (5) a synergistic effect can be obtained by the combined use of the compound of the present invention and the concomitant drug.

Hereinafter, the combined use of the compound of the present invention and the concomitant drug is referred to as the "combination drug of the present invention".

For use of the combination drug of the present invention, the times of administration of the compound of the present invention and the concomitant drug are not limited, and the compound of the present invention and the concomitant drug may be administered concurrently or in a staggered manner to a recipient. In the case of administration in a staggered manner, the staggered manner differs depending on active ingredients to be administered, a dosage form, and an administration method. In the case of first administering, for example, the concomitant drug, the compound of the present invention can be administered within 1 minute to 3 days, preferably within 10 minutes to 1 day, more preferably within 15 minutes to 1 hour, after the administration of the concomitant drug. In the case of first administering the compound of the present invention, the concomitant drug can be administered within 1 minute to 1 day, preferably within 10 minutes to 6 hours, more preferably within 15 minutes to 1 hour, after the administration of the compound of the present invention. The dose of the concomitant drug can abide by a dose clinically used and can be appropriately selected according to a recipient, an administration route, a disease, a combination, etc.

Examples of the administration mode of the compound of the present invention and the concomitant drug used in combination include (1) the administration of a single preparation obtained by concurrently formulating the compound of the present invention and the concomitant drug, (2) the concurrent administration through the same administration route of two preparations obtained by separately formulating the compound of the present invention and the concomitant drug, (3) the administration through the same administration route in a staggered manner of two preparations obtained by separately formulating the compound of the present invention and the concomitant drug, (4) the concurrent administration through different administration routes of two preparations obtained by separately formulating the compound of the present invention and the concomitant drug, and (5) the administration through different administration routes in a staggered manner of two preparations obtained by separately formulating the compound of the present invention and the concomitant drug (e.g., administration in the order of the compound of the present invention and then the concomitant drug, or in the reverse order).

The dose of the concomitant drug can be appropriately selected on the basis of a dose clinically used. The mixing ratio between the compound of the present invention and the concomitant drug can be appropriately selected according to a recipient, an administration route, a target disease, symptoms, a combination, etc. When the recipient is, for example, a human, 0.01 to 100 parts by weight of the concomitant drug can be used with respect to 1 part by weight of the compound of the present invention.

The compound of the present invention or the combination drug of the present invention can be further used in combination with a non-drug therapy. Specifically, the compound of the present invention or the combination drug of the present invention may be combined with a non-drug therapy, for example, (1) surgery, (2) induced hypertension chemotherapy using angiotensin II or the like, (3) gene therapy, (4) thermotherapy, (5) cryotherapy, (6) laser cauterization, or (7) radiotherapy.

The compound of the present invention or the combination drug of the present invention is used, for example, before or after the surgery or the like or before or after treatment involving two or three of these therapies in combination to produce effects such as prevention of development of resistance, prolonged disease-free survival, inhibition of cancer metastasis or recurrence, and life prolongation.

Also, the treatment with the compound of the present invention or the combination drug of the present invention may be combined with supportive care [(i) the administration of an antibiotic (e.g., β-lactam antibiotics such as Pansporin, and macrolide antibiotics such as clarithromycin) against various intercurrent infections, (ii) the administration of a high-calorie infusion, an amino acid preparation or multivitamin for the improvement of malnutrition, (iii) the administration of morphine for pain relief, (iv) the administration of a drug improving adverse reactions such as nausea, vomiting, anorexia, diarrhea, leukopenia, thrombocytopenia, decreased hemoglobin concentration, alopecia, liver damage, kidney damage, DIC, or fever, and (v) the administration of a drug for inhibiting the multidrug resistance of a cancer].

EXAMPLES

The present invention will be further described in detail by Examples, Test Examples and Preparation Examples given below. However, these are not intended to limit the present invention and may be changed or modified without departing from the scope of the present invention.

In Examples given below, "room temperature" usually refers to about 10° C. to about 35° C. The ratio shown in a mixed solvent refers to a volume ratio, unless otherwise specified. "%" refers to % by weight, unless otherwise specified.

The elution in column chromatography in Examples was carried out under observation by TLC (thin layer chromatography), unless otherwise specified. In the TLC observation, 60 $F_{254}$ manufactured by Merck was used as a TLC plate, and a solvent used as an elution solvent in column chromatography was used as a development solvent. Also, detection employed a UV detector or was carried out by dipping in the following: (b) a solution of 7% phosphomolybdic acid in ethanol (prepared from 500 mL of 95% ethanol and 35 g of phosphomolybdic acid) or a p-anisaldehyde solution (prepared from 340 mL of ethanol, 9.3 mL of p-anisaldehyde, 3.8 mL of acetic acid, and 12.5 mL of concentrated sulfuric acid) and color development by heating on a hot plate. When NH was described in silica gel column chromatography, aminopropylsilane-bonded silica gel was used. When C18 was described in preparative HPLC (high-performance liquid chromatography), octadecyl-bonded silica gel was used. The ratio shown in an elution solvent refers to a volume ratio, unless otherwise specified.

"Osmium oxide (immobilized catalyst I)" in Examples refers to osmium(VIII) oxide (content of about 7%) immobilized on a highly solvent-resistant polymer commercially available from Wako Pure Chemical Industries, Ltd., unless otherwise specified.

ACD/SpecManager (brand name) software or the like was used in $^1$H NMR analysis. Very gentle peaks of protons of a hydroxyl group, an amino group, or the like may not be described.

MS was measured by LC/MS. An ESI method or an APCI method was used as an ionization method. Data was indicated by a found value. A molecular ion peak is usually observed, but may be of a fragment ion. In the case of a salt, a molecular ion peak or a fragment ion peak of a free from is usually observed. Alternatively, high-resolution mass spectrometry (HRMS) was used. Bruker micro Tof focus (ESI-TOF) was used in measurement. Acetonitrile or methanol was used in sample preparation. Fast atom bombardment mass spectrometry (FAB MS) measurement was carried out using JEOL LMS-700 manufactured by JEOL Ltd. and 3-nitrobenzyl alcohol added as matrix.

The following abbreviations are used in Examples given below.
MS: mass spectrum
M: molar concentration
N: normal
CDCl$_3$: deuterated chloroform
CD$_3$OD: deuterated methanol
DMSO-d$_6$: deuterated dimethyl sulfoxide
$^1$H NMR: proton nuclear magnetic resonance
LC/MS: liquid chromatograph mass spectrometer
ESI: electrospray ionization
APCI: atmospheric pressure chemical ionization
HRMS: high-resolution mass spectrometry
HATU: 2-(7-azabenzotriazol-1-yl)-1,1,3,3-tetramethyluronium hexafluorophosphate
DPPA: diphenylphosphorylazide
TFA: trifluoroacetic acid
WSC: N-(3-(dimethylamino)propyl)-N'-ethylcarbodiimide
IPE: diisopropyl ether
DIPEA: N,N-diisopropylethylamine
DMA: N,N-dimethylacetamide
DMF: N,N-dimethylformamide
HOBt: 1H-benzotriazol-1-ol
HOBt·H$_2$O: 1H-benzotriazol-1-ol monohydrate
THF: tetrahydrofuran
MeOH: methanol
WSC·HCl: N-(3-(dimethylamino)propyl)-N'-ethylcarbodiimide monohydrochloride
Boc$_2$O: di-tert-butyl dicarbonate
DMSO: dimethyl sulfoxide
AcOH: acetic acid
TEA: triethylamine
DEAD: diethyl diazodicarboxylate
PPh$_3$: triphenylphosphine
NBS: N-bromosuccinimide
PyBOP: (benzotriazol-1-yloxy)tripyrrolidinophosphonium hexafluorophosphate Example 1

N$^2$-Acetyl-S-(2-amino-9-(4-chlorobenzyl)-6-oxo-6,9-dihydro-1H-purin-8-yl)-N-(21-chloro-3,6,9,12,15-pentaoxahenicos-1-yl)-L-cysteinamide A) 6-Chloro-9-(4-chlorobenzyl)-9H-purin-2-amine A mixture of 6-chloro-9H-purin-2-amine (1.00 g), 1-(bromomethyl)-4-chlorobenzene (1.70 g), potassium carbonate (2.45 g), and DMF (25 mL) was stirred at room temperature for 12 hours. The reaction mixture was diluted with water, followed by extraction with ethyl acetate. The organic layer was separated, washed with saturated saline, then dried over anhydrous sodium sulfate, and concentrated under reduced pressure. The residue was purified by silica gel column chromatography (dichloromethane/ethyl acetate) to obtain the title compound (1.30 g).
$^1$H NMR (400 MHz, DMSO-d$_6$) δ 5.29 (2H, s), 6.94 (2H, s), 7.24-7.31 (2H, m), 7.37-7.45 (2H, m), 8.22 (1H, s).

B) 2-Amino-9-(4-chlorobenzyl)-1,9-dihydro-6H-purin-6-one

A mixture of 6-chloro-9-(4-chlorobenzyl)-9H-purin-2-amine (1.30 g), formic acid (20 mL), and water (5 mL) was stirred at 75° C. for 2 hours. The reaction mixture was concentrated under reduced pressure and diluted with a saturated aqueous solution of sodium carbonate (20 mL). The resulting solid was collected by filtration, washed with water, and then dried under reduced pressure to obtain the title compound (1.10 g).

$^1$H NMR (400 MHz, DMSO-d$_6$) δ 5.26 (2H, s), 6.88 (2H, brs), 7.29-7.34 (2H, m), 7.40-7.46 (2H, m), 8.50 (1H, s), 11.17 (1H, brs).

C) 2-Amino-8-bromo-9-(4-chlorobenzyl)-1,9-dihydro-6H-purin-6-one

A mixture of 2-amino-9-(4-chlorobenzyl)-1,9-dihydro-6H-purin-6-one (1.10 g), NBS (1.07 g), and AcOH (25 mL) was stirred at room temperature for 12 hours. The reaction mixture was diluted with ethyl acetate (10 mL). The resulting precipitate was collected by filtration and suspended in a 10% aqueous sodium hydroxide solution (3 mL) and methanol. The solid was collected by filtration and dried to obtain the title compound (0.56 g).

MS: [M+H]$^+$ 353.9.

D) N$^2$-Acetyl-S-(2-amino-9-(4-chlorobenzyl)-6-oxo-6,9-dihydro-1H-purin-8-yl)-N-(21-chloro-3,6,9,12,15-pentaoxahenicos-1-yl)-L-cysteinamide To a mixture of 2-amino-8-bromo-9-(4-chlorobenzyl)-1,9-dihydro-6H-purin-6-one (35 mg), N-acetyl-L-cysteine (49 mg), and DMA (1 mL), potassium carbonate (83 mg) was added at room temperature. The mixture was stirred at 70° C. for 3 hours in a nitrogen atmosphere. The reaction mixture was diluted with methanol, and the residue was purified by HPLC (YMC Triart C18, mobile phase: water/acetonitrile (10 mM ammonium bicarbonate system)) and HPLC (YMC Triart C18, mobile phase: water/acetonitrile (system containing 0.1% TFA)). The obtained fraction was concentrated. To a mixture of the obtained product, 21-chloro-3,6,9,12,15-pentaoxahenicosan-1-amine (53 mg), DIPEA (105 uL), and DMA (1 mL), HATU (76 mg) was added at room temperature. The mixture was stirred at room temperature for 2 hours. The reaction mixture was purified by HPLC (YMC Triart C18, mobile phase: water/acetonitrile (10 mM ammonium bicarbonate system)) and HPLC (YMC Triart C18, mobile phase: water/acetonitrile (system containing 0.1% TFA)) to obtain the title compound (2.3 mg).

The 21-chloro-3,6,9,12,15-pentaoxahenicosan-1-amine can be synthesized by a method known per se in the art (e.g., a method described in Biotechniques, 2009, 47, 769-774).

$^1$H NMR (400 MHz, CD$_3$OD) δ 1.34-1.49 (4H, m), 1.59 (2H, dt, J=14.2, 6.8 Hz), 1.71-1.83 (2H, m), 1.99 (3H, s), 3.35-3.42 (4H, m), 3.44-3.82 (27H, m), 4.70 (1H, dd, J=8.4, 4.5 Hz), 5.21 (2H, s), 7.24-7.31 (2H, m), 7.33-7.39 (2H, m).

Example 2

3-((2-Amino-9-(4-fluorobenzyl)-6-oxo-6,9-dihydro-1H-purin-8-yesulfanyl)-N-(21-chloro-3,6,9,12,15-pentaoxahenicos-1-yl)propanamide

A) 6-Chloro-9-(4-fluorobenzyl)-9H-purin-2-amine

To a mixture of 6-chloro-9H-purin-2-amine (20.4 g) and DMSO (100 mL), potassium carbonate (20.0 g) was added at room temperature. The mixture was stirred at room temperature for 14 hours in a nitrogen atmosphere. Then, water (300 mL) was added to the mixture under ice cooling. The resulting crystals were collected by filtration and dissolved in a mixed solution of THF and ethyl acetate. Insoluble matter was filtered off, and the filtrate was washed with saturated saline, then dried over anhydrous sodium sulfate, and concentrated under reduced pressure. The obtained crystals were recrystallized from acetonitrile/water (10/1, 300 mL) to obtain the title compound (17.0 g).

MS: [M+H]$^+$ 278.1.

B) 2-Amino-9-(4-fluorobenzyl)-1,9-dihydro-6H-purin-6-one

To a solution of 6-chloro-9-(4-fluorobenzyl)-9H-purin-2-amine (16.8 g) in trifluoroacetic acid (60 mL), water (20 mL) was added under ice cooling, and the mixture was warmed to 50° C. in a nitrogen atmosphere. The mixture was stirred at 50° C. for 14 hours in a nitrogen atmosphere. Then, the mixture was concentrated under reduced pressure. Water (170 mL) was added to the residue, and the pH of the aqueous mixture was adjusted to 7 with an 8 N sodium hydroxide solution. The resulting crystals were collected by filtration and washed with water to obtain the title compound (15.6 g).

MS: [M+H]$^+$ 260.1.

C) 2-Amino-8-bromo-9-(4-fluorobenzyl)-1,9-dihydro-6H-purin-6-one

To a mixture of 2-amino-9-(4-fluorobenzyl)-1,9-dihydro-6H-purin-6-one (15.4 g), acetonitrile (160 mL) and water (160 mL), NBS (12.8 g) was added under ice cooling, and the mixture was warmed to room temperature in a nitrogen atmosphere. The mixture was stirred at room temperature for 18 hours in a nitrogen atmosphere. Then, the mixture was filtered, and the crystals were collected by filtration. The obtained crystals were added to a mixed solution of THF and MeOH. Insoluble matter was filtered off, and the filtrate was concentrated. The obtained crystals were repulp-washed with MeOH and then collected by filtration to obtain the title compound (15.1 g).

$^1$H NMR (300 MHz, DMSO-d$_6$) δ 5.15 (2H, s), 6.62 (2H, brs), 7.10-7.33 (4H, m), 10.74 (1H, s).

D) 3-42-Amino-9-(4-fluorobenzyl)-6-oxo-6,9-dihydro-1H-purin-8-yesulfanyl)-N-(21-chloro-3,6,9,12,15-pentaoxahenicos-1-yl)propanamide To a mixture of 2-amino-8-bromo-9-(4-fluorobenzyl)-1,9-dihydro-6H-purin-6-one (300 mg), potassium carbonate (809 mg) and DMSO (3 mL), 3-mercaptopropionic acid (0.232 mL) was added at room temperature, and the mixture was stirred at 60° C. for 8 hours in a nitrogen atmosphere. Water (9 mL) was added to the mixture, and insoluble matter was filtered off. The pH of the filtrate was adjusted to 4 with 6 N hydrochloric acid. The resulting crystals were collected by filtration and repulp-washed with MeOH to obtain a crude product (230 mg).

To a mixture of the crude product (36.3 mg), 21-chloro-3,6,9,12,15-pentaoxahenicosan-1-amine (53 mg), DIPEA (105 uL), and DMA (1 mL), HATU (76 mg) was added at room temperature. The mixture was stirred at room temperature for 2 hours. The reaction mixture was purified by HPLC (YMC Triart C18, mobile phase: water/acetonitrile (10 mM ammonium bicarbonate system)) and HPLC (YMC Triart C18, mobile phase: water/acetonitrile (system containing 0.1% TFA)) to obtain the title compound (17.6 mg).

$^1$H NMR (300 MHz, CD$_3$OD) δ 1.30-1.49 (4H, m), 1.51-1.66 (2H, m), 1.69-1.84 (2H, m), 2.65 (2H, t, J=6.7

Hz), 3.34-3.41 (4H, m), 3.44-3.65 (22H, m), 5.21 (2H, s), 7.07 (2H, t, J=8.6 Hz), 7.35 (2H, dd, J=7.9, 5.4 Hz).

Example 3

4-(2-Amino-9-(4-fluorobenzyl)-6-oxo-6,9-dihydro-1H-purin-8-yl)-N-(21-chloro-3,6,9,12,15-pentaoxahenicos-1-yl)benzamide A) 4-(2-Amino-9-(4-fluorobenzyl)-6-oxo-6,9-dihydro-1H-purin-8-yl)benzoic acid A mixture of 2-amino-8-bromo-9-(4-fluorobenzyl)-1,9-dihydro-6H-purin-6-one (300 mg), potassium carbonate (184 mg), triphenylphosphine-3,3',3"-trisulfonic acid trisodium salt hydrate (52 mg), palladium(II) acetate (10 mg), acetonitrile (2 mL), and water (1 mL) was stirred overnight at 100° C. The reaction mixture was brought back to room temperature, and the solution was rendered basic by the addition of a 2 M aqueous sodium hydroxide solution. After washing with ethyl acetate, the pH of the obtained aqueous layer was adjusted to 4 to 5 with 1 M hydrochloric acid. The resulting solid was collected by filtration and dried under reduced pressure to obtain the title compound (332 mg).
MS: [M+H]$^+$ 380.1.

B) 4-(2-Amino-9-(4-fluorobenzyl)-6-oxo-6,9-dihydro-1H-purin-8-yl)-N-(21-chloro-3,6,9,12,15-pentaoxahenicos-1-yl)benzamide To a mixture of 4-(2-amino-9-(4-fluorobenzyl)-6-oxo-6,9-dihydro-1H-purin-8-yl)benzoic acid (39 mg), 21-chloro-3,6,9,12,15-pentaoxahenicosan-1-amine (53 mg), DIPEA (105 uL), and DMA (1 mL), HATU (76 mg) was added at room temperature. The mixture was stirred at room temperature for 2 hours. The reaction mixture was purified by HPLC (YMC Triart C18, mobile phase: water/acetonitrile (10 mM ammonium bicarbonate system)) and HPLC (YMC Triart C18, mobile phase: water/acetonitrile (system containing 0.1% TFA)) to obtain the title compound (11.1 mg).
$^1$H NMR (300 MHz, CD$_3$OD) δ 1.39 (4H, brs), 1.49-1.62 (2H, m), 1.67-1.82 (2H, m), 2.82 (1H, s), 3.06 (1H, s), 3.43 (2H, t, J=6.3 Hz), 3.51-3.67 (21H, m), 5.40 (2H, s), 6.96-7.04 (2H, m), 7.04-7.13 (2H, m), 7.68 (2H, d, J=8.6 Hz), 7.92 (2H, d, J=8.3 Hz).

Example 5

(2E)-3-(2-Amino-9-(4-fluorobenzyl)-6-oxo-6,9-dihydro-1H-purin-8-yl)-N-(21-chloro-3,6,9,12,15-pentaoxahenicos-1-yl)acrylamide A) (2E)-3-(2-Amino-9-(4-fluorobenzyl)-6-oxo-6,9-dihydro-1H-purin-8-yl)acrylic Acid A mixture of 2-amino-8-bromo-9-(4-fluorobenzyl)-1,9-dihydro-6H-purin-6-one (300 mg), potassium carbonate (184 mg), ethyl (2E)-3-(4,4,5,5-tetramethyl-1,3,2-dioxaborolan-2-yl)acrylate (241 mg), triphenylphosphine-3,3',3"-trisulfonic acid trisodium salt hydrate (52.0 mg), palladium (II) acetate (10 mg), acetonitrile (2 mL), and water (1 mL) was stirred overnight at 100° C. The mixture was brought back to room temperature, and the solution was rendered basic by the addition of a 2 M aqueous sodium hydroxide solution and washed with ethyl acetate. The pH of the aqueous layer was adjusted to 4 to 5 with 1 M hydrochloric acid. The resulting precipitate was filtered off. The obtained filtrate was subjected to extraction with ethyl acetate-isopropanol. The organic layer was separated, washed with saturated saline, then dried over anhydrous magnesium sulfate, and concentrated under reduced pressure. The obtained residue was washed with a small amount of ethyl acetate-THF and collected by filtration to obtain the title compound (117 mg).
MS: [M+H]$^+$ 330.1.

B) (2E)-3-(2-Amino-9-(4-fluorobenzyl)-6-oxo-6,9-dihydro-1H-purin-8-yl)-N-(21-chloro-3,6,9,12,15-pentaoxahenicos-1-yl)acrylamide To a mixture of (2E)-3-(2-amino-9-(4-fluorobenzyl)-6-oxo-6,9-dihydro-1H-purin-8-yl)acrylic acid (33 mg), 21-chloro-3,6,9,12,15-pentaoxahenicosan-1-amine (53 mg), DIPEA (105 uL), and DMA (1 mL), HATU (76 mg) was added at room temperature. The mixture was stirred at room temperature for 2 hours. The reaction mixture was purified by HPLC (YMC Triart C18, mobile phase: water/acetonitrile (10 mM ammonium bicarbonate system)) and HPLC (YMC Triart C18, mobile phase: water/acetonitrile (system containing 0.1% TFA)) to obtain the title compound (8.2 mg).
$^1$H NMR (300 MHz, CD$_3$OD) δ 1.28-1.49 (4H, m), 1.49-1.61 (2H, m), 1.74 (2H, quin, J=6.9 Hz), 3.40-3.71 (24H, m), 5.38 (2H, s), 6.98 (1H, d, J=15.2 Hz), 7.02-7.11 (2H, m), 7.29 (2H, dd, J=8.1, 5.5 Hz), 7.44 (1H, d, J=15.1 Hz).

Example 6

3-(2-Amino-9-(4-fluorobenzyl)-6-oxo-6,9-dihydro-1H-purin-8-yl)-N-(21-chloro-3,6,9,12,15-pentaoxahenicos-1-yl)propanamide A) 3-(2-Amino-9-(4-fluorobenzyl)-6-oxo-6,9-dihydro-1H-purin-8-yl)propanoic Acid A mixture of (2E)-3-(2-amino-9-(4-fluorobenzyl)-6-oxo-6,9-dihydro-1H-purin-8-yl)acrylic acid (114 mg), 10% palladium carbon (18 mg), and DMF (2 mL) was stirred at 50° C. for 4 hours in a hydrogen atmosphere of normal pressure. The catalyst was filtered off, and the filtrate was diluted with ethyl acetate-IPE. The mixture was stirred overnight at room temperature. The resulting solid was collected by filtration, washed with ethyl acetate-IPE, and dried under reduced pressure to obtain the title compound (41 mg).
MS: [M+H]$^+$ 332.2.

B) 3-(2-Amino-9-(4-fluorobenzyl)-6-oxo-6,9-dihydro-1H-purin-8-yl)-N-(21-chloro-3,6,9,12,15-pentaoxahenicos-1-yl)propanamide To a mixture of 3-(2-amino-9-(4-fluorobenzyl)-6-oxo-6,9-dihydro-1H-purin-8-yl)propanoic acid (33 mg), 21-chloro-3,6,9,12,15-pentaoxahenicosan-1-amine (53 mg), DIPEA (105 uL), and DMA (1 mL), HATU (76 mg) was added at room temperature. The mixture was stirred at room temperature for 2 hours. The reaction mixture was purified by HPLC (YMC Triart C18, mobile phase: water/acetonitrile (10 mM ammonium bicarbonate system)) and HPLC (YMC Triart C18, mobile phase: water/acetonitrile (system containing 0.1% TFA)) to obtain the title compound (18.6 mg).
$^1$H NMR (300 MHz, CD$_3$OD) δ 1.31-1.48 (4H, m), 1.56 (2H, quin, J=6.7 Hz), 1.74 (2H, quin, J=6.9 Hz), 2.69 (2H, t, J=7.1 Hz), 3.00 (1H, brs), 3.14 (2H, t, J=7.0 Hz), 3.41-3.64 (24H, m), 5.42 (2H, s), 7.10 (2H, t, J=8.6 Hz), 7.38 (2H, dd, J=8.2, 5.5 Hz).

Example 8

$N^3$-(2-Amino-9-(4-fluorobenzyl)-6-oxo-6,9-dihydro-1H-purin-8-yl)-N-(21-chloro-3,6,9,12,15-pentaoxa-henicos-1-yl)-β-alaninamide A) N-(2-amino-9-(4-fluorobenzyl)-6-oxo-6,9-di-hydro-1H-purin-8-yl)-β-alanine A mixture of 2-amino-8-bromo-9-(4-fluorobenzyl)-1,9-dihydro-6H-purin-6-one (300 mg), β-alanine (158 mg), potassium carbonate (540 mg), DMSO (3 mL) and water (3 mL) was stirred at 140° C. for 14 hours in a nitrogen atmosphere. Then, β-alanine (790 mg) and potassium carbonate (1.47 g) were added to the mixture, and the mixture was stirred at 140° C. for 8 hours in a nitrogen atmosphere. β-alanine (790 mg), potassium carbonate (1.47 g) and DMSO (3 mL) were added to the mixture, and the mixture was stirred at 160° C. for 14 hours in a nitrogen atmosphere. Then, DMSO (2 mL) and water (1 mL) were added to the mixture, and the mixture was stirred at 160° C. for 7 days in a nitrogen atmosphere. The reaction mixture was filtered. Insoluble matter was filtered off, and the filtrate was concentrated. The residue was diluted with MeOH. Then, insoluble matter was filtered off, and the filtrate was concentrated. The residue was purified by HPLC (L-Column 2 ODS, mobile phase: water/acetonitrile (system containing 0.1% TFA)). The obtained crystals were washed with ethyl acetate and then collected by filtration to obtain the title compound (67.0 mg).

MS: [M+H]$^+$ 347.1.

B) tert-Butyl (21-chloro-3,6,9,12,15-pentaoxahen-icos-1-yl)carbamate

To a solution of 21-chloro-3,6,9,12,15-pentaoxahenic-osan-1-amine (5.90 g) in THF (60 mL), Boc$_2$O (4.00 mL) was added dropwise under ice cooling, and the mixture was warmed to room temperature in a nitrogen atmosphere. The mixture was stirred at room temperature for 2 hours in a nitrogen atmosphere. Then, DIPEA (3.47 mL) was added dropwise to the mixture, and the mixture was stirred at room temperature for 2 hours in a nitrogen atmosphere. The mixture was concentrated under reduced pressure, and the residue was diluted with toluene. Insoluble matter was filtered off. The filtrate was concentrated under reduced pressure, and the residue was purified by silica gel column chromatography (ethyl acetate/hexane) to obtain the title compound (2.10 g).

MS: [M+Na]$^+$ 478.2.

C) 21-Chloro-3,6,9,12,15-pentaoxahenicosan-1-amine Hydrochloride

2 M hydrochloric acid in methanol (20 mL) was added to tert-butyl (21-chloro-3,6,9,12,15-pentaoxahenicos-1-yl)carbamate (2.10 g) under ice cooling, and the mixture was warmed to room temperature in a nitrogen atmosphere. The mixture was stirred at room temperature for 18 hours in a nitrogen atmosphere and then concentrated under reduced pressure to obtain the title compound (1.78 g).

$^1$H NMR (300 MHz, CDCl$_3$) δ 1.22-1.69 (6H, m), 1.78 (2H, quin, J=6.9 Hz), 2.36 (2H, brs), 3.14 (2H, brs), 3.44-3.85 (18H, m), 3.94 (2H, brs), 8.09 (3H, brs).

D) $N^3$-(2-Amino-9-(4-fluorobenzyl)-6-oxo-6,9-dihydro-1H-purin-8-yl)-N-(21-chloro-3,6,9,12,15-pentaoxahenicos-1-yl)-β-alaninamide To a mixture of N-(2-amino-9-(4-fluorobenzyl)-6-oxo-6,9-dihydro-1H-purin-8-yl)-β-alanine (20 mg), 21-chloro-3,6,9,12,15-pentaoxahenicosan-1-amine hydrochloride (27.2 mg), HOBt·H$_2$O (11.5 mg) and DMF (0.5 mL), WSC·HCl (14.4 mg) and DIPEA (0.030 mL) were added at room temperature, and the mixture was stirred at room temperature for 18 hours in a nitrogen atmosphere. The mixture was purified by silica gel column chromatography (MeOH/ethyl acetate) and then purified by HPLC (L-Column 2 ODS, mobile phase: water/acetonitrile (system containing 0.1% TFA)) to obtain the title compound (23.8 mg).

$^1$H NMR (300 MHz, DMSO-d$_6$) δ 1.17-1.58 (6H, m), 1.59-1.80 (2H, m), 2.41 (2H, brs), 3.45 (26H, d, J=6.0 Hz), 5.12 (2H, s), 6.90 (2H, brs), 7.11-7.24 (2H, m), 7.24-7.37 (2H, m), 8.00 (1H, brs), 8.68 (1H, brs), 11.19 (1H, brs).

Example 10

2-Amino-8-(3-((21-chloro-3,6,9,12,15-pentaoxahen-icos-1-yeoxy)phenyl)-9-(4-fluorobenzyl)-1,9-dihydro-6H-purin-6-one A) 2-(3-((21-Chloro-3,6,9,12,15-pentaoxahenicos-1-yeoxy)phenyl)-4,4,5,5-tetramethyl-1,3,2-dioxaboro-lane To a mixture of 21-chloro-3,6,9,12,15-pentaoxahenic-osan-1-ol (100 mg), 3-(4,4,5,5-tetramethyl-1,3,2-dioxaboro-lan-2-yl)phenol (61.7 mg), and anhydrous THF (3 mL), PPh$_3$ (103 mg) and a solution of 40% DEAD in toluene (0.191 mL) were added at room temperature. After stirring overnight at room temperature, the reaction solution was concentrated. The obtained residue was purified by silica gel column chromatography (ethyl acetate/hexane) to obtain the title compound (87.5 mg).

MS: [M+H]$^+$ 559.3.

B) 2-Amino-8-(3-((21-chloro-3,6,9,12,15-pentaoxa-henicos-1-yeoxy)phenyl)-9-(4-fluorobenzyl)-1,9-dihydro-6H-purin-6-one To a mixture of 2-(3-((21-chloro-3,6,9,12,15-pentaoxa-henicos-1-yeoxy)phenyl)-4,4,5,5-tetramethyl-1,3,2-dioxa-borolane (85 mg), acetonitrile (0.6 mL), and water (0.300 mL), 2-amino-8-bromo-9-(4-fluorobenzyl)-1,9-dihydro-6H-purin-6-one (36.7 mg), palladium(II) acetate (2.44 mg), potassium carbonate (22.52 mg), and triphenylphosphine-3,3',3''-trisulfonic acid trisodium salt hydrate (6.37 mg) were added at room temperature. The mixture was stirred overnight at 100° C. in a nitrogen atmosphere. Water was added to the mixture at room temperature, followed by extraction with ethyl acetate. The organic layer was separated, washed with saturated saline, then dried over anhydrous sodium sulfate, and concentrated under reduced pressure. The residue was purified by silica gel column chromatography (ethyl acetate/methanol), and the residue was purified by HPLC (L-Column 2 ODS, mobile phase: water/acetonitrile (system containing 0.1% TFA)). The obtained fraction was passed through MP-Carbonate resin and concentrated under reduced pressure to obtain the title compound (2.8 mg).

¹H NMR (300 MHz, CD₃OD) δ 1.28-1.49 (4H, m), 1.55 (2H, quin, J=6.7 Hz), 1.74 (2H, quin, J=6.9 Hz), 3.44 (2H, t, J=6.4 Hz), 3.49-3.72 (18H, m), 3.80 (2H, t, J=4.4 Hz), 4.04 (2H, t, J=4.5 Hz), 5.33 (2H, s), 6.96-7.16 (7H, m), 7.28-7.39 (1H, m).

Example 12

N²-Acetyl-S-(2-amino-9-cyclopentyl-6-oxo-6,9-dihydro-1H-purin-8-yl)-N-(21-chloro-3,6,9,12,15-pentaoxahenicos-1-yl)-L-cysteinamide A) 6-Chloro-N⁴-cyclopentylpyrimidine-2,4,5-triamine To a solution of cyclopentanamine (1.14 g) in butan-1-ol (20.0 mL), 4,6-dichloropyrimidine-2,5-diamine (2.00 g) and DIPEA (4.87 mL) were added, and the mixture was heated to reflux for 18 hours in a nitrogen atmosphere. The reaction solution was concentrated under reduced pressure. Then, a saturated aqueous solution of sodium bicarbonate and water were added to the residue, and the mixture was subjected to extraction with ethyl acetate. The organic layer was washed with water and saturated saline, then dried over anhydrous sodium sulfate, and concentrated under reduced pressure. The residue was purified by silica gel column chromatography (ethyl acetate/hexane) to obtain the title compound (2.30 g).
MS: [M+H]⁺ 228.1.

B) 6-Chloro-9-cyclopentyl-9H-purin-2-amine

To a suspension of 6-chloro-N⁴-cyclopentylpyrimidine-2,4,5-triamine (1.00 g) in triethyl orthoformate (10.0 mL), concentrated hydrochloric acid (0.2 mL) was added at room temperature. The reaction solution was stirred at room temperature for 2 hours. Then, triethyl orthoformate (5.0 mL) and concentrated hydrochloric acid (0.1 mL) were added in this order, and the reaction mixture was stirred at room temperature for 2 hours. The reaction solution was concentrated under reduced pressure. Then, THF (10.0 mL) and 0.5 N hydrochloric acid (10.0 mL) were added to the residue, and the mixture was stirred at room temperature for 4 hours. The mixture was neutralized with a saturated aqueous solution of sodium bicarbonate, followed by extraction with ethyl acetate. The organic layer was washed with water and saturated saline, then dried over anhydrous sodium sulfate, and concentrated under reduced pressure. The obtained residue was crystallized from ethyl acetate/IPE to obtain the title compound (610 mg).
MS: [M+H]⁺ 238.1.

C) 2-Amino-9-cyclopentyl-1,9-dihydro-6H-purin-6-one

To a solution of 6-chloro-9-cyclopentyl-9H-purin-2-amine (610 mg) in TFA (6.0 mL), water (2 mL) was added under ice cooling, and the mixture was warmed to 50° C. in a nitrogen atmosphere. The reaction mixture was stirred at 50° C. for 14 hours in a nitrogen atmosphere and then concentrated under reduced pressure. Water (6 mL) was added to the residue, and the pH of the mixture was adjusted to 7 with an 8 N sodium hydroxide solution. The resulting crystals were collected by filtration and washed with ethyl acetate to obtain the title compound (530 mg).
MS: [M+H]⁺ 220.2.

D) 2-Amino-8-bromo-9-cyclopentyl-1,9-dihydro-6H-purin-6-one

To a mixture of 2-amino-9-cyclopentyl-1,9-dihydro-6H-purin-6-one (480 mg), acetonitrile (20 mL) and water (5 mL), NBS (585 mg) was added under ice cooling, and the mixture was warmed to room temperature. The mixture was stirred at room temperature for 1 hour. Then, acetone (5 mL) was added to the mixture under ice cooling. The mixture was stirred for 1 hour under ice cooling. Then, the crystals were collected by filtration and dissolved in a mixed solution of THF and MeOH. Insoluble matter was filtered off, and the filtrate was concentrated under reduced pressure. The obtained crystals were washed with MeOH and then collected by filtration to obtain the title compound (410 mg).
¹H NMR (300 MHz, DMSO-d₆) δ 1.51-2.33 (8H, m), 4.73 (1H, quin, J=8.6 Hz), 6.46 (2H, brs), 10.66 (1H, s).

E) N-Acetyl-S-(2-amino-9-cyclopentyl-6-oxo-6,9-dihydro-1H-purin-8-yl)-L-cysteine To a mixture of 2-amino-8-bromo-9-cyclopentyl-1,9-dihydro-6H-purin-6-one (50.0 mg), N-acetyl-L-cysteine (82.0 mg) and DMSO (1 mL), potassium carbonate (153 mg) was added at room temperature, and the mixture was stirred at 80° C. for 2 hours in a nitrogen atmosphere. MeOH was added to the mixture. Insoluble matter was filtered off, and the filtrate was concentrated under reduced pressure. The residue was purified by HPLC (L-Column 2 ODS, mobile phase: water/acetonitrile (system containing 0.1% TFA)). The obtained crystals were washed with ethyl acetate and then collected by filtration to obtain the title compound (40.0 mg).
MS: [M+H]⁺ 381.2.

F) N²-Acetyl-S-(2-amino-9-cyclopentyl-6-oxo-6,9-dihydro-1H-purin-8-yl)-N-(21-chloro-3,6,9,12,15-pentaoxahenicos-1-yl)-L-cysteinamide To a mixture of N-acetyl-S-(2-amino-9-cyclopentyl-6-oxo-6,9-dihydro-1H-purin-8-yl)-L-cysteine (30.0 mg), 21-chloro-3,6,9,12,15-pentaoxahenicosan-1-amine (56.1 mg) and DMA (0.1 mL), a solution of DIPEA (20.4 mg) in DMA (0.1 mL) and HATU (60.0 mg) were added at room temperature, and the mixture was stirred at room temperature for 6 hours in a nitrogen atmosphere. Water was added to the mixture. Then, the mixture was concentrated under reduced pressure. The residue was purified by HPLC (L-Column 2 ODS, mobile phase: water/acetonitrile (system containing 0.1% TFA)) to obtain the title compound (32.0 mg).
¹H NMR (300 MHz, DMSO-d₆) δ 1.11-2.30 (19H, m), 3.01-3.78 (26H, m), 4.40-4.75 (2H, m), 6.39 (2H, brs), 8.02-8.18 (1H, m), 8.45 (1H, d, J=7.7 Hz), 10.58 (1H, s).

Example 13

N²-Acetyl-N-(21-chloro-3,6,9,12,15-pentaoxahenicos-1-yl)-S-(9-(4-fluorobenzyl)-1,3-dimethyl-2,6-dioxo-2,3,6,9-tetrahydro-1H-purin-8-yl)-L-cysteinamide A) 9-(4-Fluorobenzyl)-1,3-dimethyl-3,9-dihydro-1H-purine-2,6-dione To a mixture of 1,3-dimethyl-3,9-dihydro-1H-purine-2,6-dione (3 g), potassium carbonate (3.45 g), and anhydrous DMF (30 mL), 1-(bromomethyl)-4-fluorobenzene (3.78 g) was added at room temperature. The mixture was stirred overnight at room temperature. Water was added thereto, and the resulting precipitate was collected by filtration and washed with water to obtain the title compound (4.73 g).
MS: [M+H]$^+$ 289.2.

B) 8-Bromo-9-(4-fluorobenzyl)-1,3-dimethyl-3,9-dihydro-1H-purine-2,6-dione

To a mixture of 9-(4-fluorobenzyl)-1,3-dimethyl-3,9-dihydro-1H-purine-2,6-dione (289 mg) and anhydrous DMF (5 mL), NBS (214 mg) was added at room temperature. The mixture was stirred at 50° C. for 2 hours. Then, water was added thereto, and the mixture was stirred at room temperature for 1 hour. The precipitate was collected by filtration and washed with water to obtain the title compound (166 mg).
MS: [M+H]$^+$ 367.1.

C) N-Acetyl-S-(9-(4-fluorobenzyl)-1,3-dimethyl-2,6-dioxo-2,3,6,9-tetrahydro-1H-purin-8-yl)-L-cysteine To a mixture of 8-bromo-9-(4-fluorobenzyl)-1,3-dimethyl-3,9-dihydro-1H-purine-2,6-dione (167 mg), potassium carbonate (377 mg), and DMSO (1.5 mL), N-acetyl-L-cysteine (186 mg) was added at room temperature. The mixture was stirred overnight at 80° C. After cooling to room temperature, water was added thereto, and the mixture was rendered acidic with 1 M hydrochloric acid and stirred at room temperature for 1 hour. The precipitate was collected by filtration and washed with water to obtain the title compound (104 mg).
MS: [M+H]$^+$ 450.2.

D) N$^2$-Acetyl-N-(21-chloro-3,6,9,12,15-pentaoxahenicos-1-yl)-S-(9-(4-fluorobenzyl)-1,3-dimethyl-2,6-dioxo-2,3,6,9-tetrahydro-1H-purin-8-yl)-L-cysteinamide To a mixture of N-acetyl-S-(9-(4-fluorobenzyl)-1,3-dimethyl-2,6-dioxo-2,3,6,9-tetrahydro-1H-purin-8-yl)-L-cysteine (104 mg), HATU (106 mg), 21-chloro-3,6,9,12,15-pentaoxahenicosan-1-amine (99 mg), and anhydrous DMF (1 mL), DIPEA (0.061 mL) was added at room temperature. The mixture was stirred overnight at room temperature. Water was added to the mixture, followed by extraction with ethyl acetate. The organic layer was separated, washed with saturated saline, then dried over anhydrous magnesium sulfate, and concentrated under reduced pressure. The residue was purified by HPLC (YMC-Actus Triart Prep C8-S, mobile phase: water/acetonitrile (system containing 0.1% TFA)) to obtain the title compound (35.8 mg).
$^1$H NMR (300 MHz, CDCl$_3$) δ 1.21-1.86 (8H, m), 1.98 (3H, s), 3.32-3.74 (33H, m), 4.80 (1H, q, J=6.2 Hz), 5.34-5.60 (2H, m), 6.94-7.09 (2H, m), 7.30-7.53 (3H, m).

Example 15

2-Amino-8-(1-(21-chloro-3,6,9,12,15-pentaoxahenicos-1-yl)-1H-1,2,3-triazol-4-yl)-9-(4-fluorobenzyl)-1,9-dihydro-6H-purin-6-one

A) 2-Amino-9-(4-fluorobenzyl)-8-((trimethylsilyl)ethynyl)-1,9-dihydro-6H-purin-6-one To a mixture of 2-amino-8-bromo-9-(4-fluorobenzyl)-1,9-dihydro-6H-purin-6-one (60 mg) and anhydrous DMF (2 mL), ethynyl(trimethyl)silane (52.3 mg), dichloro(bistriphenylphosphine)palladium(II) (6.23 mg), TEA (71.8 mg), and copper(I) iodide (3.38 mg) were added at room temperature. The mixture was stirred overnight at 70° C. in a nitrogen atmosphere. Water was added to the mixture at room temperature, followed by extraction with ethyl acetate. The organic layer was separated, washed with water and saturated saline, then dried over anhydrous sodium sulfate, and concentrated under reduced pressure. The residue was purified by silica gel column chromatography (ethyl acetate/methanol) to obtain the title compound (18 mg).
MS: [M+H]$^+$ 356.1.

B) 2-Amino-8-ethynyl-9-(4-fluorobenzyl)-1,9-dihydro-6H-purin-6-one

A mixture of 2-amino-9-(4-fluorobenzyl)-8-((trimethylsilyl)ethynyl)-1,9-dihydro-6H-purin-6-one (16.4 mg) and MeOH (2 mL) was suspended in a hot water bath, and potassium carbonate (33 mg) was added thereto at the same temperature as above. After stirring at the same temperature as above for 10 minutes, the reaction solution was filtered. The obtained residue was concentrated under reduced pressure to obtain a partially purified product of the title compound (51 mg).
MS: [M+H]$^+$ 284.1.

C) 21-Chloro-3,6,9,12,15-pentaoxahenicosan-1-ol

To a mixture of 3,6,9,12-tetraoxatetradecane-1,14-diol (2 g) and anhydrous THF (40 mL), potassium tert-butoxide (1.036 g) was added at room temperature. The reaction mixture was stirred at 60° C. for 30 minutes. Then, 1-chloro-6-iodohexane (2.069 g) was added thereto. After stirring at 60° C. for 2 hours, the reaction solution was filtered through celite. The residue was purified by silica gel column chromatography (ethyl acetate/methanol) to obtain the title compound (910 mg).
MS: [M+H]$^+$ 357.2.

D) 1-Azido-21-chloro-3,6,9,12,15-pentaoxahenicosane

To a mixture of 21-chloro-3,6,9,12,15-pentaoxahenicosan-1-ol (100 mg), PPh$_3$ (110 mg), a solution of 40% DEAD in toluene (0.191 mL), and anhydrous THF (3 mL), DPPA (0.072 mL) was added at 0° C. After stirring overnight at room temperature, the reaction solution was concentrated. The obtained residue was purified by silica gel column chromatography (ethyl acetate/hexane) to obtain the title compound (40 mg).
$^1$H NMR (300 MHz, CD$_3$OD) δ 1.31-1.52 (4H, m), 1.59 (2H, quin, J=6.7 Hz), 1.78 (2H, dq, J=13.3, 6.6 Hz), 3.24 (1H, t, J=6.9 Hz), 3.37 (2H, t, J=4.8 Hz), 3.48 (2H, t, J=6.5 Hz), 3.51-3.70 (19H, m).

E) 2-Amino-8-(1-(21-chloro-3,6,9,12,15-pentaoxahenicos-1-yl)-1H-1,2,3-triazol-4-yl)-9-(4-fluorobenzyl)-1,9-dihydro-6H-purin-6-one To a mixture of 1-azido-21-chloro-3,6,9,12,15-pentaoxahenicosane (40 mg), tert-butanol (0.5 mL), and water (0.500 mL), 2-amino-8-ethynyl-9-(4-fluorobenzyl)-1,9-dihydro-6H-purin-6-one (14.16 mg), copper(II) sulfate (3.99 mg), and L-ascorbic acid (44.0 mg) were added at room temperature. After stirring overnight at room temperature, the reaction solution was filtered through celite. The residue was purified by silica gel column chromatography (ethyl acetate/ methanol). Then, the obtained fraction was purified by HPLC (L-Column 2 ODS, mobile phase: water/acetonitrile (10 mM ammonium bicarbonate system)). The obtained fraction was concentrated under reduced pressure to obtain the title compound (2.0 mg).

$^1$H NMR (300 MHz, CD$_3$OD) δ 1.25-1.47 (4H, m), 1.54 (2H, quin, J=6.7 Hz), 1.73 (2H, quin, J=7.2 Hz), 3.42 (2H, t, J=6.5 Hz), 3.47-3.66 (18H, m), 3.91 (2H, t, J=4.8 Hz), 4.64 (2H, t, J=4.7 Hz), 5.81 (2H, s), 6.96 (2H, t, J=8.8 Hz), 7.26-7.37 (2H, m), 8.44 (1H, s).

Example 16

2-Amino-8-(25-chloro-4,7,10,13,16,19-hexaoxapentacos-1-yn-1-yl)-9-(4-fluorobenzyl)-1,9-dihydro-6H-purin-6-one A)
25-Chloro-4,7,10,13,16,19-hexaoxapentacos-1-yne To a mixture of prop-2-yn-1-yl 4-methylbenzenesulfonate (153 mg), 21-chloro-3,6,9,12,15-pentaoxahenicosan-1-ol (200 mg), and anhydrous THF (5 mL), 60% sodium hydride (56.0 mg) was added at 0° C. The mixture was stirred overnight at room temperature. Water was added to the mixture at room temperature, followed by extraction with ethyl acetate. The organic layer was separated, washed with saturated saline, then dried over anhydrous sodium sulfate, and concentrated under reduced pressure. The residue was purified by silica gel column chromatography (ethyl acetate/hexane) to obtain the title compound (168 mg).

MS: [M+H]$^+$ 395.2.

B) 2-Amino-8-(25-chloro-4,7,10,13,16,19-hexaoxapentacos-1-yn-1-yl)-9-(4-fluorobenzyl)-1,9-dihydro-6H-purin-6-one To a mixture of 2-amino-8-bromo-9-(4-fluorobenzyl)-1,9-dihydro-6H-purin-6-one (94 mg) and anhydrous DMF (4 mL), 25-chloro-4,7,10,13,16,19-hexaoxapentacos-1-yne (165 mg), dichloro(bistriphenylphosphine)palladium(II) (9.77 mg), TEA (113 mg), and copper(I) iodide (5.30 mg) were added at room temperature. The mixture was stirred overnight at 70° C. in a nitrogen atmosphere. Water was added to the mixture at room temperature, followed by extraction with ethyl acetate. The organic layer was separated, washed with water and saturated saline, then dried over anhydrous sodium sulfate, and concentrated under reduced pressure. The residue was purified by silica gel column chromatography (ethyl acetate/methanol). Then, the obtained fraction was purified by HPLC (L-Column 2 ODS, mobile phase: water/acetonitrile (10 mM ammonium bicarbonate system)). The obtained fraction was concentrated under reduced pressure to obtain the title compound (26.3 mg).

$^1$H NMR (300 MHz, CD$_3$OD) δ 1.25-1.50 (4H, m), 1.56 (2H, quin, J=6.6 Hz), 1.74 (2H, quin, J=6.9 Hz), 3.45 (2H, t, J=6.5 Hz), 3.50-3.70 (22H, m), 4.49 (2H, s), 5.29 (2H, s), 7.07 (2H, t, J=8.6 Hz), 7.39 (2H, dd, J=8.0, 5.5 Hz).

Example 17

N$^2$-Acetyl-S-(6-amino-9-(4-fluorobenzyl)-9H-purin-8-yl)-N-(21-chloro-3,6,9,12,15-pentaoxahenicos-1-yl)-L-cysteinamide trifluoroacetate A) 8-Bromo-9-(4-fluorobenzyl)-9H-purin-6-amine To a mixture of 8-bromo-9H-purin-6-amine (1.5 g) and anhydrous DMF (50 mL), 60% sodium hydride (0.308 g) was added at 70° C. The reaction mixture was stirred at 70° C. for 30 minutes. Then, 1-(bromomethyl)-4-fluorobenzene (1.457 g) was added thereto. The mixture was stirred overnight at the same temperature as above. After cooling to room temperature, water was added thereto, and the mixture was stirred at room temperature for 1 hour. The resulting precipitate was collected by filtration and washed with water to obtain the title compound (659 mg).

$^1$H NMR (300 MHz, DMSO-d$_6$) δ 5.34 (2H, s), 7.12-7.25 (2H, m), 7.26-7.36 (2H, m), 7.45 (2H, brs), 8.17 (1H, s).

B) N-Acetyl-S-(6-amino-9-(4-fluorobenzyl)-9H-purin-8-yl)-L-cysteine

To a mixture of 8-bromo-9-(4-fluorobenzyl)-9H-purin-6-amine (300 mg), potassium carbonate (772 mg), and DMSO (3 mL), N-acetyl-L-cysteine (380 mg) was added at room temperature. The mixture was stirred overnight at 80° C. Water was added to the reaction mixture, and the mixture was rendered acidic with 2 M hydrochloric acid. The resulting precipitate was collected by filtration and washed with water to obtain the title compound (296 mg).

MS: [M+H]$^+$ 405.1.

C) N$^2$-Acetyl-S-(6-amino-9-(4-fluorobenzyl)-9H-purin-8-yl)-N-(21-chloro-3,6,9,12,15-pentaoxahenicos-1-yl)-L-cysteinamide trifluoroacetate To a mixture of N-acetyl-S-(6-amino-9-(4-fluorobenzyl)-9H-purin-8-yl)-L-cysteine (291 mg), HATU (328 mg), 21-chloro-3,6,9,12,15-pentaoxahenicosan-1-amine (307 mg) and anhydrous DMF (1 mL), DIPEA (0.189 mL) was added at room temperature. The mixture was stirred overnight at room temperature. Water was added to the mixture, followed by extraction with ethyl acetate. The organic layer was separated, washed with saturated saline, then dried over anhydrous magnesium sulfate, and concentrated under reduced pressure. The residue was purified by HPLC (YMC-Actus Triart Prep C8-S, mobile phase: water/acetonitrile (system containing 0.1% TFA)) to obtain the title compound (6.0 mg).

$^1$H NMR (300 MHz, CD$_3$OD) δ 1.09-1.64 (8H, m), 1.67-1.80 (2H, m), 1.95 (3H, s), 3.33-3.73 (24H, m), 3.93 (1H, dd, J=13.9, 4.9 Hz), 5.24-5.51 (2H, m), 7.01-7.15 (2H, m), 7.29-7.42 (2H, m), 8.13 (1H, brs), 8.34 (1H, s).

Example 18

N$^2$-Acetyl-N-(21-chloro-3,6,9,12,15-pentaoxahenicos-1-yl)-S-(9-(4-fluorobenzyl)-9H-purin-8-yl)-L-cysteinamide A) 8-Bromo-9-(4-fluorobenzyl)-9H-purine A mixture of 8-bromo-9-(4-fluorobenzyl)-9H-purin-6-amine (239 mg), amyl nitrite (521 mg), and anhydrous THF (3 mL) was irradiated with microwave at 120° C. for 30 minutes. The reaction mixture was concentrated under reduced pressure, and toluene was added to the residue. Insoluble matter was removed by filtration, and the filtrate was concentrated under reduced pressure. The residue was purified by silica gel column chromatography (NH, ethyl acetate/hexane) to obtain the title compound (69.5 mg).

MS: [M+H]$^+$ 307.1.

B) N-Acetyl-S-(9-(4-fluorobenzyl)-9H-purin-8-yl)-L-cysteine

To a mixture of 8-bromo-9-(4-fluorobenzyl)-9H-purine (59.8 mg), potassium carbonate (161 mg) and DMSO (1 mL), N-acetyl-L-cysteine (79 mg) was added at room temperature. The mixture was stirred overnight at 80° C. After cooling to room temperature, water was added thereto, and the mixture was rendered acidic with 2 M hydrochloric acid and stirred at room temperature for 1 hour. The precipitate was collected by filtration and washed with water to obtain the title compound (28.5 mg).

MS: [M+H]$^+$ 390.1.

C) $N^2$-Acetyl-N-(21-chloro-3,6,9,12,15-pentaoxahenicos-1-yl)-S-(9-(4-fluorobenzyl)-9H-purin-8-yl)-L-cysteinamide To a mixture of N-acetyl-S-(9-(4-fluorobenzyl)-9H-purin-8-yl)-L-cysteine (28.5 mg), HATU (33.4 mg), 21-chloro-3,6,9,12,15-pentaoxahenicosan-1-amine (31.3 mg) and anhydrous DMF (1 mL), DIPEA (0.019 mL) was added at room temperature. The mixture was stirred overnight at room temperature. Water was added to the mixture, followed by extraction with ethyl acetate. The organic layer was separated, washed with saturated saline, then dried over anhydrous magnesium sulfate, and concentrated under reduced pressure. The residue was purified by HPLC (YMC-Actus Triart Prep C8-S, mobile phase: water/acetonitrile (system containing 0.1% TFA)) to obtain the title compound (10.0 mg).

$^1$H NMR (300 MHz, CD$_3$OD) δ 1.19-1.63 (8H, m), 1.68-1.82 (2H, m), 1.95 (3H, s), 3.34-3.41 (2H, m), 3.45 (2H, t, J=6.4 Hz), 3.50-3.69 (20H, m), 3.97 (1H, dd, J=13.9, 4.9 Hz), 5.48 (2H, s), 7.01-7.16 (2H, m), 7.35-7.47 (2H, m), 9.06 (1H, s), 9.13 (1H, s).

Example 19

$N^2$-Acetyl-S-(2-amino-4-((4-fluorobenzyl)amino)-6-oxo-1,6-dihydropyrimidin-5-yl)-N-(21-chloro-3,6,9,12,15-pentaoxahenicos-1-yl)-L-cysteinamide Trifluoroacetate A) 2-Amino-6-((4-fluorobenzyl)amino)pyrimidin-4(3H)-one To a mixture of 2-amino-6-chloropyrimidin-4(3H)-one (3 g), water (50 mL) and ethanol (10 mL), 1-(4-fluorophenyl)methanamine (5.16 g) was added at room temperature. The mixture was stirred at 90° C. for 5 hours. After cooling to room temperature, the reaction mixture was rendered acidic with 2 M hydrochloric acid. Ethyl acetate was added thereto, and the mixture was stirred at room temperature for 1 hour. Insoluble matter was filtered, and the organic layer in the filtrate was washed with saturated saline. The organic layer was dried over anhydrous magnesium sulfate, filtered, and concentrated under reduced pressure. The residue was dissolved by the addition of ethyl acetate and stirred at room temperature for 1 hour. The deposited solid was collected and washed with a small amount of ethyl acetate to obtain the title compound (502 mg).

MS: [M+H]$^+$ 235.2.

B) 2-Amino-5-bromo-6-((4-fluorobenzyl)amino)pyrimidin-4(3H)-one

To a mixture of 2-amino-6-((4-fluorobenzyl)amino)pyrimidin-4(3H)-one (452 mg) and anhydrous DMF (10 mL), NBS (412 mg) was added at room temperature. The mixture was stirred at 50° C. for 2 hours. After cooling to room temperature, water was added thereto, and the mixture was stirred at room temperature for 1 hour. The precipitate was collected by filtration and washed with water to obtain the title compound (385 mg).

MS: [M+H]$^+$ 313.1.

C) N-Acetyl-S-(2-amino-4-((4-fluorobenzyl)amino)-6-oxo-1,6-dihydropyrimidin-5-yl)-L-cysteine To a mixture of 2-amino-5-bromo-6-((4-fluorobenzyl)amino)pyrimidin-4(3H)-one (385 mg), potassium carbonate (1020 mg) and DMSO (5 mL), N-acetyl-L-cysteine (502 mg) was added at room temperature. The mixture was stirred overnight at 80° C. Water was added to the reaction mixture, and insoluble matter was filtered through celite. The filtrate was rendered acidic with 2 M hydrochloric acid and stirred at room temperature for 1 hour, and the precipitate was removed by filtration. The filtrate was rendered basic with a saturated aqueous solution of sodium bicarbonate, washed with ethyl acetate, and then rendered acidic with 2 M hydrochloric acid, followed by extraction with ethyl acetate. The organic layer was dried over anhydrous magnesium sulfate, filtered, and concentrated under reduced pressure to obtain the title compound (201 mg).

MS: [M+H]$^+$ 396.2.

D) $N^2$-Acetyl-S-(2-amino-4-((4-fluorobenzyl)amino)-6-oxo-1,6-dihydropyrimidin-5-yl)-N-(21-chloro-3,6,9,12,15-pentaoxahenicos-1-yl)-L-cysteinamide Trifluoroacetate To a mixture of N-acetyl-S-(2-amino-4-((4-fluorobenzyl)amino)-6-oxo-1,6-dihydropyrimidin-5-yl)-L-cysteine (201 mg), HATU (232 mg), 21-chloro-3,6,9,12,15-pentaoxahenicosan-1-amine (217 mg) and anhydrous DMF (2 mL), DIPEA (0.133 mL) was added at room temperature. The mixture was stirred overnight at room temperature. Water was added to the mixture, followed by extraction with ethyl acetate. The organic layer was separated, washed with saturated saline, then dried over anhydrous magnesium sulfate, and concentrated under reduced pressure. The residue was purified by HPLC (YMC-Actus Triart Prep C8-S, mobile phase: water/acetonitrile (system containing 0.1% TFA)) to obtain the title compound (29.9 mg).

$^1$H NMR (300 MHz, CD$_3$OD) δ 1.17-1.64 (8H, m), 1.68-1.83 (2H, m), 2.01 (3H, s), 2.68 (1H, dd, J=13.6, 6.0 Hz), 2.99 (1H, dd, J=13.6, 6.4 Hz), 3.32-3.39 (2H, m), 3.40-3.70 (20H, m), 4.42 (1H, t, J=6.2 Hz), 4.63 (2H, s), 6.92-7.16 (2H, m), 7.22-7.54 (2H, m).

Example 20

$N^2$-Acetyl-S-(2-amino-9-benzyl-6-oxo-6,9-dihydro-1H-purin-8-yl)-N-(21-chloro-3,6,9,12,15-pentaoxahenicos-1-yl)-L-cysteinamide Trifluoroacetate A) 9-Benzyl-6-chloro-9H-purin-2-amine A mixture of 6-chloro-9H-purin-2-amine (1.50 g), (bromomethyl)benzene (2.27 g), potassium carbonate (3.67 g) and DMF (25 mL) was stirred at 25° C. for 12 hours. The reaction mixture was filtered, and saturated saline was added to the filtrate. After extraction with ethyl acetate, the obtained organic layer was dried over sodium sulfate, filtered, and concentrated under reduced pressure. The residue was purified by silica gel column chromatography (ethyl acetate/dichloromethane) to obtain the title compound (1.0 g).

$^1$H NMR (400 MHz, DMSO-$d_6$) δ 5.29 (2H, s), 6.94 (2H, s), 7.21-7.39 (5H, m), 8.23 (1H, s).

B) 2-Amino-9-benzyl-1,9-dihydro-6H-purin-6-one

A mixture of 9-benzyl-6-chloro-9H-purin-2-amine (800 mg), formic acid (16 mL) and water (4 mL) was stirred at 75° C. for 2 hours. The reaction mixture was concentrated under reduced pressure, and the residue was diluted with a saturated aqueous solution of sodium carbonate (20 mL). The precipitate was collected, washed with water (10 mL), and dried under reduced pressure to obtain the title compound (700 mg).

$^1$H NMR (400 MHz, DMSO-$d_6$) δ 5.18 (2H, s), 6.58 (2H, brs), 7.17-7.40 (5H, m), 7.75 (1H, s), 10.85 (1H, brs).

C) 2-Amino-9-benzyl-8-bromo-1,9-dihydro-6H-purin-6-one

A mixture of 2-amino-9-benzyl-1,9-dihydro-6H-purin-6-one (600 mg), acetic acid (10 mL) and NBS (576 mg) was stirred at 25° C. for 12 hours. The reaction mixture was diluted with ethyl acetate. The precipitate was collected and suspended in a mixture of a 10% aqueous sodium hydroxide solution (5 mL) and methanol (5 mL). The obtained precipitate was filtered and dried under reduced pressure to obtain the title compound (411 mg).

MS: [M+H]$^+$ 320.0.

D) N-Acetyl-S-(2-amino-9-benzyl-6-oxo-6,9-dihydro-1H-purin-8-yl)-L-cysteine

To a mixture of 2-amino-9-benzyl-8-bromo-1,9-dihydro-6H-purin-6-one (205 mg), potassium carbonate (265 mg) and DMSO (3 mL), N-acetyl-L-cysteine (261 mg) was added at room temperature. The mixture was stirred at 80° C. for 2 hours. Potassium carbonate (531 mg) and N-acetyl-L-cysteine (261 mg) were added thereto. The mixture was stirred overnight at 80° C. After cooling to room temperature, water was added thereto, and the mixture was rendered acidic with 1 M hydrochloric acid and stirred at room temperature for 1 hour. The precipitate was collected by filtration and washed with water to obtain the title compound (233 mg).

MS: [M+H]$^+$ 403.2.

E) $N^2$-Acetyl-S-(2-amino-9-benzyl-6-oxo-6,9-dihydro-1H-purin-8-yl)-N-(21-chloro-3,6,9,12,15-pentaoxahenicos-1-yl)-L-cysteinamide Trifluoroacetate To a mixture of N-acetyl-S-(2-amino-9-benzyl-6-oxo-6,9-dihydro-1H-purin-8-yl)-L-cysteine (40 mg), WSC·HCl (24.77 mg), HOBt·H$_2$O (19.79 mg), a solution of 21-chloro-3,6,9,12,15-pentaoxahenicosan-1-amine hydrochloride in DMF (0.5 M, 0.24 mL) and anhydrous DMF (0.26 mL), DIPEA (0.052 mL) was added at room temperature. The mixture was stirred overnight at room temperature. Water was added to the mixture, followed by extraction with ethyl acetate. The organic layer was separated, washed with a saturated aqueous solution of sodium bicarbonate and saturated saline, then dried over anhydrous magnesium sulfate, and concentrated under reduced pressure. The residue was purified by HPLC (YMC-Actus Triart Prep C8-S, mobile phase: water/acetonitrile (system containing 0.1% TFA)) to obtain the title compound (24.3 mg).

$^1$H NMR (300 MHz, CD$_3$OD) δ 1.15-1.65 (8H, m), 1.68-1.83 (2H, m), 1.97 (3H, s), 3.35 (2H, t, J=4.7 Hz), 3.40-3.73 (22H, m), 4.67 (1H, dd, J=8.3, 4.5 Hz), 5.22 (2H, s), 7.12-7.43 (5H, m).

Example 21

$N^2$-Acetyl-S-(4-amino-1-(4-fluorobenzyl)-2-oxo-1,2-dihydropyrimidin-5-yl)-N-(21-chloro-3,6,9,12,15-pentaoxahenicos-1-yl)-L-cysteinamide Trifluoroacetate

A) 4-Amino-1-(4-fluorobenzyl)pyrimidin-2(1H)-one

To a mixture of cytosine (2 g) and anhydrous DMF (50 mL), 60% sodium hydride (0.864 g) was added at 0° C. The reaction mixture was stirred at 50° C. for 30 minutes. Then, 1-(bromomethyl)-4-fluorobenzene (3.74 g) was added thereto at room temperature. The mixture was stirred overnight at room temperature. Water was added thereto at 0° C., and the mixture was stirred at room temperature for 1 hour. The obtained precipitate was collected by filtration to obtain the title compound (3.67 g).

MS: [M+H]$^+$ 220.2.

B) 4-Amino-5-bromo-1-(4-fluorobenzyl)pyrimidin-2(1H)-one

To a mixture of 4-amino-1-(4-fluorobenzyl)pyrimidin-2(1H)-one (1.5 g) and anhydrous DMF (20 mL), NBS (1.340 g) was added at room temperature. The mixture was stirred at 50° C. for 30 minutes. After cooling to room temperature, water was added thereto, and the mixture was stirred at room temperature for 30 minutes. The precipitate was removed by filtration, and the filtrate was left at room temperature for 4 days. The obtained precipitate was collected and washed with water to obtain the title compound (377 mg).

MS: [M+H]$^+$ 298.1.

C) N-Acetyl-S-(4-amino-1-(4-fluorobenzyl)-2-oxo-1,2-dihydropyrimidin-5-yl)-L-cysteine To a mixture of 4-amino-5-bromo-1-(4-fluorobenzyl)pyrimidin-2(1H)-one (377 mg), potassium carbonate (1049 mg) and DMSO (3 mL), N-acetyl-L-cysteine (516 mg) was added at room temperature. The mixture was stirred overnight at 80° C. After cooling to room temperature, water was added thereto, and insoluble matter was removed by filtration through celite. The filtrate was washed with ethyl acetate and then rendered acidic with 1 M hydrochloric acid. The aqueous layer was concentrated under reduced pressure, and a small amount of water was added to the residue. The obtained precipitate was collected and washed with a small amount of water to obtain the title compound (114 mg).

MS: [M+H]$^+$ 381.1.

D) $N^2$-Acetyl-S-(4-amino-1-(4-fluorobenzyl)-2-oxo-1,2-dihydropyrimidin-5-yl)-N-(21-chloro-3,6,9,12,15-pentaoxahenicos-1-yl)-L-cysteinamide Trifluoroacetate To a mixture of N-acetyl-S-(4-amino-1-(4-fluorobenzyl)-2-oxo-1,2-dihydropyrimidin-5-yl)-L-cysteine (114 mg), WSC·HCl (74.7 mg), HOBt·H$_2$O (59.7 mg), 21-chloro-3,6, 9,12,15-pentaoxahenicosan-1-amine hydrochloride (141 mg) and anhydrous DMF (2 mL), DIPEA (0.157 mL) was added at room temperature. The mixture was stirred overnight at room temperature. Saturated saline was added to the mixture, followed by extraction with ethyl acetate. The organic layer was separated, washed with water and a saturated aqueous solution of sodium bicarbonate, then dried over anhydrous magnesium sulfate, and concentrated under reduced pressure. The residue was purified by HPLC (YMC-Actus Triart Prep C8-S, mobile phase: water/acetonitrile (system containing 0.1% TFA)) to obtain the title compound (18.2 mg).

$^1$H NMR (300 MHz, CD$_3$OD) δ 1.22-1.67 (8H, m), 1.69-1.84 (2H, m), 1.99 (3H, s), 3.34-3.40 (2H, m), 3.42-3.74 (22H, m), 4.69 (1H, t, J=7.0 Hz), 5.24 (2H, s), 6.20 (1H, s), 6.99-7.19 (2H, m), 7.25-7.52 (2H, m).

Example 26

N$^2$-Acetyl-N-(21-chloro-3,6,9,12,15-pentaoxahenicos-1-yl)-S-(9-(4-fluorobenzyl)-6-oxo-6,9-dihydro-1H-purin-8-yl)-L-cysteinamide A) 6-Chloro-9-(4-fluorobenzyl)-9H-purine To a mixture of 6-chloro-9H-purine (2.0 g), 1-(bromomethyl)-4-fluorobenzene (2.94 g) and acetonitrile (10 mL), potassium carbonate (2.68 g) was added at room temperature. The mixture was stirred overnight at room temperature. Water was added to the mixture at room temperature, followed by extraction with ethyl acetate. The organic layer was separated, washed with water and saturated saline, then dried over anhydrous magnesium sulfate, and concentrated under reduced pressure. The residue was purified by silica gel column chromatography (ethyl acetate/hexane) to obtain the title compound (1.53 g).

MS: [M+H]$^+$ 262.9.

B) 9-(4-Fluorobenzyl)-1,9-dihydro-6H-purin-6-one

To a mixture of 6-chloro-9-(4-fluorobenzyl)-9H-purine (1.00 g) and TFA (10 mL), water (2 mL) was added at room temperature. The mixture was stirred at 50° C. for 3 hours. The mixture was brought back to room temperature and then concentrated under reduced pressure. Water was added to the residue. The resulting solid was collected by filtration, washed with water, and then dried under reduced pressure to obtain the title compound (0.91 g).

MS: [M+H]$^+$ 245.0.

C) 8-Bromo-9-(4-fluorobenzyl)-1,9-dihydro-6H-purin-6-one

To a mixture of 9-(4-fluorobenzyl)-1,9-dihydro-6H-purin-6-one (300 mg) and DMF (3 mL), NBS (240 mg) was added at room temperature. The mixture was stirred overnight at 90° C. The reaction mixture was brought back to room temperature. Then, water was added thereto. The resulting solid was collected by filtration, washed with water, and dried under reduced pressure to obtain the title compound (345 mg).

$^1$H NMR (300 MHz, DMSO-d$_6$) δ 5.35 (2H, s), 7.13-7.24 (2H, m), 7.25-7.35 (2H, m), 8.11 (1H, d, J=3.9 Hz), 12.53 (1H, brs).

D) N-Acetyl-S-(9-(4-fluorobenzyl)-6-oxo-6,9-dihydro-1H-purin-8-yl)-L-cysteine

To a mixture of 8-bromo-9-(4-fluorobenzyl)-1,9-dihydro-6H-purin-6-one (70 mg), N-acetyl-L-cysteine (106 mg) and DMSO (1 mL), potassium carbonate (198 mg) was added at room temperature. The mixture was stirred at 60° C. for 4 hours. The reaction mixture was brought back to room temperature. Then, water was added thereto, and the pH of the mixture was further adjusted to 3 to 4 by the addition of 1 N hydrochloric acid. The resulting solid was collected by filtration, washed with water, and then dried under reduced pressure to obtain the title compound (15 mg).

MS: [M+H]$^+$ 406.1.

E) N$^2$-Acetyl-N-(21-chloro-3,6,9,12,15-pentaoxahenicos-1-yl)-S-(9-(4-fluorobenzyl)-6-oxo-6,9-dihydro-1H-purin-8-yl)-L-cysteinamide To a mixture of N-acetyl-S-(9-(4-fluorobenzyl)-6-oxo-6,9-dihydro-1H-purin-8-yl)-L-cysteine (14 mg), WSC·HCl (8.6 mg), HOBt·H$_2$O (6.9 mg) and DMF (1 mL), DIPEA (18 uL) was added at room temperature. The mixture was stirred overnight at room temperature. A saturated aqueous solution of sodium bicarbonate was added to the mixture, followed by extraction with ethyl acetate. The organic layer was separated, washed with water and saturated saline, then dried over anhydrous magnesium sulfate, and concentrated under reduced pressure. The residue was purified by HPLC (YMC-Actus Triart Prep C8-S, mobile phase: water/acetonitrile (system containing 0.1% TFA)) to obtain the title compound (4 mg).

$^1$H NMR (300 MHz, DMSO-d$_6$) δ 1.32-1.49 (4H, m), 1.51-1.62 (2H, m), 1.65-1.82 (2H, m), 1.92-1.99 (3H, m), 3.60 (26H, brs), 4.57-4.80 (1H, m), 5.27-5.43 (2H, m), 6.88-7.13 (2H, m), 7.25-7.42 (2H, m), 7.98-8.10 (1H, m), 8.25-8.43 (1H, m).

Example 27

S-(2-Acetamido-9-(4-fluorobenzyl)-6-oxo-6,9-dihydro-1H-purin-8-yl)-N$^2$-acetyl-N-(21-chloro-3,6,9,12,15-pentaoxahenicos-1-yl)-L-cysteinamide A) N-(8-Bromo-9-(4-fluorobenzyl)-6-oxo-6,9-dihydro-1H-purin-2-yl)acetamide To a mixture of 2-amino-8-bromo-9-(4-fluorobenzyl)-1,9-dihydro-6H-purin-6-one (300 mg), DMA (1 mL) and pyridine (3 mL), acetyl chloride (95 uL) was added at room temperature. The mixture was stirred at 80° C. for 5 hours. Acetyl chloride (1.89 mL) was added thereto, and the mixture was stirred at 80° C. for 10 minutes. Water was added to the mixture. The resulting solid was collected by filtration, washed with water, and then dried under reduced pressure to obtain the title compound (335 mg).

$^1$H NMR (300 MHz, DMSO-d$_6$) δ 2.18 (3H, s), 5.27 (2H, s), 7.13-7.39 (4H, m), 11.78 (1H, s), 12.12 (1H, s).

B) S-(2-Acetamido-9-(4-fluorobenzyl)-6-oxo-6,9-dihydro-1H-purin-8-yl)-N-acetyl-L-cysteine To a mixture of N-(8-bromo-9-(4-fluorobenzyl)-6-oxo-6,9-dihydro-1H-purin-2-yl)acetamide (70 mg), N-acetyl-L-cysteine (90 mg) and DMSO (1 mL), potassium carbonate (168 mg) was added at room temperature. The mixture was stirred at 60° C. for 4 hours. Insoluble matter was filtered off.

Then, water was added to the filtrate, and the pH of the mixture was further adjusted to 3 to 4 by the addition of 1 N hydrochloric acid. The resulting solid was collected by filtration, washed with water, and then dried under reduced pressure to obtain the title compound (45 mg).
MS: [M+H]$^+$ 463.1.

C) S-(2-Acetamido-9-(4-fluorobenzyl)-6-oxo-6,9-dihydro-1H-purin-8-yl)-N$^2$-acetyl-N-(21-chloro-3,6,9,12,15-pentaoxahenicos-1-yl)-L-cysteinamide To a mixture of S-(2-acetamido-9-(4-fluorobenzyl)-6-oxo-6,9-dihydro-1H-purin-8-yl)-N-acetyl-L-cysteine (45 mg), 21-chloro-3,6,9,12,15-pentaoxahenicosan-1-amine hydrochloride (42.0 mg), WSC·HCl (24.3 mg), HOBt·H$_2$O (19.4 mg) and DMF (1 mL), DIPEA (51 uL) was added at room temperature. The mixture was stirred overnight at room temperature. A saturated aqueous solution of sodium bicarbonate was added to the mixture, followed by extraction with ethyl acetate. The organic layer was separated, washed with water and saturated saline, then dried over anhydrous magnesium sulfate, and concentrated under reduced pressure. The residue was purified by HPLC (YMC-Actus Triart Prep C8-S, mobile phase: water/acetonitrile (system containing 0.1% TFA)) to obtain the title compound (2.0 mg).
$^1$H NMR (300 MHz, CD$_3$OD) δ 1.36-1.50 (4H, m), 1.58 (2H, quin, J=6.8 Hz), 1.76 (2H, quin, J=6.7 Hz), 1.98 (3H, s), 2.24 (3H, s), 3.37-3.76 (26H, m), 4.75 (1H, dd, J=8.5, 4.5 Hz), 5.27 (2H, s), 7.08 (2H, t, J=8.4 Hz), 7.35 (2H, dd, J=8.0, 5.6 Hz).

Example 30

N$^2$-Acetyl-S-(2-amino-9-(4-fluorobenzyl)-1-methyl-6-oxo-6,9-dihydro-1H-purin- 8-yl)-N— (21-chloro-3,6,9,12,15-pentaoxahenicos-1-yl)-L-cysteinamide A) 2-Amino-8-bromo-9-(4-fluorobenzyl)-1-methyl-1,9-dihydro-6H-purin-6-one To a mixture of 2-amino-8-bromo-9-(4-fluorobenzyl)-1, 9-dihydro-6H-purin-6-one (301 mg), iodomethane (190 mg) and anhydrous DMF (3 mL), 60% sodium hydride (42.7 mg) was added under ice cooling. The mixture was stirred overnight at room temperature. Water was added thereto at room temperature. The resulting precipitate was collected by filtration to obtain the title compound (291 mg).
MS: [M+H]$^+$ 352.0.

B) N-Acetyl-S-(2-amino-9-(4-fluorobenzyl)-1-methyl-6-oxo-6,9-dihydro-1H-purin-8-yl)-L-cysteine To a mixture of 2-amino-8-bromo-9-(4-fluorobenzyl)-1-methyl-1,9-dihydro-6H-purin-6-one (291 mg), potassium carbonate (685 mg) and DMSO (5 mL), N-acetyl-L-cysteine (405 mg) was added at room temperature. The mixture was stirred overnight at 80° C. After cooling to room temperature, water was added thereto, and the mixture was washed with ethyl acetate. The aqueous layer was rendered acidic with 2 N hydrochloric acid and stirred at room temperature for 1 hour. The precipitate was collected by filtration and washed with water to obtain the title compound (233 mg).
MS: [M+H]$^+$ 435.2.

C

To a mixture of N-acetyl-S-(2-amino-9-(4-fluorobenzyl)-1-methyl-6-oxo-6,9-dihydro-1H-purin-8-yl)-L-cysteine (50.0 mg), 21-chloro-3,6,9,12,15-pentaoxahenicosan-1-amine hydrochloride (54.2 mg), HOBt·H$_2$O (22.9 mg) and DMF (1 mL), WSC·HCl (28.7 mg) and DIPEA (0.060 mL) were added at room temperature, and the mixture was stirred at room temperature for 18 hours in a nitrogen atmosphere. The mixture was purified by silica gel column chromatography (MeOH/ethyl acetate) and then purified by HPLC (L-Column 2 ODS, mobile phase: water/acetonitrile (system containing 0.1% TFA)) to obtain the title compound (34.0 mg).
$^1$H NMR (300 MHz, DMSO-d$_6$) δ 1.16-1.58 (6H, m), 1.60-1.78 (2H, m), 1.84 (3H, s), 3.06-3.74 (29H, m), 4.39-4.58 (1H, m), 5.09 (2H, s), 7.01-7.31 (6H, m), 8.01-8.17 (1H, m), 8.43 (1H, d, J=8.2 Hz).

Example 31

2-Amino-8-(25-chloro-4,7,10,13,16,19-hexaoxapentacos-1-yl)-9-(4-fluorobenzyl)-1,9-dihydro-6H-purin-6-one A mixture of 2-amino-8-(25-chloro-4,7,10,13,16,19-hexaoxapentacos-1-yn-1-yl)-9-(4-fluorobenzyl)-1,9-dihydro-6H-purin-6-one (20 mg), 10% palladium carbon (8 mg) and MeOH (2 mL) was stirred at room temperature for 4 hours in a hydrogen atmosphere of normal pressure. The catalyst was filtered off, and the filtrate was concentrated under reduced pressure. The residue was purified by HPLC (L-Column 2 ODS, mobile phase: water/acetonitrile (system containing 0.1% TFA)). The obtained fraction was passed through MP-Carbonate resin and concentrated under reduced pressure to obtain the title compound (12 mg).
$^1$H NMR (300 MHz, CD$_3$OD) δ 1.26-1.50 (4H, m), 1.56 (2H, quin, J=6.8 Hz), 1.74 (2H, quin, J=6.9 Hz), 1.90 (2H, quin, J=6.6 Hz), 2.74 (2H, t, J=7.4 Hz), 3.40-3.67 (26H, m), 5.26 (2H, s), 7.00-7.14 (2H, m), 7.26 (2H, dd, J=8.0, 5.6 Hz).

Example 32

2-Amino-8-(23-chloro-5,8,11,14,17-pentaoxa-2-azatricos-1-yl)-9-(4-fluorobenzyl)-1,9-dihydro-6H-purin-6-one A) 2-Amino-9-(4-fluorobenzyl)-8-vinyl-1,9-dihydro-6H-purin-6-one A mixture of 2-amino-8-bromo-9-(4-fluorobenzyl)-1,9-dihydro-6H-purin-6-one (300 mg), 4,4,5,5-tetramethyl-2-vinyl- 1,3,2-dioxaborolane (205 mg), potassium carbonate (184 mg), palladium(II) acetate (9.96 mg), triphenylphosphine-3,3',3"-trisulfonic acid trisodium salt hydrate (52.0 mg), acetonitrile (2 mL) and water (1 mL) was stirred overnight at 100° C. The reaction mixture was brought back to room temperature. The solid was collected by filtration and washed with water and ethyl acetate to obtain the title compound (199 mg).
MS: [M+H]$^+$ 286.1.

B) 2-Amino-9-(4-fluorobenzyl)-6-oxo-6,9-dihydro-1H-purine- 8-carbaldehyde

To a mixture of 2-amino-9-(4-fluorobenzyl)-8-vinyl-1,9-dihydro-6H-purin-6-one (199 mg), osmium oxide (immobilized catalyst I) (38.0 mg), acetonitrile (15 mL) and water (15 mL), sodium periodate (597 mg) was added at 0° C. The mixture was stirred at room temperature for 3 days. The solid was collected by filtration and washed with ethyl acetate and water. The solid was further dissolved in hot DMSO and filtered. The filtrate was diluted with water. The resulting solid was collected by filtration and dried under reduced pressure to obtain the title compound (106 mg).

$^1$H NMR (300 MHz, DMSO-d$_6$) δ 5.47 (2H, s), 6.96 (2H, brs), 7.08-7.18 (2H, m), 7.21-7.35 (2H, m), 9.62 (1H, s), 10.99 (1H, brs).

C) 2-Amino- 8-(23-chloro-5,8,11,14,17-pentaoxa-2-azatricos-1-yl)-9-(4-fluorobenzyl)-1,9-dihydro-6H-purin- 6-one To a mixture of 2-amino-9-(4-fluorobenzyl)-6-oxo-6,9-dihydro-1H-purine-8-carbaldehyde (92 mg), 21-chloro-3,6,9,12,15-pentaoxahenicosan-1-amine hydrochloride (84 mg) and anhydrous THF (4 mL), TEA (43.2 mg) was added at room temperature. The reaction mixture was stirred at room temperature for 2 hours. Then, sodium triacetoxyborohydride (181 mg) was added thereto. The mixture was stirred at room temperature for 3 days. A saturated aqueous solution of sodium bicarbonate was added to the mixture at room temperature, followed by extraction with ethyl acetate. The organic layer was separated, washed with saturated saline, then dried over anhydrous sodium sulfate, and concentrated under reduced pressure. The residue was purified by silica gel column chromatography (ethyl acetate/methanol) and then purified by HPLC (L-Column 2 ODS, mobile phase: water/acetonitrile (system containing 0.1% TFA)). A saturated aqueous solution of sodium bicarbonate was added to the obtained fraction, followed by extraction with ethyl acetate. The organic layer was separated, dried over anhydrous sodium sulfate, and then concentrated under reduced pressure to obtain the title compound (54 mg).

$^1$H NMR (300 MHz, CD$_3$OD) δ 1.31-1.51 (4H, m), 1.56 (2H, quin, J=6.7 Hz), 1.75 (2H, quin, J=6.7 Hz), 2.73 (2H, t, J=5.0 Hz), 3.40-3.66 (22H, m), 3.79 (2H, s), 5.36 (2H, s), 6.99-7.12 (2H, m), 7.22-7.33 (2H, m).

Example 33

2-Amino-N-(21-chloro-3,6,9,12,15-pentaoxahenicos-1-yl)-9-(4-fluorobenzyl)-6-oxo-6,9-dihydro-1H-purine-8-carboxamide A) Methyl 2-amino-9-(4-fluorobenzyl)-6-oxo-6,9-dihydro-1H-purine-8-carboxylate To a mixture of 2-amino-8-bromo-9-(4-fluorobenzyl)-1,9-dihydro-6H-purin-6-one (400 mg), DMF (12 mL) and MeOH (3 mL), [1,1'-bis(diphenylphosphino)ferrocene]palladium(II) dichloride-dichloromethane adduct (43.3 mg) and TEA (239 mg) were added at room temperature. The mixture was stirred at 100° C. for 8 hours in a carbon monoxide atmosphere of 0.5 MPa. Water and ethyl acetate were added to the mixture at room temperature, and the deposited solid was collected by filtration to obtain the title compound (208 mg).
MS: [M+H]$^+$ 318.1.

B) 2-Amino-9-(4-fluorobenzyl)-6-oxo-6,9-dihydro-1H-purine-8-carboxylic acid

To a mixture of methyl 2-amino-9-(4-fluorobenzyl)-6-oxo-6,9-dihydro-1H-purine-8-carboxylate (205 mg) and MeOH (2.0 mL), a 2 N aqueous sodium hydroxide solution (0.969 mL) was added at room temperature. The mixture was stirred at room temperature for 10 minutes. The mixture was rendered slightly acidic by the addition of 1 N hydrochloric acid at room temperature and diluted with water. The deposited solid was collected by filtration to obtain the title compound (171 mg).
MS: [M+H]$^+$ 304.1.

C

To a mixture of 2-amino-9-(4-fluorobenzyl)-6-oxo-6,9-dihydro-1H-purine-8-carboxylic acid (14 mg) and anhydrous DMF (0.5 mL), 21-chloro-3,6,9,12,15-pentaoxahenicosan-1-amine hydrochloride (21.74 mg), WSC·HCl (9.74 mg), HOBt·H$_2$O (7.78 mg) and DIPEA (11.93 mg) were added at room temperature. The mixture was stirred at room temperature for 2 days. A saturated aqueous solution of sodium bicarbonate was added to the mixture at room temperature, followed by extraction with ethyl acetate. The organic layer was separated, washed with water and saturated saline, then dried over anhydrous sodium sulfate, and concentrated under reduced pressure. The residue was purified by HPLC (L-Column 2 ODS, mobile phase: water/acetonitrile (system containing 0.1% TFA)). The obtained fraction was passed through MP-Carbonate resin and concentrated under reduced pressure. The obtained residue was purified by HPLC (L-Column 2 ODS, mobile phase: water/acetonitrile (10 mM ammonium bicarbonate system)). The obtained fraction was concentrated under reduced pressure to obtain the title compound (12.5 mg).

$^1$H NMR (300 MHz, CD$_3$OD) δ 1.23-1.49 (4H, m), 1.55 (2H, quin, J=6.8 Hz), 1.73 (2H, quin, J=6.9 Hz), 3.43 (2H, t, J=6.5 Hz), 3.48-3.68 (22H, m), 5.66 (2H, s), 7.00 (2H, t, J=8.7 Hz), 7.39 (2H, dd, J=8.2, 5.6 Hz).

Example 34

N$^2$-Acetyl-N-(21-chloro-3,6,9,12,15-pentaoxahenicos-1-yl)-S-(9-(4-fluorobenzyl)-2,6-dioxo-2,3,6,9-tetrahydro-1H-purin-8-yl)-L-cysteinamide A) N-Acetyl-S-(9-(4-fluorobenzyl)-2,6-dioxo-2,3,6,9-tetrahydro-1H-purin-8-yl)-L-cysteine To a mixture of N-acetyl-S-(2-amino-9-(4-fluorobenzyl)-6-oxo-6,9-dihydro-1H-purin-8-yl)-L-cysteine (217 mg) and acetic acid (4 mL), a solution of sodium nitrite (71.2 mg) in water (0.2 mL) was added at room temperature. The mixture was stirred at room temperature for 30 minutes. A solution of sodium nitrite (55 mg) in water (0.2 mL) was added thereto at room temperature. The mixture was stirred at room temperature for 30 minutes. The reaction mixture was concentrated under reduced pressure. Then, water (about 2 mL) was added to the residue, and the mixture was stirred at 0° C. for 1 hour. The obtained solid was collected and washed with cold water to obtain the title compound (54.7 mg).
MS: [M+H]$^+$ 422.1.

B) N$^2$-Acetyl-N-(21-chloro-3,6,9,12,15-pentaoxahenicos-1-yl)-S-(9-(4-fluorobenzyl)-2,6-dioxo-2,3,6,9-tetrahydro-1H-purin-8-yl)-L-cysteinamide To a mixture of N-acetyl-S-(9-(4-fluorobenzyl)-2,6-dioxo-2,3,6,9-tetrahydro-1H-purin-8-yl)-L-cysteine (54.7 mg), WSC·HCl (32.3 mg), HOBt·H$_2$O (25.8 mg), 21-chloro-3,6,9,12,15-pentaoxahenicosan-1-amine hydrochloride (61.1 mg) and anhydrous DMF (2 mL), DIPEA (0.068 mL) was added at room temperature. The mixture was stirred at room temperature for 3 hours. Water was added to the mixture, followed by extraction with ethyl acetate. The organic layer was separated, washed with saturated saline, then dried over anhydrous magnesium sulfate, and concentrated under reduced pressure. The residue was purified by HPLC (YMC-Actus Triart Prep C8-S, mobile phase: water/acetonitrile (system containing 0.1% TFA)) to obtain the title compound (6.0 mg).

$^1$H NMR (300 MHz, CD$_3$OD) δ 1.15-1.83 (10H, m), 1.89-2.11 (3H, m), 3.12-3.40 (12H, m), 3.42-3.60 (14H, m), 4.46-4.76 (1H, m), 5.26 (2H, s), 6.92-7.38 (4H, m).

Example 35

N$^2$-Acetyl-N-(21-chloro-3,6,9,12,15-pentaoxahenicos-1-yl)-S-(9-(4-fluorobenzyl)-1-methyl-2,6-dioxo-2,3,6,9-tetrahydro-1H-purin-8-yl)-L-cysteinamide A) N-Acetyl-S-(9-(4-fluorobenzyl)-1-methyl-2,6-dioxo-2,3,6,9-tetrahydro-1H-purin-8-yl)-L-cysteine To a mixture of N-acetyl-S-(2-amino-9-(4-fluorobenzyl)-1-methyl-6-oxo-6,9-dihydro-1H-purin-8-yl)-L-cysteine (233 mg) and acetic acid (5 mL), a solution of sodium nitrite (148 mg) in water (0.2 mL) was added at room temperature. The mixture was stirred at room temperature for 30 minutes. A solution of sodium nitrite (148 mg) in water (0.2 mL) was added thereto at room temperature. The mixture was stirred at room temperature for 30 minutes. The reaction mixture was concentrated under reduced pressure. Then, water (about 2 mL) was added to the residue, and the mixture was stirred at 0° C. for 1 hour. The obtained solid was collected and washed with cold water to obtain the title compound (67.4 mg).

MS: [M+H]$^+$ 436.2.

B) N$^2$-Acetyl-N-(21-chloro-3,6,9,12,15-pentaoxahenicos-1-yl)-S-(9-(4-fluorobenzyl)-1-methyl-2,6-dioxo-2,3,6,9-tetrahydro-1H-purin-8-yl)-L-cysteinamide To a mixture of N-acetyl-S-(9-(4-fluorobenzyl)-1-methyl-2,6-dioxo-2,3,6,9-tetrahydro-1H-purin-8-yl)-L-cysteine (67.4 mg), HOBt·H$_2$O (30.8 mg), WSC·HCl (38.6 mg), 21-chloro-3,6,9,12,15-pentaoxahenicosan-1-amine hydrochloride (72.9 mg) and anhydrous DMF (2 mL), DIPEA (0.081 mL) was added at room temperature. The mixture was stirred at room temperature for 3 hours. Water was added to the mixture, followed by extraction with ethyl acetate. The organic layer was separated, washed with a saturated aqueous solution of hydrogen carbonate and saturated saline, then dried over anhydrous magnesium sulfate, and concentrated under reduced pressure. The residue was purified by HPLC (YMC-Actus Triart Prep C8-S, mobile phase: water/acetonitrile (system containing 0.1% TFA)) to obtain the title compound (19.9 mg).

$^1$H NMR (300 MHz, CD$_3$OD) δ 1.20-1.65 (8H, m), 1.68-1.85 (2H, m), 1.98 (3H, s), 2.94 (3H, s), 3.27-3.40 (6H, m), 3.41-3.68 (20H, m), 4.68 (1H, dd, J=8.3, 4.5 Hz), 5.18 (2H, s), 7.08 (2H, t, J=8.9 Hz), 7.36 (2H, dd, J=8.3, 5.7 Hz).

Example 44

N$^2$-Acetyl-N-(21-chloro-3,6,9,12,15-pentaoxahenicos-1-yl)-S-(3-(4-fluorobenzyl)-9-oxo-5,9-dihydro-3H-imidazo[1,2-a]purin-2-yl)-L-cysteinamide A) 2-Amino-8-bromo-1-(2,2-dimethoxyethyl)-9-(4-fluorobenzyl)-1,9-dihydro-6H-purin-6-one To a mixture of 2-amino-8-bromo-9-(4-fluorobenzyl)-1,9-dihydro-6H-purin-6-one (500 mg), 2-bromo-1,1-dimethoxyethane (375 mg) and DMF (5 mL), 60% sodium hydride (71.0 mg) was added under ice cooling, and the mixture was warmed to room temperature. The mixture was stirred at room temperature for 18 hours in a nitrogen atmosphere. Then, the mixture was warmed to 60° C. The mixture was stirred at 60° C. for 6 hours in a nitrogen atmosphere. Then, 2-bromo-1,1-dimethoxyethane (375 mg) was added to the mixture, and the mixture was warmed to 80° C. The mixture was stirred at 80° C. for 8 days in a nitrogen atmosphere. Then, water, THF and ethyl acetate were added to the mixture. The mixture was filtered, and insoluble matter was filtered off. The organic layer was separated. The organic layer was washed with saturated saline, then dried over anhydrous sodium sulfate, and concentrated under reduced pressure. The resulting crystals were washed with ethyl acetate and then collected by filtration to obtain the title compound (290 mg).

$^1$H NMR (300 MHz, DMSO-d$_6$) δ 3.31 (6H, s), 4.09 (2H, d, J=5.1 Hz), 4.62 (1H, t, J=5.1 Hz), 5.15 (2H, s), 7.09 (2H, s), 7.13-7.32 (4H, m).

B) 2-Bromo-3-(4-fluorobenzyl)-3,5-dihydro-9H-imidazo[1,2-a]purin-9-one

A mixture of 2-amino-8-bromo-1-(2,2-dimethoxyethyl)-9-(4-fluorobenzyl)-1,9-dihydro-6H-purin-6-one (250 mg), water (1 mL) and AcOH (4 mL) was stirred at 80° C. for 3 hours in a nitrogen atmosphere and then concentrated under reduced pressure. The resulting crystals were washed with MeOH to obtain the title compound (200 mg).

$^1$H NMR (300 MHz, DMSO-d$_6$) δ 5.29 (2H, s), 7.10-7.37 (4H, m), 7.48 (1H, d, J=2.4 Hz), 7.66 (1H, d, J=2.4 Hz), 12.65 (1H, brs).

C) N-Acetyl-S-(3-(4-fluorobenzyl)-9-oxo-5,9-dihydro-3H-imidazo[1,2-a]purin-2-yl)-L-cysteine To a mixture of 2-bromo-3-(4-fluorobenzyl)-3,5-dihydro-9H-imidazo[1,2-a]purin-9-one (80.0 mg), N-acetyl-L-cysteine (108 mg) and DMSO (1.6 mL), potassium carbonate (201 mg) was added at room temperature, and the mixture was stirred at 80° C. for 2 hours in a nitrogen atmosphere. Water (8 mL) was added to the mixture, and the pH of the aqueous mixture was adjusted to 4 with 6 N hydrochloric acid. The crystals were collected by filtration and washed with water to obtain the title compound (90.0 mg).

MS: [M+H]$^+$ 445.1.

D) N$^2$-Acetyl-N-(21-chloro-3,6,9,12,15-pentaoxahenicos-1-yl)-S-(3-(4-fluorobenzyl)-9-oxo-5,9-dihydro-3H-imidazo[1,2-a]purin-2-yl)-L-cysteinamide To a mixture of N-acetyl-S-(3-(4-fluorobenzyl)-9-oxo-5,9-dihydro-3H-imidazo[1,2-a]purin-2-yl)-L-cysteine (50.0 mg), 21-chloro-3,6,9,12,15-pentaoxahenicosan-1-amine hydrochloride (53.0 mg), HOBt·H$_2$O (22.4 mg) and DMF (1 mL), WSC·HCl (28.0 mg) and DIPEA (0.059 mL) were added at room temperature, and the mixture was stirred at room temperature for 14 hours in a nitrogen atmosphere. The mixture was purified by silica gel column chromatography (ethyl acetate/hexane) and then purified by HPLC (L-Column 2 ODS, mobile phase: water/acetonitrile (system containing 0.1% TFA)) to obtain the title compound (31.2 mg).

$^1$H NMR (300 MHz, DMSO-$d_6$) δ 1.20-1.55 (6H, m), 1.69 (2H, quin, J=6.8 Hz), 1.85 (3H, s), 3.10-3.70 (26H, m), 4.47-4.64 (1H, m), 5.21 (2H, s), 7.08-7.34 (4H, m), 7.45 (1H, brs), 7.65 (1H, s), 8.12 (1H, t, J=5.4 Hz), 8.43 (1H, d, J=7.9 Hz), 12.56 (1H, brs).

Example 45

N$^2$-Acetyl-N-(21-chloro-3,6,9,12,15-pentaoxahenicos-1-yl)-S-(2,6-diamino-9-(4-fluorobenzyl)-9H-purin-8-yl)-L-cysteinamide A) 9-(4-Fluorobenzyl)-9H-purine-2,6-diamine A mixture of a solution of 2 M ammonia in methanol (9 mL), 25% ammonia water (3 mL) and 6-chloro-9-(4-fluorobenzyl)-9H-purin-2-amine (600 mg) was irradiated with microwave at 120° C. for 105 minutes, and the mixture was concentrated under reduced pressure. The resulting crystals were washed with ethyl acetate, then collected by filtration, and recrystallized from MeOH/water to obtain the title compound (490 mg).

MS: [M+H]$^+$ 259.1.

B) 8-Bromo-9-(4-fluorobenzyl)-9H-purine-2,6-diamine

To a mixture of 9-(4-fluorobenzyl)-9H-purine-2,6-diamine (450 mg), acetonitrile (20 mL) and water (5 mL), NBS (341 mg) was added under ice cooling, and the mixture was warmed to room temperature in a nitrogen atmosphere. The mixture was stirred at room temperature for 1 hour. Then, sodium sulfite (65.9 mg) was added to the mixture, and the mixture was stirred for 1 hour. The resulting crystals were collected by filtration and dissolved in a mixed solution of ethyl acetate, DMSO and MeOH. The mixture was purified by silica gel column chromatography (NH, MeOH/ethyl acetate), and a fraction containing the title compound was concentrated under reduced pressure to obtain a solution of the title compound in DMSO. Water was added to the obtained solution of the title compound in DMSO. The resulting crystals were collected by filtration to obtain the title compound (240 mg).

$^1$H NMR (300 MHz, DMSO-$d_6$) δ 5.16 (2H, s), 5.97 (2H, s), 6.88 (2H, brs), 7.10-7.32 (4H, m).

C) N-Acetyl-S-(2,6-diamino-9-(4-fluorobenzyl)-9H-purin-8-yl)-L-cysteine

To a mixture of 8-bromo-9-(4-fluorobenzyl)-9H-purine-2,6-diamine (80 mg), N-acetyl-L-cysteine (116 mg) and DMSO (1.6 mL), potassium carbonate (216 mg) was added at room temperature, and the mixture was stirred at 80° C. for 2 hours in a nitrogen atmosphere. Water (8 mL) was added to the mixture, and the pH of the aqueous mixture was adjusted to 4 with 6 N hydrochloric acid. The crystals were collected by filtration and washed with water to obtain the title compound (100 mg).

MS: [M+H]$^+$ 420.1.

D) N$^2$-Acetyl-N-(21-chloro-3,6,9,12,15-pentaoxahenicos-1-yl)-S-(2,6-diamino-9-(4-fluorobenzyl)-9H-purin-8-yl)-L-cysteinamide To a mixture of N-acetyl-S-(2,6-diamino-9-(4-fluorobenzyl)-9H-purin-8-yl)-L-cysteine (50 mg), 21-chloro-3,6,9,12,15-pentaoxahenicosan-1-amine hydrochloride (56.1 mg), HOBt·H$_2$O (23.7 mg) and DMF (1 mL), WSC·HCl (29.7 mg) and DIPEA (0.062 mL) were added at room temperature, and the mixture was stirred at room temperature for 14 hours in a nitrogen atmosphere. The mixture was purified by silica gel column chromatography (ethyl acetate/hexane) and then purified by HPLC (L-Column 2 ODS, mobile phase: water/acetonitrile (system containing 0.1% TFA)). The obtained fraction was passed through MP-Carbonate resin and concentrated under reduced pressure to obtain the title compound (31.1 mg).

$^1$H NMR (300 MHz, DMSO-$d_6$) δ 1.18-1.58 (6H, m), 1.61-1.77 (2H, m), 1.82 (3H, s), 3.08-3.68 (26H, m), 4.43-4.62 (1H, m), 5.10 (2H, s), 5.86 (2H, s), 6.69 (2H, brs), 7.07-7.29 (4H, m), 8.10 (1H, brs), 8.29 (1H, d, J=8.0 Hz).

Example 46

1-((2-Amino-9-(4-fluorobenzyl)-6-oxo-6,9-dihydro-1H-purin-8-yl)carbonyl)-N-(21-chloro-3,6,9,12,15-pentaoxahenicos-1-yl)piperidine-2-carboxamide A) Methyl 1-((2-amino-9-(4-fluorobenzyl)-6-oxo-6,9-dihydro-1H-purin-8-yl)carbonyl)piperidine-2-carboxylate To a mixture of 2-amino-9-(4-fluorobenzyl)-6-oxo-6,9-dihydro-1H-purine-8-carboxylic acid (100 mg) and anhydrous DMF (4 mL), methyl piperidine-2-carboxylate monohydrochloride (65.2 mg), WSC·HCl (69.5 mg), HOBt·H$_2$O (55.5 mg) and DIPEA (85 mg) were added at room temperature. The mixture was stirred at room temperature for 2 days. A saturated aqueous solution of sodium bicarbonate was added to the mixture at room temperature, followed by extraction with ethyl acetate. The organic layer was separated, washed with water and saturated saline, then dried over anhydrous sodium sulfate, and concentrated under reduced pressure to obtain a partially purified product of the title compound (108 mg).

MS: [M+H]$^+$ 429.1.

B) 1-((2-Amino-9-(4-fluorobenzyl)-6-oxo-6,9-dihydro-1H-purin-8-yl)carbonyl)piperidine-2-carboxylic Acid To a mixture of methyl 1-((2-amino-9-(4-fluorobenzyl)-6-oxo-6,9-dihydro-1H-purin-8-yl)carbonyl)piperidine-2-carboxylate (108 mg), THF (1.600 mL) and MeOH (0.8 mL), a 2 N aqueous sodium hydroxide solution (0.378 mL) was added at room temperature. The mixture was stirred at room temperature for 4 hours. The mixture was rendered slightly acidic by the addition of 1 N hydrochloric acid at room temperature and diluted with water. The deposited solid was collected by filtration to obtain the title compound (56.2 mg).

MS: [M+H]$^+$ 415.2.

C) 1-((2-Amino-9-(4-fluorobenzyl)-6-oxo-6,9-dihydro-1H-purin-8-yl)carbonyl)-N-(21-chloro-3,6,9,12,15-pentaoxahenicos-1-yl)piperidine-2-carboxamide To a mixture of 1-((2-amino-9-(4-fluorobenzyl)-6-oxo-6,9-dihydro-1H-purin-8-yl)carbonyl)piperidine-2-carboxylic acid (56.2 mg) and anhydrous DMF (1.4 mL), 21-chloro-3,6,9,12,15-pentaoxahenicosan-1-amine hydrochloride (58.5 mg), WSC·HCl (28.6 mg), HOBt·H$_2$O (22.85 mg) and DIPEA (35.1 mg) were added at room temperature. The mixture was stirred at room temperature for 2 days. A saturated aqueous solution of sodium bicarbonate was added to the mixture at room temperature, followed by extraction with ethyl acetate. The organic layer was separated, washed with water and saturated saline, then dried over anhydrous sodium sulfate, and concentrated under reduced pressure. The residue was purified by silica gel column chromatography (ethyl acetate/methanol), and the residue was purified by HPLC (L-Column 2 ODS, mobile phase: water/acetonitrile (system containing 0.1% TFA)). The obtained fraction was passed through MP-Carbonate resin and concentrated under reduced pressure to obtain the title compound (76 mg).

$^1$H NMR (300 MHz, CD$_3$OD) δ 0.83-1.16 (1H, m), 1.29-1.82 (12H, m), 2.20-3.00 (1H, m), 3.35-3.49 (4H, m), 3.50-3.69 (20H, m), 3.73-4.07 (1H, m), 4.38-4.84 (1H, m), 4.94-5.23 (1H, m), 5.25-5.57 (2H, m), 7.06 (2H, t, J=8.3 Hz), 7.32 (2H, brs).

Example 47

2-Amino-N-(14-((6S)-4-(4-chlorophenyl)-2,3,9-trimethyl-6H-thieno[3,2-f][1,2,4]triazolo[4,3-a][1,4]diazepin-6-yl)-13-oxo-3,6,9-trioxa-12-azatetradec- 1-yl)-9-(4-fluorobenzyl)-6-oxo-6,9-dihydro-1H-purine-8-carboxamide

A) N-(2-(2-(2-(2-Aminoethoxy)ethoxy)ethoxy)ethyl)-2-((6S)-4-(4-chlorophenyl)-2,3,9-trimethyl-6H-thieno[3,2-f][1,2,4]triazolo[4,3-a][1,4]diazepin-6-yeacetamide To a mixture of ((6S)-4-(4-chlorophenyl)-2,3,9-trimethyl-6H-thieno[3,2-f][1,2,4]triazolo[4,3-a][1,4]diazepin-6-yeacetic acid (500 mg), 2,2'-(oxybis(ethane-2,1-diyloxy)) diethanamine (528 mg), HATU (711 mg) and DMF (3 ml), DIPEA (436 uL) was added at room temperature. The mixture was stirred overnight at room temperature. Water was added to the mixture at room temperature, followed by extraction with ethyl acetate. The organic layer was separated, washed with a saturated aqueous solution of sodium bicarbonate and saturated saline, then dried over anhydrous magnesium sulfate, and concentrated under reduced pressure. The residue was purified by silica gel column chromatography (NH, ethyl acetate/hexane) to obtain the title compound (68 mg).

The ((6S)-4-(4-chlorophenyl)-2,3,9-trimethyl-6H-thieno[3,2-f][1,2,4]triazolo[4,3-a][1,4]diazepin-6-yl)acetic acid used was a compound synthesized according to a method known per se in the art (e.g., a method described in Nature, 2010, 468, 1067-1073) and purified by chiral HPLC.

MS: [M+H]$^+$ 575.1.

B) 2-Amino-N-(14-((6S)-4-(4-chlorophenyl)-2,3,9-trimethyl-6H-thieno[3,2-f][1,2,4]triazolo[4,3-a][1,4]diazepin-6-yl)-13-oxo-3,6,9-trioxa-12-azatetradec-1-yl)-9-(4-fluorobenzyl)-6-oxo-6,9-dihydro-1H-purine-8-carboxamide To a mixture of 2-amino-9-(4-fluorobenzyl)-6-oxo-6,9-dihydro-1H-purine-8-carboxylic acid (17.93 mg) and anhydrous DMF (1 mL), N-(2-(2-(2-(2-aminoethoxy)ethoxy)ethoxy)ethyl)-2-46S)-4-(4-chlorophenyl)-2,3,9-trimethyl-6H-thieno[3,2-f][1,2,4]triazolo[4,3-a][1,4]diazepin-6-yl) acetamide (34 mg), WSC·HCl (12.47 mg), HOBt·H$_2$O (9.96 mg) and DIPEA (15.28 mg) were added at room temperature. The mixture was stirred overnight at room temperature. A saturated aqueous solution of sodium bicarbonate was added to the mixture at room temperature, followed by extraction with ethyl acetate. The organic layer was separated, washed with water and saturated saline, then dried over anhydrous sodium sulfate, and concentrated under reduced pressure. The residue was purified by HPLC (L-Column 2 ODS, mobile phase: water/acetonitrile (system containing 0.1% TFA)). The obtained fraction was passed through MP-Carbonate resin and concentrated under reduced pressure to obtain the title compound (16.3 mg).

$^1$H NMR (300 MHz, CD$_3$OD) δ 1.66 (3H, s), 2.40 (3H, s), 2.67 (3H, s), 3.34-3.52 (6H, m), 3.53-3.68 (12H, m), 4.66 (1H, dd, J=8.7, 5.5 Hz), 5.63 (2H, s), 6.97 (2H, t, J=8.7 Hz), 7.31-7.49 (6H, m).

Example 48

3-(2-Amino-9-(4-fluorobenzyl)-6-oxo-6,9-dihydro-1H-purin-8-yl)-N-(14-((6S)-4-(4-chlorophenyl)-2,3,9-trimethyl-6H-thieno[3,2-f][1,2,4]triazolo[4,3-a][1,4]diazepin-6-yl)-13-oxo-3,6,9-trioxa-12-azatetradec-1-yl)benzamide

A) 3-(2-Amino-9-(4-fluorobenzyl)-6-oxo-6,9-dihydro-1H-purin-8-yl)benzoic Acid A mixture of 2-amino-8-bromo-9-(4-fluorobenzyl)-1,9-dihydro-6H-purin-6-one (300 mg), (3-(methoxycarbonyl)phenyl)boronic acid (192 mg), palladium(II) acetate (9.96 mg), triphenylphosphine-3,3',3"-trisulfonic acid trisodium salt hydrate (52.0 mg), potassium carbonate (184 mg), acetonitrile (2 mL) and water (1 mL) was stirred overnight at 100° C. The reaction mixture was brought back to room temperature, and the solution was rendered basic by the addition of a 2 M aqueous sodium hydroxide solution. After washing with ethyl acetate, the pH of the obtained aqueous layer was adjusted to 4 to 5 with 1 M hydrochloric acid. The resulting solid was collected by filtration and dried under reduced pressure to obtain the title compound (324 mg).

MS: [M+H]$^+$ 380.1.

B) 3-(2-Amino-9-(4-fluorobenzyl)-6-oxo-6,9-dihydro-1H-purin-8-yl)-N-(14-((6S)-4-(4-chlorophenyl)-2,3,9-trimethyl-6H-thieno[3,2-f][1,2,4]triazolo[4,3-a][1,4]diazepin-6-yl)-13-oxo-3,6,9-trioxa-12-azatetradec-1-yl)benzamide To a mixture of 3-(2-amino-9-(4-fluorobenzyl)-6-oxo-6,9-dihydro-1H-purin-8-yl)benzoic acid (22.43 mg) and anhydrous DMF (1.0 mL), N-(2-(2-(2-(2-aminoethoxy)ethoxy)ethoxy)ethyl)-2-46S)-4-(4-chlorophenyl)-2,3,9-trimethyl-6H-thieno[3,2-f][1,2,4]triazolo[4,3-a][1,4]diazepin-6-yl)acetamide (34 mg), WSC·HCl (12.47 mg), HOBt·H$_2$O (9.96 mg), and DIPEA (15.28 mg) were added at room temperature. The mixture was stirred overnight at room temperature. A saturated aqueous solution of sodium bicarbonate was added to the mixture at room temperature, followed by extraction with ethyl acetate. The organic layer was separated, washed with water and saturated saline, then dried over anhydrous sodium sulfate, and concentrated under reduced pressure. The residue was purified by HPLC (L-Column 2 ODS, mobile phase: water/acetonitrile (system containing 0.1% TFA)). The obtained fraction was passed through MP-Carbonate resin and concentrated under reduced pressure to obtain the title compound (36 mg).

$^1$H NMR (300 MHz, CD$_3$OD) δ 1.66 (3H, s), 2.41 (3H, s), 2.67 (3H, s), 3.33-3.48 (4H, m), 3.49-3.72 (14H, m), 4.62 (1H, dd, J=8.5, 5.5 Hz), 5.33 (2H, s), 6.90-7.09 (4H, m), 7.32-7.55 (5H, m), 7.65 (1H, d, J=7.6 Hz), 7.89 (1H, d, J=7.7 Hz), 7.99 (1H, s).

Example 49

N$^2$-Acetyl-S-(2-amino-9-(4-methylbenzyl)-6-oxo-6,9-dihydro-1H-purin-8-yl)-N-(14-((6S)-4-(4-chlorophenyl)-2,3,9-trimethyl-6H-thieno[3,2-f][1,2,4]triazolo[4,3-a][1,4]diazepin-6-yl)-13-oxo-3,6,9-trioxa-12-azatetradec-1-yl)-L-cysteinamide A) tert-Butyl (14-((6S)-4-(4-chlorophenyl)-2,3,9-trimethyl-6H-thieno[3,2-f][1,2,4]triazolo[4,3-a][1,4]diazepin-6-yl)-13-oxo-3,6,9-trioxa-12-azatetradec-1-yl)carbamate To a mixture of ((6S)-4-(4-chlorophenyl)-2,3,9-trimethyl-6H-thieno[3,2-f][1,2,4]triazolo[4,3-a][1,4]diazepin-6-yeacetic acid (500 mg), tert-butyl (2-(2-(2-(2-aminoethoxy)ethoxy)ethoxy)ethyl)carbamate (401 mg), HATU (711 mg) and DMF (3 mL), DIPEA (322 mg) was added at room temperature. The mixture was stirred overnight at room temperature. Water was added to the mixture at room temperature, followed by extraction with ethyl acetate. The organic layer was separated, washed with water and saturated saline, then dried over anhydrous magnesium sulfate, and concentrated under reduced pressure. The residue was purified by silica gel column chromatography (NH, methanol/ethyl acetate) to obtain the title compound (720 mg).

MS: [M+H]$^+$ 675.1.

B) N-(2-(2-(2-(2-Aminoethoxy)ethoxy)ethoxy)ethyl)-2-((6S)-4-(4-chlorophenyl)-2,3,9-trimethyl-6H-thieno[3,2-f][1,2,4]triazolo[4,3-a][1,4]diazepin-6-yeacetamide hydrochloride A mixture of tert-butyl (14-((6S)-4-(4-chlorophenyl)-2,3,9-trimethyl-6H-thieno[3,2-f][1,2,4]triazolo[4,3-a][1,4]diazepin-6-yl)-13-oxo-3,6,9-trioxa-12-azatetradec-1-yl)carbamate (480 mg) and 2 M hydrochloric acid in methanol (2.0 mL) was stirred at room temperature for 1 hour. The mixture was concentrated under reduced pressure to obtain the title compound (435 mg).

MS: [M+H]$^+$ 575.1.

C) N$^2$-Acetyl-S-(2-amino-9-(4-methylbenzyl)-6-oxo-6,9-dihydro-1H-purin-8-yl)-N-(14-((6S)-4-(4-chlorophenyl)-2,3,9-trimethyl-6H-thieno[3,2-f][1,2,4]triazolo[4,3-a][1,4]diazepin-6-yl)-13-oxo-3,6,9-trioxa-12-azatetradec-1-yl)-L-cysteinamide To a mixture of N-acetyl-S-(2-amino-9-(4-methylbenzyl)-6-oxo-6,9-dihydro-1H-purin-8-yl)-L-cysteine (30 mg), N-(2-(2-(2-(2-aminoethoxy)ethoxy)ethoxy)ethyl)-2-((6S)-4-(4-chlorophenyl)-2,3,9-trimethyl-6H-thieno[3,2-f][1,2,4]triazolo[4,3-a][1,4]diazepin-6-yeacetamide hydrochloride (49 mg), WSC·HCl (18 mg), HOBt (13 mg) and DMF (1 mL), TEA (0.015 mL) was added at room temperature. The mixture was stirred overnight at room temperature. Water was added to the mixture at room temperature, followed by extraction with ethyl acetate. The organic layer was separated, washed with water and saturated saline, then dried over anhydrous sodium sulfate, and concentrated under reduced pressure. The residue was purified by HPLC (L-Column 2 ODS, mobile phase: water/acetonitrile (system containing 0.1% TFA)). A saturated aqueous solution of sodium bicarbonate was added to the obtained fraction, followed by extraction with ethyl acetate. The organic layer was separated, dried over anhydrous magnesium sulfate, and then concentrated under reduced pressure to obtain the title compound (12 mg).

$^1$H NMR (300 MHz, DMSO-d$_6$) δ 1.62 (3H, s), 1.84 (3H, s), 2.25 (3H, s), 2.41 (3H, s), 2.57-2.62 (3H, m), 3.13-3.30 (6H, m), 3.36-3.55 (14H, m), 4.43-4.55 (2H, m), 5.04 (2H, s), 6.52 (2H, brs), 7.00-7.07 (2H, m), 7.08-7.16 (2H, m), 7.38-7.45 (2H, m), 7.45-7.52 (2H, m), 8.09 (1H, t, J=5.7 Hz), 8.29 (1H, t, J=6.0 Hz), 8.42 (1H, d, J=7.6 Hz), 10.64 (1H, s).

Example 50

N$^2$-Acetyl-S-(2-amino-9-(4-chlorobenzyl)-6-oxo-6,9-dihydro-1H-purin-8-yl)-N-(14-((6S)-4-(4-chlorophenyl)-2,3,9-trimethyl-6H-thieno[3,2-f][1,2,4]triazolo[4,3-a][1,4]diazepin-6-yl)-13-oxo-3,6,9-trioxa-12-azatetradec-1-yl)-L-cysteinamide To a mixture of N-acetyl-S-(2-amino-9-(4-chlorobenzyl)-6-oxo-6,9-dihydro-1H-purin-8-yl)-L-cysteine (30 mg), N-(2-(2-(2-(2-aminoethoxy)ethoxy)ethoxy)ethyl)-2-((6S)-4-(4-chlorophenyl)-2,3,9-trimethyl-6H-thieno[3,2-f][1,2,4]triazolo[4,3-a][1,4]diazepin-6-yeacetamide hydrochloride (46 mg), WSC·HCl (17 mg), HOBt (12 mg) and DMF (1 mL), TEA (0.014 mL) was added at room temperature. The mixture was stirred overnight at room temperature. Water was added to the mixture at room temperature, followed by extraction with ethyl acetate. The organic layer was separated, washed with water and saturated saline, then dried over anhydrous sodium sulfate, and concentrated under reduced pressure. The residue was purified by HPLC (L-Column 2 ODS, mobile phase: water/acetonitrile (system containing 0.1% TFA)). A saturated aqueous solution of sodium bicarbonate was added to the obtained fraction, followed by extraction with ethyl acetate. The organic layer was separated, dried over anhydrous sodium sulfate, and then concentrated under reduced pressure to obtain the title compound (11 mg).

$^1$H NMR (300 MHz, DMSO-d$_6$) δ 1.62 (3H, s), 1.84 (3H, s), 2.41 (3H, s), 2.59 (3H, s), 3.13-3.30 (6H, m), 3.35-3.55 (14H, m), 4.42-4.55 (2H, m), 5.09 (2H, s), 6.55 (2H, brs), 7.16 (2H, d, J=8.1 Hz), 7.35-7.53 (6H, m), 8.08 (1H, t, J=6.0 Hz), 8.28 (1H, t, J=5.5 Hz), 8.40 (1H, d, J=8.6 Hz), 10.68 (1H, brs).

Example 51

$N^2$-Acetyl-S-(2-amino-9-(4-fluorobenzyl)-6-oxo-6, 9-dihydro-1H-purin- 8-yl)-N-(14-((6S)-4-(4-chlorophenyl)-2,3,9-trimethyl-6H-thieno[3,2-f][1,2,4]triazolo[4,3-a][1,4]diazepin-6-yl)-13-oxo-3,6,9-trioxa-12-azatetradec-1-yl)-L-cysteinamide To a mixture of N-acetyl-S-(2-amino-9-(4-fluorobenzyl)-6-oxo-6,9-dihydro-1H-purin-8-yl)-L-cysteine (20.6 mg), N-(2-(2-(2-(2-aminoethoxy)ethoxy)ethyl)-2-((6S)-4-(4-chlorophenyl)-2,3,9-trimethyl-6H-thieno[3,2-f][1,2,4]triazolo[4,3-a][1,4]diazepin-6-yeacetamide hydrochloride (30 mg), WSC·HCl (12 mg), HOBt·H$_2$O (9.8 mg) and DMF (1 mL), DIPEA (26 uL) was added at room temperature. The mixture was stirred overnight at room temperature. A saturated aqueous solution of sodium bicarbonate was added to the mixture, followed by extraction with ethyl acetate. The organic layer was separated, washed with water and saturated saline, then dried over anhydrous magnesium sulfate, and concentrated under reduced pressure. The residue was purified by silica gel column chromatography (NH, methanol/ethyl acetate) to obtain the title compound (14 mg).

$^1$H NMR (300 MHz, CD$_3$OD) δ 1.59 (3H, s), 1.91 (3H, s), 2.33 (3H, s), 2.58 (3H, s), 3.24-3.60 (21H, m), 4.44-4.65 (2H, m), 4.98-5.09 (2H, m), 6.88-7.00 (2H, m), 7.20 (2H, dd, J=8.0, 5.6 Hz), 7.25-7.41 (4H, m).

Example 52

(2E)-3-(2-Amino-9-(4-fluorobenzyl)-6-oxo-6,9-dihydro-1H-purin-8-yl)-N-(14-((6S)-4-(4-chlorophenyl)-2,3,9-trimethyl-6H-thieno[3,2-f][1,2,4]triazolo[4,3-a][1,4]diazepin-6-yl)-13-oxo-3,6,9-trioxa-12-azatetradec-1-yl)acrylamide To a mixture of (2E)-3-(2-amino-9-(4-fluorobenzyl)-6-oxo-6,9-dihydro-1H-purin-8-yl)acrylic acid (16.2 mg), N-(2-(2-(2-(2-aminoethoxy)ethoxy)ethyl)-2-46S)-4-(4-chlorophenyl)-2,3,9-trimethyl-6H-thieno[3,2-f][1,2,4]triazolo[4,3-a][1,4]diazepin-6-yeacetamide hydrochloride (30 mg), WSC·HCl (12.2 mg), HOBt·H$_2$O (9.8 mg) and DMF (1 mL), DIPEA (19 mg) was added at room temperature. The mixture was stirred at room temperature for 5 hours. A saturated aqueous solution of sodium bicarbonate was added to the mixture, followed by extraction with ethyl acetate. The organic layer was separated, washed with water and saturated saline, then dried over anhydrous sodium sulfate, and concentrated under reduced pressure. The residue was purified by silica gel column chromatography (methanol/ethyl acetate) to obtain the title compound (20 mg).

$^1$H NMR (300 MHz, CD$_3$OD) δ 1.69 (3H, s), 2.44 (3H, s), 2.70 (3H, s), 3.65 (19H, s), 4.59-4.72 (1H, m), 5.36 (2H, s), 6.92-7.01 (1H, m), 7.05 (2H, t, J=8.3 Hz), 7.20-7.33 (1H, m), 7.35-7.57 (5H, m).

Example 53

$N^2$-Acetyl-N-(14-((6S)-4-(4-chlorophenyl)-2,3,9-trimethyl-6H-thieno[3,2-f][1,2,4]triazolo[4,3-a][1,4]diazepin-6-yl)-13-oxo-3,6,9-trioxa-12-azatetradec-1-yl)-S-(9-(4-fluorobenzyl)-1,3-dimethyl-2,6-dioxo-2,3,6,9-tetrahydro-1H-purin-8-yl)-L-cysteinamide To a mixture of N-acetyl-S-(9-(4-fluorobenzyl)-1,3-dimethyl-2,6-dioxo-2,3,6,9-tetrahydro-1H-purin-8-yl)-L-cysteine (25.5 mg), WSC·HCl (12.41 mg), HOBt·H$_2$O (9.92 mg), N-(2-(2-(2-(2-aminoethoxy)ethoxy)ethyl)-2-((6S)-4-(4-chlorophenyl)-2,3,9-trimethyl-6H-thieno[3,2-f][1,2,4]triazolo[4,3-a][1,4]diazepin-6-yeacetamide hydrochloride (33 mg), and anhydrous DMF (2 mL), DIPEA (0.028 mL) was added at room temperature. The mixture was stirred at room temperature for 3 hours. Water was added to the mixture, followed by extraction with ethyl acetate. The organic layer was separated, washed with saturated saline, then dried over anhydrous magnesium sulfate, and concentrated under reduced pressure. The residue was purified by HPLC (YMC-Actus Triart Prep C8-S, mobile phase: water/acetonitrile (system containing 0.1% TFA)) to obtain the title compound (7.1 mg).

$^1$H NMR (300 MHz, CD$_3$OD) δ 1.70 (3H, s), 1.95 (3H, s), 2.45 (3H, s), 2.74 (3H, s), 3.26-3.39 (6H, m), 3.40-3.67 (19H, m), 3.73 (1H, dd, J=13.8, 5.5 Hz), 4.58-4.79 (2H, m), 5.42 (2H, s), 7.04 (2H, t, J=8.7 Hz), 7.25-7.56 (6H, m).

Example 54

(2E)-N— (14-((6S)-4-(4-Chlorophenyl)-2,3,9-trimethyl-6H-thieno[3,2-f][1,2,4]triazolo[4,3-a][1,4]diazepin-6-yl)-13-oxo-3,6,9-trioxa-12-azatetradec- 1-yl)-3-(9-(4-fluorobenzyl)-1,3-dimethyl-2,6-dioxo-2,3,6,9-tetrahydro-1H-purin- 8-yl)acrylamide

A) (2E)-3-(9-(4-Fluorobenzyl)-1,3-dimethyl-2,6-dioxo-2,3,6,9-tetrahydro-1H-purin-8-yl)acrylic Acid To a mixture of 8-bromo-9-(4-fluorobenzyl)-1,3-dimethyl-3,9-dihydro-1H-purine-2,6-dione (200 mg), ethyl (2E)-3-(4,4,5,5-tetramethyl-1,3,2-dioxaborolan-2-yl)acrylate (185 mg), palladium(II) acetate (12.2 mg), triphenylphosphine-3,3',3"-trisulfonic acid trisodium salt hydrate (63.9 mg) and acetonitrile (3 mL), a solution of potassium carbonate (151 mg) in water (1.5 mL) was added at room temperature, and the mixture was heated at 100° C. for 14 hours in a nitrogen atmosphere. Water and ethyl acetate were added to the mixture, and the aqueous layer was separated. The pH of the aqueous layer was adjusted to 3 with 6 N hydrochloric acid, followed by extraction with a mixed solution of ethyl acetate and THF. The organic layer was washed with saturated saline, then dried over anhydrous sodium sulfate, and concentrated under reduced pressure. The resulting crystals were washed with ethyl acetate and then collected by filtration to obtain the title compound (160 mg).

MS: [M+H]$^+$ 359.1.

B

To a mixture of (2E)-3-(9-(4-fluorobenzyl)-1,3-dimethyl-2,6-dioxo-2,3,6,9-tetrahydro-1H-purin-8-yl)acrylic acid (30.0 mg), N-(2-(2-(2-(2-aminoethoxy)ethoxy)ethyl)-2-((6S)-4-(4-chlorophenyl)-2,3,9-trimethyl-6H-thieno[3,2-f][1,2,4]triazolo[4,3-a][1,4]diazepin-6-yl)acetamide hydrochloride (61.4 mg), HOBt·H$_2$O (16.7 mg) and DMF (1 mL), WSC·HCl (20.9 mg) and DIPEA (0.044 mL) were added at room temperature, and the mixture was stirred at room temperature for 8 hours in a nitrogen atmosphere. The mixture was concentrated under reduced pressure. Then, a saturated aqueous solution of sodium bicarbonate and water were added to the residue, and the mixture was subjected to extraction with ethyl acetate. The organic layer was separated, washed with saturated saline, then dried over anhydrous sodium sulfate, and concentrated under reduced pressure. The obtained residue was purified by HPLC (L-Column 2 ODS, mobile phase: water/acetonitrile (system containing 0.1% TFA)). The obtained fraction was passed through MP-Carbonate resin and concentrated under reduced pressure to obtain the title compound (61.2 mg).

$^1$H NMR (300 MHz, DMSO-$d_6$) δ 1.62 (3H, s), 2.40 (3H, s), 2.59 (3H, s), 3.12-3.72 (24H, m), 4.51 (1H, t, J=6.9 Hz), 5.75 (2H, s), 7.09-7.31 (5H, m), 7.35-7.55 (5H, m), 8.28 (1H, t, J=5.1 Hz), 8.55 (1H, t, J=5.2 Hz).

Example 55

(2E)-N-(21-Chloro-3,6,9,12,15-pentaoxahenicos-1-yl)-3-(9-(4-fluorobenzyl)-1,3-dimethyl-2,6-dioxo-2,3,6,9-tetrahydro-1H-purin-8-yl)acrylamide To a mixture of (2E)-3-(9-(4-fluorobenzyl)-1,3-dimethyl-2,6-dioxo-2,3,6,9-tetrahydro-1H-purin-8-yl)acrylic acid (40.0 mg), 21-chloro-3,6,9,12,15-pentaoxahenicosan-1-amine hydrochloride (52.6 mg), HOBt·H$_2$O (22.2 mg) and DMF (1 mL), WSC·HCl (27.8 mg) and DIPEA (0.058 mL) were added at room temperature, and the mixture was stirred at room temperature for 8 hours in a nitrogen atmosphere. The mixture was concentrated under reduced pressure. Then, a saturated aqueous solution of sodium bicarbonate and water were added to the residue, and the mixture was subjected to extraction with ethyl acetate. The organic layer was separated, washed with saturated saline, then dried over anhydrous sodium sulfate, and concentrated under reduced pressure. The residue was purified by HPLC (L-Column 2 ODS, mobile phase: water/acetonitrile (system containing 0.1% TFA)) and then crystallized from MeOH/IPE to obtain the title compound (52.0 mg).

$^1$H NMR (300 MHz, DMSO-$d_6$) δ 1.17-1.56 (6H, m), 1.69 (2H, quin, J=7.0 Hz), 3.12-3.67 (30H, m), 5.76 (2H, s), 7.10-7.31 (5H, m), 7.43 (1H, d, J=15.1 Hz), 8.55 (1H, t, J=5.6 Hz).

Example 56

N$^2$-Acetyl-S-(2-amino-9-(4-fluorobenzyl)-6-oxo-6,9-dihydro-1H-purin-8-yl)-N-(21-chloro-3,6,9,12,15-pentaoxahenicos-1-yl)-L-cysteinamide N-Acetyl-S-(2-amino-9-(4-fluorobenzyl)-6-oxo-6,9-dihydro-1H-purin-8-yl)-L-cysteine (5.0 mg) and 21-chloro-3,6,9,12,15-pentaoxahenicosan-1-amine (6.8 mg) were dissolved in dehydrated DMF (500 uL). To the solution, WSC·HCl (1.8 mg), TEA (1.4 uL) and HOBt (2.1 mg) were added at room temperature. After stirring at room temperature for 24 hours, the reaction mixture was concentrated under reduced pressure. The residue was purified by HPLC (5C18-AR-II, mobile phase: water/acetonitrile (system containing 0.1% TFA)) to obtain the title compound (1.5 mg).

$^1$H NMR (600 MHz, DMSO-$d_6$) δ 1.33-1.71 (8H, m), 1.83 (3H, s), 3.45-3.50 (22H, m), 3.60 (2H, t, J=6.7 Hz), 4.47 (1H, ddd, J=13.2, 8.0, 5.0 Hz), 5.06 (2H, brs), 6.52 (2H, brs), 7.12-7.21 (4H, m), 8.06 (1H, t, J=5.4 Hz), 8.39 (1H, d, J=8.4 Hz), 10.63 (1H, brs).

Example 57

N$^2$-Acetyl-S-(2-amino-9-(4-fluorobenzyl)-6-oxo-6,9-dihydro-1H-purin-8-yl)-N-(1-((6S)-4-(4-chlorophenyl)-2,3,9-trimethyl-6H-thieno[3,2-f][1,2,4]triazolo[4,3-a][1,4]diazepin-6-yl)-2-oxo-7,10,13-trioxa-3-azahexadecan-16-yl)-L-cysteinamide A) N-(3-(2-(2-(3-Aminopropoxy)ethoxy)ethoxy)propyl)-2-((6S)-4-(4-chlorophenyl)-2,3,9-trimethyl-6H-thieno[3,2-f][1,2,4]triazolo[4,3-a][1,4]diazepin-6-yeacetamide To ((6S)-4-(4-chlorophenyl)-2,3,9-trimethyl-6H-thieno[3,2-f][1,2,4]triazolo[4,3-a][1,4]diazepin-6-yl)acetic acid (7.5 mg), DMF (0.2 mL), 4,7,10-trioxa-1,13-tridecanediamine (7.9 uL), PyBOP (20 mg) and TEA (5.2 uL) were added at room temperature in an argon atmosphere, and the mixture was warmed to 40° C. After stirring for 18 hours, the reaction mixture was purified by HPLC (5C18-AR-II, mobile phase: water/acetonitrile (system containing 0.1% TFA)) to obtain the title compound (9.0 mg).

The ((6S)-4-(4-chlorophenyl)-2,3,9-trimethyl-6H-thieno[3,2-f][1,2,4]triazolo[4,3-a][1,4]diazepin-6-yl)acetic acid used was a compound synthesized according to a method known per se in the art (e.g., a method described in Nature, 2010, 468, 1067-1073). A compound synthesized in the same way as above was also used in Examples 58 and 61.

HRMS: Calcd for $C_{29}H_{40}ClN_6O_4S$ [M+H]$^+$: 603.2520, found 603.2511.

B) N$^2$-Acetyl-S-(2-amino-9-(4-fluorobenzyl)-6-oxo-6,9-dihydro-1H-purin-8-yl)-N-(1-((6S)-4-(4-chlorophenyl)-2,3,9-trimethyl-6H-thieno[3,2-f][1,2,4]triazolo[4,3-a][1,4]diazepin-6-yl)-2-oxo-7,10,13-trioxa-3-azahexadecan-16-yl)-L-cysteinamide To a mixture of N-(3-(2-(2-(3-aminopropoxy)ethoxy)ethoxy)propyl)-2-((6S)-4-(4-chlorophenyl)-2,3,9-trimethyl-6H-thieno[3,2-f][1,2,4]triazolo[4,3-a][1,4]diazepin-6-yeacetamide (13 mg) and N-acetyl-S-(2-amino-9-(4-fluorobenzyl)-6-oxo-6,9-dihydro-1H-purin-8-yl)-L-cysteine (8.0 mg), DMF (50 uL), PyBOP (14 mg), and TEA (3.8 uL) were added at room temperature, and the mixture was stirred for 27 hours. The reaction mixture was purified by HPLC (5C18-AR-II, mobile phase: water/acetonitrile (system containing 0.1% TFA)) to obtain the title compound (1.0 mg).

$^1$H NMR (600 MHz, DMSO-$d_6$) δ 1.59 (2H, quin, J=6.9 Hz), 1.61 (3H, s), 1.65 (2H, quin, J=6.4 Hz), 1.83 (3H, s), 2.39 (3H, s), 2.58 (3H, s), 3.06-3.28 (12H, m), 3.33-3.35 (6H, m), 4.43 (1H, ddd, J=13.3, 7.8, 5.2 Hz), 4.49 (1H, dd, J=8.3, 6.4 Hz), 5.06 (2H, s), 6.52 (2H, s), 7.14 (2H, dd, J=8.7, 8.7 Hz), 7.19 (2H, dd, J=14.4, 8.7 Hz), 7.40 (2H, d, J=9.1 Hz), 7.47 (2H, d, J=9.1 Hz), 8.01 (1H, t, J=5.5 Hz), 8.18 (1H, t, J=5.7 Hz), 8.40 (1H, d, J=8.2 Hz), 10.63 (1H, s).

Example 58

N-(3-(2-(2-(3-((2-Amino-9-(4-fluorobenzyl)-6-oxo-6,9-dihydro-1H-purin-8-yl)amino)propoxy)ethoxy)ethoxy)propyl)-2-((6S)-4-(4-chlorophenyl)-2,3,9-trimethyl-6H-thieno[3,2-f][1,2,4]triazolo[4,3-a][1,4]diazepin-6-yl)acetamide A) 2-Amino-8-((3-(2-(2-(3-aminopropoxy)ethoxy)ethoxy)propyl)amino)-9-(4-fluorobenzyl)-1,9-dihydro-6H-purin-6-one 2-Amino-8-bromo-9-(4-fluorobenzyl)-1,9-dihydro-6H-purin-6-one (10 mg), DMSO (0.18 mL), 4,7,10-trioxa-1,13- tridecanediamine (33 uL) and TEA (21 uL) were plated in a test tube with a screw in an argon atmosphere, and the test tube was sealed. The test tube was warmed to 110° C., stirred for 19 hours, and then cooled to room temperature. The reaction mixture was purified by HPLC (5C18-AR-II, mobile phase: water/acetonitrile (system containing 0.1% TFA)) to obtain the title compound (3.7 mg).

HRMS: Calcd for $C_{22}H_{33}FN_7O_4$: 478.2578 [M+H]$^+$, found 478.2562.

B) N-(3-(2-(2-(3-((2-Amino-9-(4-fluorobenzyl)-6-oxo-6,9-dihydro-1H-purin-8-yl)amino)propoxy)ethoxy)ethoxy)propyl)-2-(4-(4-chlorophenyl)-2,3,9-trimethyl-6H-thieno[3,2-f][1,2,4]triazolo[4,3-a][1,4]diazepin-6-yeacetamide To a mixture of 2-amino-8-((3-(2-(2-(3-aminopropoxy)ethoxy)ethoxy)propyl)amino)-9-(4-fluorobenzyl)-1,9-dihydro-6H-purin-6-one (2.4 mg) and (4-(4-chlorophenyl)-2,3,9-trimethyl-6H-thieno[3,2-f][1,2,4]triazolo[4,3-a][1,4]diazepin-6-yl)acetic acid (3.6 mg), DMF (0.1 mL), PyBOP (5.3 mg) and TEA (1.4 uL) were added at room temperature in an argon atmosphere, and the mixture was stirred for 31 hours. The reaction mixture was purified by HPLC (5C18-AR-II, mobile phase: water/acetonitrile (system containing 0.1% TFA)) to obtain the title compound (0.26 mg).

$^1$H NMR (600 MHz, DMSO-d$_6$) δ 1.60 (3H, s), 1.65 (2H, quin, J=6.9 Hz), 1.74 (1H, dd, J=4.6, 4.6 Hz), 1.89 (1H, s), 2.39 (3H, s), 2.58 (3H, s), 3.10-3.22 (10H, m), 3.36-3.51 (6H, m), 4.46-4.50 (2H, m), 5.11 (2H, d, J=8.7 Hz), 7.18 (2H, dd, J=8.8, 8.7 Hz), 7.30 (2H, dd, J=8.7, 5.0 Hz), 7.39-7.42 (4H, m), 7.46-7.50 (4H, m), 8.18 (2H, t, J=5.8 Hz).

Example 59

(1R)-1-(3-((18-((N-Acetyl-S-(2-amino-9-(4-fluorobenzyl)-6-oxo-6,9-dihydro-1H-purin-8-yl)-L-cysteinyl)amino)-4-oxo-9,12,15-trioxa-5-azaoctadecan-1-oyl)amino)phenyl)-3-(3,4-dimethoxyphenyl)propyl 1-(3,3-dimethyl-2-oxopentanoyl)piperidine-2-carboxylate A) N$^2$-Acetyl-S-(2-amino-9-(4-fluorobenzyl)-6-oxo-6,9-dihydro-1H-purin-8-yl)-N-(3-(2-(2-(3-aminopropoxy)ethoxy)propyl)-L-cysteinamide A mixture of N-acetyl-S-(2-amino-9-(4-fluorobenzyl)-6-oxo-6,9-dihydro-1H-purin-8-yl)-L-cysteine (35 mg), DMF (1.0 mL), 4,7,10-trioxa-1,13-tridecanediamine (0.037 mL), PyBOP (66 mg) and TEA (0.023 mL) was stirred at room temperature for 22 hours in an argon atmosphere. The reaction mixture was purified by HPLC (5C18-AR-II, mobile phase: water/acetonitrile (system containing 0.1% TFA)) to obtain the title compound (24 mg).

HRMS: Calcd for $C_{27}H_{40}FN_8O_6S$ [M+H]$^+$: 623.2776, found 623.2753.

B) (1R)-1-(3-((18-((N-Acetyl-S-(2-amino-9-(4-fluorobenzyl)-6-oxo-6,9-dihydro-1H-purin-8-yl)-L-cysteinyl)amino)-4-oxo-9,12,15-trioxa-5-azaoctadecan-1-oyl)amino)phenyl)-3-(3,4-dimethoxyphenyl)propyl 1-(3,3-dimethyl-2-oxopentanoyl)piperidine-2-carboxylate To a mixture of N$^2$-acetyl-S-(2-amino-9-(4-fluorobenzyl)-6-oxo-6,9-dihydro-1H-purin-8-yl)-N-(3-(2-(2-(3-aminopropoxy)ethoxy)ethoxy)propyl)-L-cysteinamide (2.5 mg) and 4-((3-((1R)-3-(3,4-dimethoxyphenyl)-1-(((1-(3,3-dimethyl-2-oxopentanoyl)piperidin-2-yl)carbonyl)oxy)propyl)phenyl)amino)-4-oxobutanoic acid (2.5 mg), DMF (0.2 mL), PyBOP (2.2 mg) and TEA (0.010 mL) were added. After stirring at room temperature for 24 hours, the reaction mixture was purified by silica gel column chromatography (MeOH/chloroform) to obtain the title compound (0.16 mg).

The 4-((3-((1R)-3-(3,4-dimethoxyphenyl)-1-(((1-(3,3-dimethyl-2-oxopentanoyl)piperidin-2-yl)carbonyl)oxy)propyl)phenyl)amino)-4-oxobutanoic acid used was a compound synthesized according to a method known per se in the art (e.g., a method described in ACS Chemical Biology, 2015, 10, 2441-2447).

$^1$H NMR (600 MHz, DMSO-d$_6$) δ 0.78 (3H, s), 1.13 (3H, s), 1.15 (3H, s), 1.57-1.70 (14H, m), 1.89 (3H, s), 2.49-2.55 (6H, m), 3.04-3.08 (4H, m), 3.37-3.47 (16H, m), 3.69 (3H, s), 3.71 (3H, s), 4.43 (1H, dd, J=14.2, 8.7 Hz), 5.06 (1H, s), 5.12 (1H, dd, J=6.4, 6.4 Hz), 5.61 (1H, dd, J=9.1, 5.0 Hz), 6.66 (1H, d, J=8.3 Hz), 6.75 (1H, d, J=1.8 Hz), 6.83 (1H, d, J=8.2 Hz), 6.99 (1H, d, J=9.2 Hz), 7.14 (2H, dd, J=8.7, 8.7 Hz), 7.19 (2H, dd, J=8.7, 8.7 Hz), 7.27 (2H, dd, J=8.3, 8.3 Hz), 7.43 (1H, d, J=7.3 Hz), 7.68 (1H, s), 7.84 (1H, d, J=5.5 Hz), 8.03 (1H, dd, J=5.5, 5.5 Hz), 8.42 (1H, d, J=8.3 Hz), 9.89 (1H, s), 10.87 (1H, brs).

Example 60

(3R,5S,6R)-5-Methoxy-4-((2R,3R)-2-methyl-3-(3-methylbut-2-en-1-yl)oxiran-2-yl)-1-oxaspiro[2.5]oct-6-yl (3-(2-(2-(3-((N-acetyl-S-(2-amino-9-(4-fluorobenzyl)-6-oxo-6,9-dihydro-1H-purin-8-yl)-L-cysteinyl)amino)propoxy)ethoxy)ethoxy)propyl)carbamate To a solution of fumagillol (5.0 mg) in acetonitrile (37.5 uL), TEA (7.3 uL) and p-nitrophenyl chloroformate (7.2 mg) were added at 0° C. in an argon atmosphere, and the mixture was stirred overnight. The reaction mixture was concentrated under reduced pressure and purified by silica gel column chromatography (ethyl acetate/hexane). This intermediate and N$^2$-acetyl-S-(2-amino-9-(4-fluorobenzyl)-6-oxo-6,9-dihydro-1H-purin-8-yl)-N-(3-(2-(2-(3-aminopropoxy)ethoxy)ethoxy)propyl)-L-cysteinamide (6.6 mg) were dissolved in MeOH (25 uL) in an argon atmosphere. To the solution, sodium bicarbonate (7.2 mg) was added at 0° C. Then, the mixture was warmed to room temperature and stirred overnight. The reaction mixture was purified by HPLC (5C18-AR-II, mobile phase: water/acetonitrile (system containing 0.1% TFA)) to obtain the title compound (0.34 mg).

$^1$H NMR (600 MHz, DMSO-d$_6$) δ 1.07 (3H, s), 1.59 (3H, s), 1.57-1.63 (3H, m), 1.81 (1H, d, J=11.0 Hz), 1.83 (3H, s), 1.76-1.89 (6H, m), 2.13-2.19 (2H, m), 2.55 (1H, d, J=4.6

Hz), 2.60 (1H, dd, J=3.7, 1.9 Hz), 2.82 (1H, d, J=4.6 Hz), 3.01 (2H, dt, J=7.4, 6.4 Hz), 3.06 (2H, dt, J=9.7, 6.8), 3.26 (3H, s), 3.26 (3H, s), 3.30-3.49 (14H, m), 4.43 (1H, ddd, J=13.7, 7.8, 5.5 Hz), 5.06 (2H, s), 5.17 (1H, t, J=7.4 Hz), 5.27 (1 h, brs), 6.54 (2H, brs), 7.04 (1H, t, J=6.0 Hz), 7.12-7.25 (4H, m), 8.02 (1H, t, J=5.5 Hz), 8.41 (1H, d, J=7.8 Hz).

Example 61

$N^2$-Acetyl-S-(2-amino-9-((4aR,6R,7R,7aS)-2,7-dihydroxy-2-oxidotetrahydro-4H-furo[3,2-d][1,3,2]dioxaphosphinin-6-yl)-6-oxo-6,9-dihydro-1H-purin-8-yl)-N-(1-((6S)-4-(4-chlorophenyl)-2,3,9-trimethyl-6H-thieno[3,2-f][1,2,4]triazolo[4,3-a][1,4]diazepin-6-yl)-2-oxo-7,10,13-trioxa-3-azahexadecan-16-yl)-L-cysteinamide A) N-Acetyl-S-(2-amino-9-(2,7-dihydroxy-2-oxidotetrahydro-4H-furo[3,2-d][1,3,2]dioxaphosphinin-6-yl)-6-oxo-6,9-dihydro-1H-purin-8-yl)-L-cysteine 8-Bromoguanosine-3',5'-phosphoric acid (8.5 mg), potassium carbonate (31.5 mg) and N-acetyl-L-cysteine (12.4 mg) were dissolved in DMF (0.5 mL) in an argon atmosphere. The reaction solution was stirred at 90° C. for 5 hours. After cooling to room temperature, the reaction mixture was purified by HPLC (5C18-AR-II, mobile phase: water/acetonitrile (system containing 0.1% TFA)) to obtain the title compound (9.4 mg).

HRMS: Calcd for $C_{15}H_{18}N_6O_{10}PS$: 505.0548, found 505.0546.

B) $N^2$-Acetyl-S-(2-amino-9-(2,7-dihydroxy-2-oxidotetrahydro-4H-furo[3,2-d][1,3,2]dioxaphosphinin-6-yl)-6-oxo-6,9-dihydro-1H-purin-8-yl)-N-(1-((6S)-4-(4-chlorophenyl)-2,3,9-trimethyl-6H-thieno[3,2-f][1,2,4]triazolo[4,3-a][1,4]diazepin-6-yl)-2-oxo-7,10,13-trioxa-3-azahexadecan-16-yl)-L-cysteinamide To a mixture of N-(3-(2-(2-(3-aminopropoxy)ethoxy)ethoxy)propyl)-2-((6S)-4-(4-chlorophenyl)-2,3,9-trimethyl-6H-thieno[3,2-f][1,2,4]triazolo[4,3-a][1,4]diazepin-6-yeacetamide (9.0 mg) and N-acetyl-S-(2-amino-9-(2,7-dihydroxy-2-oxidotetrahydro-4H-furo[3,2-d][1,3,2]dioxaphosphinin-6-yl)-6-oxo-6,9-dihydro-1H-purin-8-yl)-L-cysteine (8.4 mg), DMF (0.25 mL), HATU (9.4 mg), and TEA (23.1 uL) were added at room temperature, and the mixture was stirred for 38 hours. The reaction mixture was purified by HPLC (5C18-AR-II, mobile phase: water/acetonitrile (system containing 0.1% TFA)) to obtain the title compound (3.2 mg).

$^1$H NMR (600 MHz, DMSO-$d_6$) δ 1.61 (3H, s), 1.65 (2H, quin, J=6.4), 1.85 (3H, s), 2.40 (3H, s), 2.59 (3H, s), 3.08-3.28 (6H, m), 3.35-3.54 (14H, m), 4.05 (1H, ddd, J=15.1, 10.1, 4.1 Hz), 4.16 (1H, dd, J=10.1, 10.1 Hz), 4.72 (1H, d, J=5.5 Hz), 4.45-4.51 (4H, m), 4.94 (1H, dd, J=9.7, 5.4 Hz), 5.70 (1H, s), 6.45 (2H, brs), 7.41 (2H, t, J=8.2 Hz), 7.48 (2H, d, J=8.7 Hz), 8.01 (1H, t, J=5.5 Hz), 8.19 (1H, t, J=5.5 Hz), 8.35 (1H, d, J=8.3 Hz), 10.81 (1H, s).

The compounds of Examples are shown below in the tables. MS in the tables represent a found value. The compounds of Examples 4, 7, 9, 11, 14, 22 to 25, 28, 29, and 36 to 43 shown below in the tables were produced according to the methods shown above in Examples or methods equivalent thereto.

TABLE 1-1

| Example No. | IUPAC name | Structural formula | Salt | MS |
|---|---|---|---|---|
| 1 | $N^2$-acetyl-S-(2-amino-9-(4-chlorobenzyl)-6-oxo-6,9-dihydro-1H-purin-8-yl)-N-(21-chloro-3,6,9,12,15-pentaoxahenicos-1-yl)-L-cysteinamide | | | 774.4 |
| 2 | 3-((2-amino-9-(4-fluorobenzyl)-6-oxo-6,9-dihydro-1H-purin-8-yl)sulfanyl)-N-(21-chloro-3,6,9,12,15-pentaoxahenicos-1-yl)propanamide | | | 701.4 |

TABLE 1-1-continued

| Example No. | IUPAC name | Structural formula | Salt | MS |
|---|---|---|---|---|
| 3 | 4-(2-amino-9-(4-fluorobenzyl)-6-oxo-6,9-dihydro-1H-purin-8-yl)-N-(21-chloro-3,6,9,12,15-pentaoxahenicos-1-yl)benzamide | | | 717.4 |
| 4 | 3-(2-amino-9-(4-fluorobenzyl)-6-oxo-6,9-dihydro-1H-purin-8-yl)-N-(21-chloro-3,6,9,12,15-pentnoxahenicos-1-yl)benzamide | | | 717.4 |

TABLE 1-2

| Example No. | IUPAC name | Structural formula | Salt | MS |
|---|---|---|---|---|
| 5 | (2E)-3-(2-amino-9-(4-fluorobenzyl)-6-oxo-6,9-dihydro-1H-purin-8-yl)-N-(21-chloro-3,6,9,12,15-pentaoxahenicos-1-yl)actylamide | | | 667.3 |
| 6 | 3-(2-amino-9-(4-fluorobenzyl)-6-oxo-6,9-dihydro-1H-purin-8-yl)-N-(21-chloro-3,6,9,12,15-pentaoxahenicos-1-yl)propanamide | | | 669.4 |

TABLE 1-2-continued

| Example No. | IUPAC name | Structural formula | Salt | MS |
|---|---|---|---|---|
| 7 | 2-(2-amino-9-(4-fluorobenzyl)-6-oxo-6,9-dihydro-1H-purin-8-yl)sulfanyl)-N-(21-chloro-3,6,9,12,15-pentaoxahenicos-1-yl)acetamide | | | 687.3 |
| 8 | N³-(2-amino-9-(4-fluorobenzyl)-6-oxo-6,9-dihydro-1H-purin-8-yl)-N-(21-chloro-3,6,9,12,15-pentaoxahenicos-1-yl)-β-alaninamide | | | 684.3 |

TABLE 1-3

| Example No. | IUPAC name | Structural formula | Salt | MS |
|---|---|---|---|---|
| 9 | N²-(2-amino-9-(4-fluorobenzyl)-6-oxo-6,9-dihydro-1H-purin-8-yl)-N-(21-chloro-3,6,9,12,15-pentaoxahenicos-1-yl)glycinamide | | | 670.4 |
| 10 | 2-amino-8-(3-((21-chloro-3,6,9,12,15-pentaoxahenicos-1-yl)oxy)phenyl)-9-(4-fluorobenzyl)-1,9-dihydro-6H-purin-6-one | | | 690.3 |

TABLE 1-3-continued

| Example No. | IUPAC name | Structural formula | Salt | MS |
|---|---|---|---|---|
| 11 | 2-amino-8-(4-((21-chloro-3,6,9,12,15-pentaoxahenicos-1-yl)oxy)phenyl)-9-(4-fluorobenzyl)-1,9-dihydro-6H-purin-6-enea | | | 690.3 |
| 12 | $N^2$-acetyl-S-(2-amino-9-cyclopentyl-6-oxo-6,9-dihydro-1H-purin-8-yl)-N-(21-chloro-3,6,9,12,15-pentaoxahenicos-1-yl)-L-cysteinamide | | | 718.4 |

TABLE 1-4

| Example No. | IUPAC name | Structural formula | Salt | MS |
|---|---|---|---|---|
| 13 | $N^2$-acetyl-N-(21-chloro-3,6,9,12,15-pentaoxahenicos-1-yl)-S-(9-(4-fluorobenzyl)-1,3-dimethyl-2,6-dioxo-2,3,6,9-tetrahydro-1H-purin-8-yl)-L-cysteinamide | | | 787.3 |
| 14 | 2-amino-8-(1-(21-chloro-3,6,9,12,15-pentaoxahenicos-1-yl)-1H-pyrazol-4-yl)-9-(4-fluorobenzyl)-1,9-dihydro-6H-purin-6-one | | | 664.2 |
| 15 | 2-amino-8-(1-(21-chloro-3,6,9,12,15-pentaoxahenicos-1-yl)-1H-1,2,3-triazole-4-yl)-9-(4-fluotobenzyl)-1,9-dihydro-6H-purin-6-one | | | 665.3 |

TABLE 1-4-continued

| Example No. | IUPAC name | Structural formula | Salt | MS |
|---|---|---|---|---|
| 16 | 2-amino-8-(25-chloro-4,7,10,13,16,19-hexaoxapentacos-1-yn-1-yl)-9-(4-fluorobenzyl)-1,9-dihydro-6H-purin-6-one | | | 652.3 |

TABLE 1-5

| Example No. | IUPAC name | Structural formula | Salt | MS |
|---|---|---|---|---|
| 17 | $N^2$-acetyl-S-(6-amino-9-(4-fluorobenzyl)-9H-purin-8-yl)-N-(21-chloro-3,6,9,12,15-pentaoxahenicos-1-yl)-L-cysteinamide trifluoroacetic acid salt | | CF3COOH | 742.3 |
| 18 | $N^2$-acetyl-N-(21-chloro-3,6,9,12,15-pentaoxahenicos-1-yl)-S-(9-(4-fluorobenzyl)-9H-purin-8-yl)-L-cysteinamide | | | 727.3 |

TABLE 1-5-continued

| Example No. | IUPAC name | Structural formula | Salt | MS |
|---|---|---|---|---|
| 19 | $N^2$-acetyl-S-(2-amino-4-((4-fluorobenzyl)amino)-6-oxo-1,6-dihydropyrimidin-5-yl)-N-(21-chloro-3,6,9,11,15-pentaoxahenicos-1-yl)-L-cysteinamide trifluoroacetic acid salt | | CF3COOH | 733.3 |
| 20 | $N^3$-acetyl-S-(2-amino-9-benzyl-6-oxo-6,9-dihydro-1H-purin-8-yl)-N-(21-chloro-3,6,9,12,15-pentaoxahenicos-1-yl)-L-cysteinamide trifluoroacetic acid salt | | CF3COOH | 740.3 |

TABLE 1-6

| Example No. | IUPAC name | Structural formula | Salt | MS |
|---|---|---|---|---|
| 21 | N²-acetyl-S-(4-amino-1-(4-fluorobenzyl)-2-oxo-1,2-dihydropyrimidin-5-yl)-N-(21-chloro-3,6,9,12,15-pentaoxahenicos-1-yl)-L-cysteinamide trifluoroacetic acid salt | | CF3COOH | 718.3 |
| 22 | N²-acetyl-S-(2-amino-9-(2-fluorobonzyl)-6-oxo-6,9-dihydro-1H-purin-8-yl)-N-(21-chloro-3,6,9,12,15-pentaoxahenicos-1-yl)-L-cysteinamide | | | 758.3 |
| 23 | N²-acetyl-S-(2-amino-9-(3-(fluorobenzyl)-6-oxo-6,9-dihydro-1H-purln-8-yl)-N-(21-chloro-3,6,9,12,15-pentaoxahenicos-1-yl)-L-cysteinamide | | | 756.3 |
| 24 | N²-acetyl-S-(2-amino-9-(2-chlorobenzyl)-6-oxo-6,9-dihydro-1H-purin-8-yl)-N-(21-chloro-3,6,9,12,15-pentaoxahenicos-1-yl)-L-cysteinamide | | | 774.3 |

TABLE 1-7

| Example No. | IUPAC name | Structural formula | Salt | MS |
|---|---|---|---|---|
| 25 | N²-acetyl-S-(2-amino-9-(4-methylbenzyl)-6-oxo-6,9-dihydro-1H-purin-8-yl)-N-(21-chloro-3,6,9,12,15-pentaoxahenicos-1-yl)-L-cysteinamide | | | 752.3 |
| 26 | N²-acetyl-N-(21-chloro-3,6,9,12,15-pentaoxahenicos-1-yl)-S-(9-(4-fluorobenzyl)-6-oxo-6,9-dihydro-1H-purin-8-yl)-L-cysteinamide | | | 743.1 |

TABLE 1-7-continued

| Example No. | IUPAC name | Structural formula | Salt | MS |
|---|---|---|---|---|
| 27 | S-(2-acetamide-9-(4-fluorobenzyl)-6-oxo-6,9-dihydro-1H-purin-8-yl)-N²-acetyl-N-(21-chloro-3,6,9,12,15-pentaoxahenicos-1-yl)-L-cysteinamide | | | 800.1 |
| 28 | N²-acetyl-S-(2-amino-9-cyclohexyl-6-oxo-6,9-dihydro-1H-purin-8-yl)-N-(21-chloro-3,6,9,12,15-pentaoxahenicos-1-yl)-L-cysteinamide | | | 732.4 |

TABLE 1-8

| Example No. | IUPAC name | Structural formula | Salt | MS |
|---|---|---|---|---|
| 29 | N²-acetyl-S-(2-amino-6-oxo-9-(tetrahydro-2H-pyran-4-yl methyl)-6,9-dihydro-1H-purin-8-yl)-N-(21-chloro-3,6,9,12,15-pentaoxa-henicos-1-yl)-L-cysteinamide | | | 748.3 |
| 30 | N²-acetyl-S-(2-amino-9-(4-fluoro-benzyl)-1-methyl-6-oxo-6,9-dihydro-1H-purin-8-yl)-N-(21-chloro-3,6,9,12,15-pentaoxa-henicos-1-yl)-L-cysteinamide | | | 772.3 |
| 31 | 2-amino-8-(25-chloro-4,7,10,13,16,19-hexa-oxapentacos-1-yl)-9-(4-fluoro-benzyl)-1,9-dihydro-6H-purin-6-one | | | 656.3 |
| 32 | 2-amino-8-(23-chloro-5,8,11,14,17-pentaoxa-2-azatricos-1-yl)-9-(4-fluoro-benzyl)-1,9-dihydro-6H-purin-6-one | | | 627.3 |

TABLE 1-9

| Example No. | IUPAC name | Structural formula | Salt | MS |
|---|---|---|---|---|
| 33 | 2-amino-N-(21-chloro-3,6,9,12,15-pentaoxa-henicos-1-yl)-9-(4-fluoro-benzyl)-6-oxo-6,9-dihydro-1H-purine-8-carboxamide | | | 641.3 |
| 34 | N²-acetyl-N-(21-chloro-3,6,9,12,15-pentaoxa-henicos-1-yl)-S-(9-(4-fluoro-benzyl)-2,6-dioxo-2,3,6,9-tetrahydro-1H-purin-8-yl)-L-cysteinamide | | | 759.3 |
| 35 | N²-acetyl-N-(21-chloro-3,6,9,12,15-pentaoxa-henicos-1-yl)-S-(9-(4-fluoro-benzyl)-1-methyl-2,6-dioxo-2,3,6,9-tetrahydro-1H-purin-8-yl)-L-cysteinamide | | | 773.3 |
| 36 | N²-acetyl-S-(2-amino-9-(4-cyano-benzyl)-6-oxo-6,9-dihydro-1H-purin-8-yl)-N-(21-chloro-3,6,9,12,15-pentaoxa-henicos-1-yl)-L-cysteinamide | | | 765.3 |

TABLE 1-10

| Example No. | IUPAC name | Structural formula | Salt | MS |
|---|---|---|---|---|
| 37 | N²-acetyl-S-(2-amino-9-(3-chloro-benzyl)-6-oxo-6,9-dihydro-1H-purin-8-yl)-N-(21-chloro-3,6,9,12,15-pentaoxa-henicos-1-yl)-L-cysteinamide | | | 774.2 |
| 38 | N²-acetyl-S-(2-amino-9-(4-methoxy-benzyl)-6-oxo-6,9-dihydro-1H-purin-8-yl)-N-(21-chloro-3,6,9,12,15-pentaoxa-henicos-1-yl)-L-cysteinamide | | | 770.3 |
| 39 | N²-acetyl-S-(2-amino-9-(4-(methyl sulfonyl)benzyl)-6-oxo-6,9-dihydro-1H-purin-8-yl)-N-(21-chloro-3,6,9,12,15-pentaoxa-henicos-1-yl)-L-cysteinamide | | | 818.3 |
| 40 | N²-acetyl-S-(2-amino-6-oxo-9-phenyl-6,9-dihydro-1H-purin-8-yl)-N-(21-chloro-3,6,9,12,15-pentaoxa-henicos-1-yl)-L-cysteinamide | | | 726.3 |

TABLE 1-11

| Example No. | IUPAC name | Structural formula | Salt | MS |
|---|---|---|---|---|
| 41 | $N^2$-acetyl-S-(2-amino-6-oxo-9-(pyridin-3-ylmethyl)-6,9-dihydro-1H-purin-8-yl)-N-(21-chloro-3,6,9,12,15-pentaoxahenicos-1-yl)-L-cysteinamide trifluoroacetic acid salt | | CF3COOH | 726.2 |
| 42 | $N^2$-acetyl-S-(2-amino-6-oxo-9-(1,3-thiazole-5-ylmethyl)-6,9-dihydro-1H-purin-8-yl)-N-(21-chloro-3,6,9,12,15-pentaoxahenicos-1-yl)-L-cysteinamide | | | 747.2 |
| 43 | $N^2$-acetyl-S-(2-amino-9-((1-methyl-1H-pyrazole-4-yl)methyl)-6-oxo-6,9-dihydro-1H-purin-8-yl)-N-(21-chloro-3,6,9,12,15-pentaoxahenicos-1-yl)-L-cysteinamide | | | 744.2 |
| 44 | $N^2$-acetyl-N-(21-chloro-3,6,9,12,15-pentaoxahenicos-1-yl)-S-(3-(4-fluorobenzyl)-9-oxo-5,9-dihydro-3H-imidazo[1,2-a]purin-2-yl)-L-cysteinamide | | | 782.3 |

TABLE 1-12

| Example No. | IUPAC name | Structural formula | Salt | MS |
|---|---|---|---|---|
| 45 | N²-acetyl-N-(21-chloro-3,6,9,12,15-pentaoxa-henicos-1-yl)-S-(2,6-diamino-9-(4-fluoro-benzyl)-9H-purin-8-yl)-L-cysteinamide | | | 757.3 |
| 46 | 1-((2-amino-9-(4-fluoro-benzyl)-6-oxo-6,9-dihydro-1H-purin-8-yl)carbonyl)-N-(21-chloro-3,6,9,12,15-pentaoxa-henicos-1-yl)piperidine-2-carboxamide | | | 752.3 |
| 47 | 2-amino-N-(14-((6S)-4-(4-chloro-phenyl)-2,3,9-trimethyl-6H-thieno[3,2-f][1,2,4]triazolo[4,3-a][1,4]diazepin-6-yl)-13-oxa-3,6,9-trioxa-12-azatetradec-1-yl)-9-(4-fluorobenzyl)-6-oxo-6,9-dihydro-1H-purin-8-carboxamide | | | 860.2 |

TABLE 1-13

| Example No. | IUPAC name | Structural formula | Salt | MS |
|---|---|---|---|---|
| 48 | 3-(2-amino-9-(4-fluoro-benzyl)-6-oxo-6,9-dihydro-1H-purin-8-yl)-N-(14-((6S)-4-(4-chloro-phenyl)-2,3,9-trimethyl-6H-thieno[3,2-f][1,2,4]triazolo[4,3-a][1,4]diazepin-6-yl)-13-oxo-3,6,9- | | | 936.3 |

TABLE 1-13-continued

| Example No. | IUPAC name | Structural formula | Salt | MS |
|---|---|---|---|---|
| | trioxa-12-azatetradec-1-yl)benzamide | | | |
| 49 | N²-acetyl-S-(2-amino-9-(4-methylbenzyl)-6-oxo-6,9-dihydro-1H-purin-8-yl)-N-(14-((6S)-4-(4-chlorophenyl)-2,3,9-trimethyl-6H-thieno[3,2-f][1,2,4]triazolo[4,3-a][1,4]diazepin-6-yl)-13-oxo-3,6,9-trioxa-12-azatetradec-1-yl)-L-cysteinamide | | | 973.1 |

TABLE 1-14

| Example No. | IUPAC name | Structural formula | Salt | MS |
|---|---|---|---|---|
| 50 | N²-acetyl-S-(2-amino-9-(4-chlorobenzyl)-6-oxo-6,9-dihydro-1H-purin-8-yl)-N-(14-((6S)-4-(4-chlorophenyl)-2,3,9-trimethyl-6H-thieno[3,2-f][1,2,4]triazolo[4,3-a][1,4]diazepin-6-yl)-13-oxo-3,6,9-trioxa-12-azatetradec-1-yl)-L-cysteinamide | | | 993.1 |
| 51 | N²-acetyl-S-(2-amino-9-(4-fluorobenzyl)-6-oxo-6,9-dihydro-1H-purin-8-yl)-N-(14-((6S)-4-(4-chlorophenyl)-2,3,9-trimethyl-6H-thieno | | | 977.1 |

TABLE 1-14-continued

| Example No. | IUPAC name | Structural formula | Salt | MS |
|---|---|---|---|---|
| | [3,2-f][1,2,4]triazolo[4,3-a][1,4]diazepin-6-yl)-13-oxo-3,6,9-trioxa-12-azatetradec-1-yl)-L-cysteinamide | | | |

TABLE 1-15

| Example No. | IUPAC name | Structural formula | Salt | MS |
|---|---|---|---|---|
| 52 | (2E)-3-(2-amino-9-(4-fluorobenzyl)-6-oxo-6,9-dihydro-1H-purin-8-yl)-N-(14-((6S)-4-(4-chlorophenyl)-2,3,9-trimethyl-6H-thieno[3,2-f][1,2,4]triazolo[4,3-a][1,4]diazepin-6-yl)-13-oxo-3,6,9-trioxa-12 azatetradec-1-yl) acrylamide | | | 886.1 |
| 53 | $N^2$-acetyl-N-(14-((6S)-4-(4-chlorophenyl)-2,3,9-trimethyl-6H-thieno[3,2-f][1,2,4]triazolo[4,3-a][1,4]diazepin-6-yl)-13-oxo-3,6,9-trioxa-12-azatetradec-1-yl)-S-(9-(4-fluorobenzyl)-1,3-dimethyl-2,6-dioxo-2,3,6,9-tetrahydro-1H-purin-8-yl)-L-cysteinamide | | | 1006.2 |

TABLE 1-16

| Example No. | IUPAC name | Structural formula | Salt | MS |
|---|---|---|---|---|
| 54 | (2E)-N-(14-((6S)-4-(4-chlorophenyl)-2,3,9-trimethyl-6H-thieno[3,2-f][1,2,4]triazolo[4,3-a][1,4]diazepin-6-yl)-13-oxo-3,6,9-trioxa-12-azatetradec-1-yl)-3-(9-(4-fluorobenzyl)-1,3-dimethyl-2,6-dioxo-2,3,6,9-tetrahydro-1H-purin-8-yl)acrylamide | | | 915.4 |
| 55 | (2E)-N-(21-chloro-3,6,9,12,15-pentaoxahenicos-1-yl)-3-(9-(4-fluorobenzyl)-1,3-dimethyl-2,6-dioxo-2,3,6,9-tetrahydro-1H-purin-8-yl)acrylamide | | | 696.3 |
| 56 | $N^2$-acetyl-S-(2-amino-9-(4-fluorobenzyl)-6-oxo-6,9-dihydro-1H-purin-8-yl)-N-(21-chloro-3,6,9,12,15-pentaoxahenicos-1-yl)-L-cysteinamide | | | 780.2935 |

TABLE 1-17

| Example No. | IUPAC name | Structural formula | Salt | MS |
|---|---|---|---|---|
| 57 | $N^2$-acetyl-S-(2-amino-9-(4-fluorobenzyl)-6-oxo-6,9-dihydro-1H-purin-8-yl)-N-(1-((6S)-4-(4-chlorophenyl)-2,3,9-trimethyl-6H-thieno[3,2-f][1,2,4]triazolo | | | 1005.3426 |

TABLE 1-17-continued

| Example No. | IUPAC name | Structural formula | Salt | MS |
|---|---|---|---|---|
| | [4,3-a][1,4] diazepin-6-yl)-2-oxo-7,10,13-trioxa-3-aza-hexadecan-16-yl)-L-cysteinamide | | | |
| 58 | N-(3-(2-(2-(3-((2-amino-9-(4-fluoro-benzyl)-6-oxo-6,9-dihydro-1H-purin-8-yl) amino) propoxy) ethoxy) ethoxy) propyl)-2-((6S)-4-(4-chloro-phenyl)-2,3,9-trimethyl-6H-thieno[3,2-f][1,2,4]triazolo[4,3-a][1,4]diazepin-6-yl) acetamide | | | 860.3230 |

TABLE 1-18

| Example No. | IUPAC name | Structural formula | Salt | MS |
|---|---|---|---|---|
| 59 | (1R)-1-(3-((18-((N-acetyl-S-(2-amino-9-(4-fluoro-benzyl)-6-oxo-6,9-dihydro-1H-purin-8-yl)-L-cysteinyl) amino)-4-oxo-9,12,15-trioxa-5-aza-octadecan-1-oyl)amino) phenyl)-3-(3,4-dimethoxy-phenyl) propyl 1-(3,3-dimethyl-2-oxo-pentanoyl) piperidine-2-carboxylate | | | 1229.5726 |

TABLE 1-18-continued

| Example No. | IUPAC name | Structural formula | Salt | MS |
|---|---|---|---|---|
| 60 | (3R,5S,6R)-5-methoxy-4-((2R,3R)-2-methyl-3-(3-methyl but-2-en-1-yl)oxiran-2-yl)-1-oxaspiro[2.5]oct-6-yl(3-(2-(2-(3-((N-acetyl-S-(2-amino-9-(4-fluorobenzyl)-6-oxo-6,9-dihydro-1H-purin-8-yl)-L-cysteinyl)amino)propoxy)ethoxy)ethoxy)propyl)carbamate | | | 931.4408 |

TABLE 1-19

| Example No. | IUPAC name | Structural formula | Salt | MS |
|---|---|---|---|---|
| 61 | N²-acetyl-S-(2-amino-9-((4aR,6R,7R,7aS)-2,7-dihydroxy-2-oxide tetrahydro-4H-furo[3,2-d][1,3,2]dioxaphosphinin-6-yl)-6-oxo-6,9-dihydro-1H-purin-8-yl)-N-(1-((6S)-4-(4-chlorophenyl)-2,3,9-trimethyl-6H-thieno[3,2-f][1,2,4]triazolo[4,3-a][1,4]diazepin-6-yl)-2-oxo-7,10,13,trioxa-3-azahexadecan-16-yl)-L-cysteinamide | | | 1089.2884 |

The compound of the present invention was evaluated for its activity of inducing degradation of a target molecule in vitro by the following tests.

Test Example 1: Evaluation Method Using Cell Stably Expressing EmGFP-HaloTag (Testing Method A)

HeLa cells stably expressing EmGFP-HaloTag were inoculated to Dulbecco's Modified Eagle Medium (DMEM) and cultured for 24 hours. Then, a test compound (specifically, compounds of Examples 1 to 7, 9 to 11, 13 to 15, 17 to 20, 24 to 27, 29, 32 to 33, 36 to 42, 44 to 46 and 56) was added thereto at the final concentration shown in Table 2, followed by incubation for 24 hours under conditions of 37° C./5% $CO_2$. The cells were washed with PBS three times and treated with a cell lysis solution containing a proteolytic enzyme inhibitor to obtain a cell extract. The cell extract was subjected to SDS-PAGE. After the electrophoresis, GFP and actin were detected by Western blot. The ratio of the GFP/actin value of the drug-treated cells to the GFP/actin value of a control group in drug-untreated cells was regarded as an activity value. A value of 1 or less represents that degradation of EmGFP-HaloTag was promoted.

Test Example 2: Evaluation Using Cell Transiently Overexpressing EmGFP-HaloTag (Testing Method B)

HeLa cells were inoculated to Dulbecco's Modified Eagle Medium (DMEM) and cultured for 24 hours. Cells overexpressing EmGFP-HaloTag were obtained by transfection with a plasmid pCMV-EmGFP-HaloTag encoding EmGFP-HaloTag. On the next day, a test compound (specifically, compounds of Examples 8, 12, 16, 21 to 23, 28, 30 and 31) was added thereto at the final concentration shown in Table 2, followed by incubation for 24 hours under conditions of 37° C./5% $CO_2$. The cells were washed with PBS three times and treated with a cell lysis solution containing a proteolytic enzyme inhibitor to obtain a cell extract. The cell extract was subjected to SDS-PAGE. After the electrophoresis, GFP and actin were detected by Western blot. The ratio of the GFP/actin value of the drug-treated cells to the GFP/actin value of a control group in drug-untreated cells was regarded as an activity value. A value of 1 or less represents that degradation of EmGFP-HaloTag was promoted.

Test Example 3: Evaluation Using HeLa Cell (Testing Method C)

HeLa cells were inoculated to Dulbecco's Modified Eagle Medium (DMEM) and cultured for 24 hours. A test compound (specifically, compounds of Examples 47 to 52, 59 and 60) was added thereto at the final concentration shown in Table 2, followed by incubation for 24 hours under conditions of 37° C./5% $CO_2$. The cells were washed with PBS three times and treated with a cell lysis solution containing a proteolytic enzyme inhibitor to obtain a cell extract. The cell extract was subjected to SDS-PAGE. After the electrophoresis, Brd4, FKBP12 or MetAP2 and actin were detected by Western blot. The ratio of the Brd4, FKBP12 or MetAP2/actin value of the drug-treated cells to the Brd4, FKBP12 or MetAP2/actin value of a control group in drug-untreated cells was regarded as an activity value. A value of 1 or less represents that degradation of Brd4, FKBP12 or MetAP2 was promoted.

Test Example 4: Evaluation Using A549 Cell (Testing Method D)

A549 cells were inoculated to Dulbecco's Modified Eagle Medium (DMEM) and cultured for 24 hours. A test compound (specifically, compounds of Examples 57 and 58) was added thereto at the final concentration shown in Table 2, followed by incubation for 24 hours under conditions of 37° C./5% $CO_2$. The cells were washed with PBS three times and treated with a cell lysis solution containing a proteolytic enzyme inhibitor to obtain a cell extract. The cell extract was subjected to SDS-PAGE. After the electrophoresis, Brd4 and actin were detected by Western blot. The ratio of the Brd4/actin value of the drug-treated cells to the Brd4/actin value of a control group in drug-untreated cells was regarded as an activity value. A value of 1 or less represents that degradation of Brd4 was promoted.

The activity of inducing degradation of the target protein by the compounds of Examples obtained in Test Examples 1 to 4 is shown in Table 2.

TABLE 2

| Example No. | Test method | Test compound concentration (uM) | Target protein | Activity value |
|---|---|---|---|---|
| 1 | A | 10 | HaloTag | 0.7 |
| 2 | A | 10 | HaloTag | 0.9 |
| 3 | A | 100 | HaloTag | 0.3 |
| 4 | A | 10 | HaloTag | 0.8 |
| 5 | A | 1 | HaloTag | 0.3 |
| 6 | A | 10 | HaloTag | 0.94 |
| 7 | A | 5 | HaloTag | 0.79 |
| 8 | B | 1 | HaloTag | 0.7 |
| 9 | A | 5 | HaloTag | 0.47 |
| 10 | A | 1 | HaloTag | 0.3 |
| 11 | A | 10 | HaloTag | 0.7 |
| 12 | B | 10 | HaloTag | 0.45 |
| 13 | A | 1 | HaloTag | 0.1 |
| 14 | A | 1 | HaloTag | 0.2 |
| 15 | A | 1 | HaloTag | 0.9 |
| 16 | B | 10 | HaloTag | 0.4 |
| 17 | A | 1 | HaloTag | 0.7 |
| 18 | A | 1 | HaloTag | 0.1 |
| 19 | A | 10 | HaloTag | 0.5 |
| 20 | A | 10 | HaloTag | 0.2 |
| 21 | B | 1 | HaloTag | 0.3 |
| 22 | B | 10 | HaloTag | 0.7 |
| 23 | B | 1 | HaloTag | 0.7 |
| 24 | A | 1 | HaloTag | 0.5 |
| 25 | A | 1 | HaloTag | 0.9 |
| 26 | A | 1 | HaloTag | 0.5 |
| 27 | A | 1 | HaloTag | 0.7 |
| 28 | B | 1 | HaloTag | 0.4 |
| 29 | A | 100 | HaloTag | 0.5 |
| 30 | B | 1 | HaloTag | 0.2 |
| 31 | B | 1 | HaloTag | 0.4 |
| 32 | A | 100 | HaloTag | 0.7 |
| 33 | A | 1 | HaloTag | 0.9 |
| 36 | A | 10 | HaloTag | 0.9 |
| 37 | A | 1 | HaloTag | 0.7 |
| 38 | A | 100 | HaloTag | 0.8 |
| 39 | A | 1 | HaloTag | 0.7 |
| 40 | A | 1 | HaloTag | 0.7 |
| 41 | A | 1 | HaloTag | 0.5 |
| 42 | A | 1 | HaloTag | 0.8 |
| 44 | A | 1 | HaloTag | 0.9 |
| 45 | A | 10 | HaloTag | 0.7 |
| 46 | A | 100 | HaloTag | 0.2 |
| 47 | C | 1 | BRD4 | 0.4 |
| 48 | C | 10 | BRD4 | 0.8 |
| 49 | C | 1 | BRD4 | 0.8 |
| 50 | C | 1 | BRD4 | 0.2 |
| 51 | C | 1 | BRD4 | 0.6 |
| 52 | C | 10 | BRD4 | 0.8 |
| 56 | A | 10 | HaloTag | 0.55 |

TABLE 2-continued

| Example No. | Test method | Test compound concentration (uM) | Target protein | Activity value |
|---|---|---|---|---|
| 57 | D | 1 | BRD4 | 0.9 |
| 58 | D | 1 | BRD4 | 0.8 |
| 59 | C | 1 | FKBP12 | 0.5 |
| 60 | C | 0.1 | MetAP2 | 0.7 |

The results of Test Examples 1 to 4 demonstrated that compound (I) has the activity of inducing degradation of a target molecule.

Test Example 5: Evaluation Using Atg5KO MEF

Atg5$^{-/-}$ mouse embryonic fibroblast (MEF) cells or Atg5$^{+/+}$ MEF cells were inoculated to Dulbecco's Modified Eagle Medium (DMEM) and cultured for 24 hours. Cells overexpressing EmGFP-HaloTag were obtained by transfection with a plasmid pCMV-EmGFP-HaloTag (SEQ ID NO: 1) encoding EmGFP-HaloTag. On the next day, the compound of Example 56 was added thereto at a final concentration of 10 μM, followed by incubation for 24 hours under conditions of 37° C./5% $CO_2$. The cells were washed with PBS three times and treated with a cell lysis solution containing a proteolytic enzyme inhibitor to obtain a cell extract. The cell extract was subjected to SDS-PAGE. After the electrophoresis, GFP and actin were detected by Western blot. The ratio of the GFP/actin value of the drug-treated cells to the GFP/actin value of a control group in drug-untreated cells was regarded as an activity value. A value of 1 or less represents that degradation of EmGFP-HaloTag was promoted.

TABLE 3

| MEF | | 0h | 24 h |
|---|---|---|---|
| Atg5 | KO | 1.0 | 1.1 |
| | WT | 1.0 | 0.3 |

The results of Test Example 5 demonstrated that the degradation of a target molecule induced by compound (I) is mediated by autophagy.

Preparation Example 1

A medicament containing the compound of the present invention as an active ingredient can be produced by, for example, the following formulation.

1. Capsule

| (1) Compound obtained in Example 1 | 40 mg |
|---|---|
| (2) Lactose | 70 mg |
| (3) Microcrystalline cellulose | 9 mg |
| (4) Magnesium stearate | 1 mg |
| One capsule | 120 mg |

(1), (2), (3) and ½ of (4) are mixed and then granulated. The remaining (4) is added thereto, and the whole is enclosed in a gelatin capsule.

2. Tablet

| (1) Compound obtained in Example 1 | 40 mg |
|---|---|
| (2) Lactose | 58 mg |
| (3) Corn starch | 18 mg |
| (4) Microcrystalline cellulose | 3.5 mg |
| (5) Magnesium stearate | 0.5 mg |
| One tablet | 120 mg |

(1), (2), (3), ⅔ of (4) and ½ of (5) are mixed and then granulated. The remaining (4) and (5) are added to the granules, which are then compressed to form a tablet.

Preparation Example 2

In 50 mL of Japanese Pharmacopoeia distilled water for injection, 50 mg of the compound obtained in Example 1 is dissolved, and then brought to 100 mL by the addition of Japanese Pharmacopoeia distilled water for injection. This solution is filtered under sterile conditions. Next, 1 mL of this solution is charged into each vial for injection under sterile conditions, which is then freeze-dried and hermetically sealed.

INDUSTRIAL APPLICABILITY

The compound of the present invention can cause specific uptake of a targeted intracellular molecule by phagocytic cells and degradation thereof by the phagocytic cells. Thus, the compound of the present invention can be used as a tool for analyzing the mechanism of a disease involving a target molecule and is expected to provide a drug effective for the prevention or treatment of the disease.

The invention claimed is:

1. A compound or a salt thereof, the compound being represented by the following formula (I):

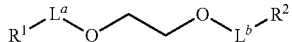
(I)

wherein
R$^1$ represents a halogenated C$_1$-C$_{12}$ alkoxy group,

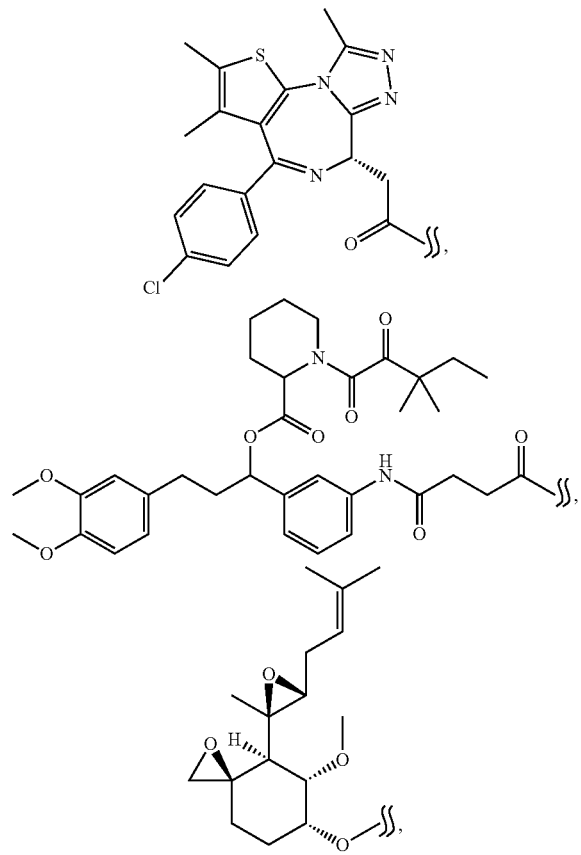

L$^a$ represents a bond or a chain linker having 1 to 10 atoms in a backbone,
L$^b$ represents
i) a bond,
ii) a chain linker having 1 to 13 atoms in a backbone, or
iii) formula (II)

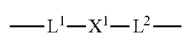
(II)

wherein L$^1$ represents a bond or a chain linker having 1 to 10 atoms in a backbone,
X$^1$ represents an optionally substituted divalent cyclic group, and
L$^2$ represents a bond or a chain linker having 1 or 2 atoms in a backbone, and R$^2$ represents a group selected from the following formulas:

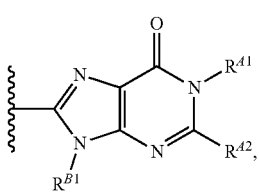
(III)

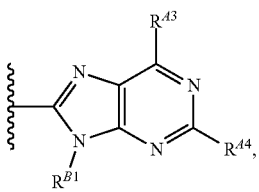
(IV)

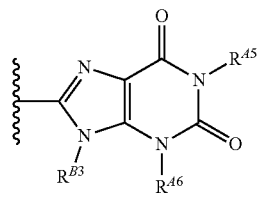
(V)

wherein
R$^{A1}$, R$^{A2}$, R$^{A3}$, R$^{A4}$, R$^{A5}$, and R$^{A6}$ each independently represent a hydrogen atom or a substituent,
R$^{B1}$, R$^{B2}$, and R$^{B3}$ each independently represent an optionally substituted hydrocarbon ring group, an optionally substituted unsaturated heterocyclic group, or —X$^2$—R$^3$,
wherein X$^2$ represents an optionally substituted methylene group, and R$^3$ represents an optionally substituted cyclic group.

2. The compound according to claim 1 or a salt thereof, wherein R$^2$ represents the following formula:

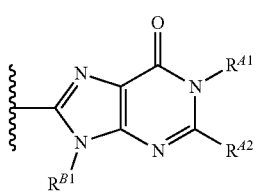
(III)

wherein
R$^{A1}$ and R$^{A2}$ each independently represent a hydrogen atom or a substituent, and
R$^{B1}$ represents an optionally substituted hydrocarbon ring group, an optionally substituted unsaturated heterocyclic group, —X$^2$—R$^3$ wherein
X$^2$ represents an optionally substituted methylene group, and R$^3$ represents an optionally substituted cyclic group.

3. A medicament comprising a compound or a salt thereof according to claim 1.

4. The compound according to claim 1 or a salt thereof, wherein
L$^a$ is a C$_{1-6}$ alkylene group or a —NH—C$_{1-6}$ alkylene group;

$L^b$ is a linker i) represented by the following formula IX:

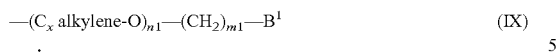
—($C_x$ alkylene-O)$_{n1}$—(CH$_2$)$_{m1}$—B$^1$ (IX)

wherein,
x is 2 or 3,
n1 is 1 to 3,
m1 is 1 to 3, and
B$^1$ is:
(i) a bond,
(ii) —NH—,
(iii) —NH—(CO)—B$^2$— wherein B$^2$ represents a bond, —C$_{1-3}$ alkylene-NH—, —C$_{1-3}$ alkylene-S—, or a C$_{2-3}$ alkenylene group,
(iv) a —C$_{2-3}$ alkynylene group,
(v) a —NH—C$_{1-3}$ alkylene group, or
(vi) a —N—C$_{1-6}$ alkyl-carbonyl-L-cysteinamide; or ii) represented by the following formula II:

-L$^1$-X$^1$-L$^2$- (II)

wherein
L$^1$ is —(C$_y$ alkylene-O)$_{n2}$—(CH$_2$)$_{m2}$—, or —(C$_y$ alkylene-NH)$_{n2}$—(CH$_2$)$_{m2}$—,
wherein,
y is 2 or 3,
n2 is 1 to 6, and
m2 is 0 to 3,
X$^1$ is an optionally substituted divalent 5- or 6-membered aromatic carbocyclic group, an optionally substituted divalent 5- or 6-membered aromatic heterocyclic group, or an optionally substituted divalent 6-membered nonaromatic heterocyclic group, and
L$^2$ is a bond or a carbonyl group; and
R$^2$ represents a group selected from the following formulas:

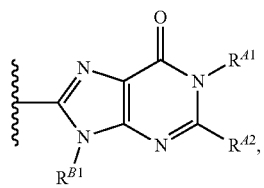
(III)

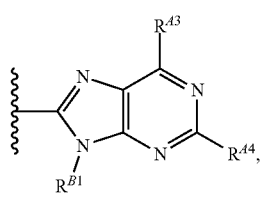
(IV)

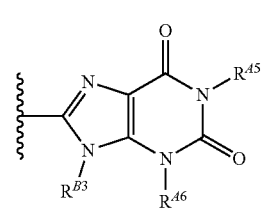
(V)

wherein
R$^{A1}$, R$^{A2}$, R$^{A3}$, R$^{A4}$, R$^{A5}$, and R$^{A6}$ are each independently a hydrogen atom, an optionally substituted amino group, a methylcarbonyl group, or a C$_{1-6}$ alkyl group, R$^{B1}$, R$^{B2}$, and R$^{B3}$ are each independently:
(i) an optionally substituted C$_{3-10}$ cycloalkyl group;
(ii) an optionally substituted C$_{6-14}$ aryl group;
(iii) an optionally substituted unsaturated heterocyclic group;
(iv) a methylene group substituted by a C$_{6-14}$ aryl group,
(v) a methylene group substituted by a halogenated C$_{6-14}$ aryl group,
(vi) a methylene group substituted by a C$_{6-14}$ aryl group substituted by one to three cyano groups,
(vii) a methylene group substituted by a C$_{6-14}$ aryl group substituted by one to three C$_{1-6}$ alkyl groups,
(viii) a methylene group substituted by a C$_{6-14}$ aryl group substituted by one to three C$_{1-6}$ alkoxy groups,
(ix) a methylene group substituted by a C$_{6-14}$ aryl group substituted by one to three C$_{1-6}$ alkylsulfonyl groups,
(x) a methylene group substituted by a 5- to 14-membered aromatic heterocyclic group optionally substituted by one to three C$_{1-6}$ alkyl groups, or
(xi) a methylene group substituted by a 5- to 14-membered nonaromatic heterocyclic group.

5. The compound according to claim 4 or a salt thereof, wherein
L$^a$ is an ethylene group or a —NH-ethylene group:
L$^b$ is a linker
i) represented by the following formula IX:

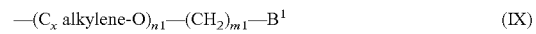
—($C_x$ alkylene-O)$_{n1}$—(CH$_2$)$_{m1}$—B$^1$ (IX)

wherein,
x is 2,
n1 is 2 or 3,
m1 is 1, and
B$^1$ is:
(i) -methylene-NH—, -ethylene-NH—, -methylene-S—, -ethylene-S—, or a vinylene group,
(ii) an acetylene group,
(iii) a —NH-methylene group, or
(iv) —N2 acetyl-L-cysteinamide; or ii) represented by the following formula II:

—L$^1$—X$^1$—L$^2$— (II)

wherein
L$^1$ is —(C$_y$ alkylene-O)$_{n2}$—(CH$_2$)$_{m2}$—, or —(C$_y$ alkylene-NH)$_{n2}$—(CH$_2$)$_{m2}$—,
wherein,
y is 2,
n2 is 1 to 3, and
m2 is 0 to 2,
X$^1$ is a phenylene group substituted by an amide group or an unsubstituted phenylene group, a pyrazolyl ring, a triazolyl, or a piperidinyl substituted by an amide group, and
L$^2$ is a carbonyl group; and
R$^{A1}$, R$^{A2}$, R$^{A3}$, R$^{A4}$, R$^{A5}$, and R$^{A6}$ are each independently a hydrogen atom, an unsubstituted amino group, an amino group substituted by a C$_{1-6}$ alkylcarbonyl group, or a methyl group,
R$^{B1}$, R$^{B2}$, and R$^{B3}$ are each independently:
(i) an optionally substituted cyclopentyl or cyclohexyl group;
(ii) an optionally substituted phenyl group;
(iv) a methylene group substituted by a C$_{6-14}$ aryl group, (v) a methylene group substituted by a $C_{6-14}$ aryl group substituted by fluorine or chlorine at a para, meta or ortho position,
(vi) a methylene group substituted by a $C_{6-14}$ aryl group substituted by one cyano group,
(vii) a methylene group substituted a $C_{6-14}$ aryl group substituted by one $C_{1-6}$ alkyl group,
(viii) a methylene group substituted by a $C_{6-14}$ aryl group substituted by one methoxy group,
(ix) a methylene group substituted by a $C_{6-14}$ aryl group substituted by a methylsulfonyl group,
(x) a methylene group substituted by a 5- or 6-membered aromatic heterocyclic group optionally substituted by one to three $C_{1-6}$ alkyl groups, or (xi) a methylene group substituted by a 5- or 6-membered nonaromatic heterocyclic group.

6. The compound according to claim 4 or a salt thereof, wherein
$L^1$ is (ethylene-O)$_{n2'}$—(CH$_2$)$_{m2'}$— or (propylene-O)$_{n2'}$—(CH$_2$)$_{m2'}$— wherein n2' is 1 to 3, and m2' is 0 to 2,
$L^2$ is a carbonyl group; and
$R^{A1}$, $R^{A2}$, $R^{A3}$, $R^{A4}$, $R^{A5}$, and $R^{A6}$ are each independently a hydrogen atom, a methylcarbonyl group, or a methyl group,
$R^{B1}$, $R^{B2}$, and $R^{B1}$ are each independently:
(i) an optionally substituted cyclopentyl or cyclohexyl group;
(ii) an optionally substituted phenyl group;
(iv) a methylene group substituted by a $C_{6-14}$ aryl group,
(v) a methylene group substituted by a $C_{6-14}$ aryl group substituted by fluorine or chlorine at a para, meta or ortho position,
(vi) a methylene group substituted by a $C_{6-14}$ aryl group substituted by one cyano group,
(vii) a methylene group substituted a $C_{6-14}$ aryl group substituted by a methyl group,
(viii) a methylene group substituted by a $C_{6-14}$ aryl group substituted by one methoxy group,
(ix) a methylene group substituted by a $C_{6-14}$ aryl group substituted by a methylsulfonyl group,
(x) a methylene group substituted by a pyridyl group, a thiazole group, or a pyrazole group substituted by a $C_{1-6}$ alkyl group, or
(xi) a methylene group substituted by a tetrahydropyranyl group.

7. The compound according to claim 4 or a salt thereof, wherein
$R^{B1}$, $R^{B2}$, and $R^{B3}$ are each independently:
(i) an optionally substituted cyclopentyl or cyclohexyl group;
(ii) an optionally substituted phenyl group;
(iv) a methylene group substituted by a $C_{6-14}$ aryl group,
(v) a methylene group substituted by a $C_{6-14}$ aryl group substituted by fluorine or chlorine at a para, meta or ortho position,
(vi) a methylene group substituted by a $C_{6-14}$ aryl group substituted by one cyano group,
(vii) a methylene group substituted a $C_{6-14}$ aryl group substituted by a methyl group,
(viii) a methylene group substituted by a $C_{6-14}$ aryl group substituted by one methoxy group,
(ix) a methylene group substituted by a $C_{6-14}$ aryl group substituted by a methylsulfonyl group,
(x) a methylene group substituted by a pyridyl group, a thiazole group, or a pyrazole group substituted by a methyl group, or
(xi) a methylene group substituted by a tetrahydropyranyl group.

8. The compound according to claim 1 or a salt thereof, wherein
$L^a$ is an ethylene group or a —NH-ethylene group;
$L^b$ is
i) a chain linker represented by the formula:

wherein
n1 is 1 or 2,
m1 is 1, and
$B_1$ is
(i) —NH—,
(ii) —NH—(CO)—,
(iii) —NH—(CO)-ethylene,
(iv) a —NH—$C_{1-3}$ alkylene group, or
(v) —N2 acetyl-L-cysteinamide, or
ii) represented by the formula:

wherein
$L^1$ is -(ethylene-O)$_{n2}$—(CH$_2$)$_{m2}$— wherein n2 is 1 to 3, and m2 is 0 or 1,
$X^1$ is a phenylene group substituted by an amide group, and
$L^2$ is a bond;
wherein,
when $R^2$ is a group of the formula (III),
$R^{A1}$ is a hydrogen atom,
$R^{A2}$ is an optionally substituted amino group, and
$R^{B1}$ is
(i) an optionally substituted unsaturated heterocyclic group,
(ii) a methylene group substituted by a halogenated $C_{6-14}$ aryl group, or
(iii) a methylene group substituted by a $C_{6-14}$ aryl group substituted by a $C_{1-6}$ alkyl group;
when $R^2$ is a group of the formula (IV),
$R^{A3}$ is an optionally substituted amino group,
$R^{A4}$ is a hydrogen atom, and
$R^{B2}$ is a methylene group substituted by a halogenated $C_{6-14}$ aryl group; and
when $R^2$ is a group of the formula (V),
$R^{A5}$ and $R^{A6}$ are each independently
(i) a hydrogen atom, or
(ii) a $C_{1-6}$ alkyl group, and
$R^{B3}$ is a methylene group substituted by a halogenated $C_{6-14}$ aryl group.

9. The compound according to claim 8 or a salt thereof, wherein
$B_1$ is
(i) —NH—,
(ii) —NH—(CO)—,
(iii) —NH—(CO)-ethylene,
(iv) an aminomethylene group, or
(v) —N2 acetyl-L-cysteinamide;
$R^{A2}$ is, an unsubstituted amino group,
wherein:
when $R^2$ is a group of the formula (III),
$R_{B1}$ is
(ii) a methylene group substituted by a $C_{6-14}$ aryl group substituted by fluorine or chlorine, or (iii) a methylene group substituted by a $C_{6-14}$ aryl group substituted by a C1-6 alkyl group;
when $R^2$ is a group of the formula (IV),
$R^{A3}$ is an unsubstituted amino group,
$R^{A4}$ is a hydrogen atom, and
$R^{B2}$ is a methylene group substituted by a $C_{6-14}$ aryl group substituted by fluorine or chlorine; and
when $R^2$ is a group of the formula (V),
$R^{A5}$ and $R^{A6}$ are each independently
(i) a hydrogen atom, or
(ii) a methyl group, and
$R^{B3}$ is a methylene group substituted by a $C_{6-14}$ aryl group substituted by fluorine or chlorine.

10. The compound according to claim 8 or a salt thereof, wherein
when $R^2$ is a group of the formula (III),
$R^{B1}$ is
(ii) a methylene group substituted by a $C_{6-14}$ aryl group substituted by fluorine or chlorine, or
(iii) a methylene group substituted by a $C_{6-14}$ aryl group substituted by a methyl group.

11. The compound according to claim 1, wherein $R^1$ represents: a halogenated $C_1$-$C_6$ alkoxy group, or 12. The compound according to claim 1, wherein $R^1$ represents: a halogenated $C_1$-$C_6$ alkoxy group, or

[Formula 10]

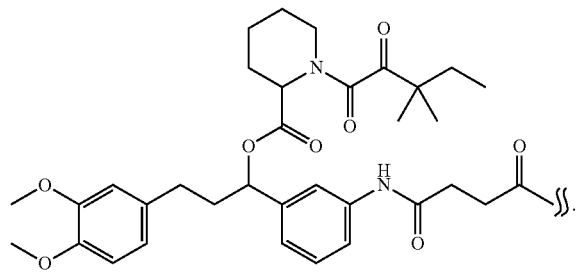

13. The compound according to claim 1, wherein $R^1$ represents: a halogenated $C_1$-$C_6$ alkoxy group, or

[Formula 11]

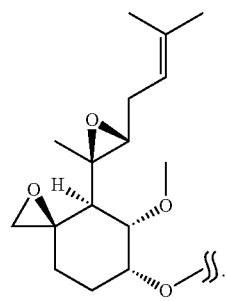

* * * * *